United States Patent
Hoogenboom et al.

(10) Patent No.: US 12,281,135 B2
(45) Date of Patent: Apr. 22, 2025

(54) SYNTHESIS OF 6-AZIDO-6-DEOXY-2-N-ACETYL-HEXOSAMINE-NUCLEOSIDE DIPHOSPHATE

(71) Applicant: Synaffix B.V., Oss (NL)

(72) Inventors: Jorin Hoogenboom, Oss (NL); Maria Antonia Wijdeven, Oss (NL); Jorge Merijn Mathieu Verkade, Oss (NL); Floris Louis Van Delft, Oss (NL); Sander Sebastiaan Van Berkel, Oss (NL)

(73) Assignee: SYNAFFIX B.V., Oss (NL)

( * ) Notice: Subject to any disclaimer, the term of this patent is extended or adjusted under 35 U.S.C. 154(b) by 635 days.

(21) Appl. No.: 17/582,707

(22) Filed: Jan. 24, 2022

(65) Prior Publication Data
US 2022/0162252 A1     May 26, 2022

Related U.S. Application Data

(63) Continuation of application No. PCT/NL2020/050488, filed on Jul. 27, 2020.

(30) Foreign Application Priority Data

Jul. 25, 2019 (NL) ...................... 2023572

(51) Int. Cl.
*C07H 19/10* (2006.01)
*C07H 1/02* (2006.01)
*C07H 1/04* (2006.01)
*C07H 15/12* (2006.01)

(52) U.S. Cl.
CPC .............. *C07H 19/10* (2013.01); *C07H 1/02* (2013.01); *C07H 1/04* (2013.01); *C07H 15/12* (2013.01)

(58) Field of Classification Search
None
See application file for complete search history.

(56) References Cited

U.S. PATENT DOCUMENTS 9,988,661 B2 * 6/2018 Van Berkel ........ A61K 47/6803

FOREIGN PATENT DOCUMENTS

CN     108865918 A     11/2018

OTHER PUBLICATIONS

Mayer et al., Bioorganic & Medicinal Chemistry Letters, vol. 21(4), 2011, pp. 1199-1201. (Year: 2011).*
Hu et al., Nature Chemical Biology, vol. 13(12), 2017, pp. 1627-1273 plus Supplementary pages for Online methods. (Year: 2017).*
Supplementary Information for Hu et al., Nature Chemical Biology, vol. 13(12), 2017, 37 pages. (Year: 2017).*
Ahmadipour et al., "Recent advances in the chemical synthesis of sugar-nucleotides", Carbohydrate Research, vol. 451, 2017, pp. 95-109 (15 pages).
Bosco et al., "6-Azido D-galactose transfer to N-acetyl-D-glucosamine derivative using commercially available β1, 4-galactosyltransferase", Tetrahedron Letters, vol. 49, No. 14, 2008, pp. 2294-2297 (4 pages).
Bourgeaux et al., "Two-step enzymatic synthesis of UDP-N-acetylgalactosamine" Bioorganic & Medicinal Chemistry Letters, vol. 15, 2005, pp. 5459-5462 (4 pages).
Cai et al., "Substrate specificity of N-acetylhexosamine kinase towards N-acetylgalactosamine derivatives", Bioorganic & Medicinal Chemistry Letters, vol. 19, No. 18, 2009, pp. 5433-5435 (3 pages).
Chuh et al., "Changes in Metabolic Chemical Reporter Structure Yield a Selective Probe of O-GlcNAc Modification", Journal of the American Chemical Society, vol. 136, 2014, pp. 12283-12295 (13 pages).
Guan et al., "Enzymatic synthesis of UDP-GlcNAc/UDP-GalNAc analogs using N-acetylglucosamine 1-phosphate uridyltransferase (GlmU)", Chemical Communications, vol. 45, 2009, pp. 6976-6978 (3 pages).
Guan et al., "Highly Efficient Synthesis of UDP-GalNAc/GlcNAc Analogues with Promiscuous Recombinant Human UDP-GalNAc Pyrophosphorylase AGX1", Chemistry (Weinheim an der Bergstrasse, Germany), vol. 16. No. 45, 2010, 13343-13345 (7 pages).
Hang et al., "A metabolic labeling approach toward proteomic analysis of mucin-type O-linked glycosylation", Proceedings of the National Academy of Sciences, vol. 100, No. 25, 2003 (10 pages).
Heidlas et al., "Practical Enzyme-Based Syntheses of Uridine 5'-Diphosphogalactose and Uridine 5'-Diphospho-N-Acetylgalactosamine on a Gram Scale." The Journal of Organic Chemistry, vol. 57, No. 1, 1992, pp. 152-157 (6 pages).
Li et al., "Preparation of Well-Defined Antibody-Drug Conjugates through Glycan Remodeling and Strain-Promoted Azide-Alkyne Cycloadditions", Angewandte Chemie, vol. 126, No. 28, 2014, pp. 7179-7182 (9 pages).
Liu et al., "Biosynthesis of nucleotide sugars by a promiscuous UDP-sugar pyrophosphorylase from *Arabidopsis thaliana* (AtUSP)", Bioorganic & Medicinal Chemistry Letters, vol. 23, 2013, pp. 3764-3768 (5 pages).
Masuko et al., "Chemoenzymatic synthesis of uridine diphosphate-GlcNAc and uridine diphosphate-GalNAc analogs for the preparation of unnatural glycosaminoglycans", The Journal of Organic Chemistry, vol. 77, No. 3, 2012, pp. 1449-1456 (22 pages).
Mayer et al., "6"-Azido-6"-deoxy-UDP-N-acetylglucosamine as a glycosyltransferase substrate", Bioorganic & Medicinal Chemistry Letters, vol. 21, No. 4, 2011, pp. 1199-1201 (3 pages).

(Continued)

*Primary Examiner* — Traviss C McIntosh, III
(74) *Attorney, Agent, or Firm* — Foley & Lardner LLP

(57) ABSTRACT

The current invention concerns methods for the synthesis of 6-azido-6-deoxy-2-N-acetyl-monosaccharide-nucleoside diphosphate, in particular 6-azido-6-deoxy-2-N-acetyl-D-galactosamine-nucleoside diphosphate or 6-azido-6-deoxy-2-N-acetyl-D-glucosamine-nucleoside diphosphate. The synthesis method according to the invention is characterized by being highly efficient and high yielding. Also part of the present invention are key intermediates of this process.

20 Claims, No Drawings

(56) References Cited

OTHER PUBLICATIONS

Takaya et al., "Rational Design, Synthesis, and Characterization of Novel Inhibitors for Human β1, 4-Galactosyltransferase." Journal of Medicinal Chemistry, vol. 48, No. 19, 2005, pp. 6054-6065 (12 pages).
Van Geel et al., "Chemoenzymatic conjugation of toxic payloads to the globally conserved N-glycan of native mAbs provides homogeneous and highly efficacious antibody-drug conjugates", Bioconjugate Chemistry, vol. 26, No. 11, 2015, pp. 2233-2242 (10 pages).
Verkade et al., "A polar sulfamide spacer significantly enhances the manufacturability, stability, and therapeutic index of antibody-drug conjugates", Antibodies, vol. 7, No. 1, 2018 (12 pages).
Warnock et al., "In vitro galactosylation of human IgG at 1 kg scale using recombinant galactosyltransferase" Biotechnology and Bioengineering, vol. 92, No. 7, 2005, pp. 831-842 (12 pages).
Wen et al., "Chemoenzymatic Synthesis of Unnatural Nucleotide Sugars for Enzymatic Bioorthogonal Labeling", ACS Catalysis, vol. 8, No. 8, 2018, pp. 7659-7666 (8 pages).
Wittmann et al., "1H-Tetrazole as Catalyst in Phosphomorpholidate Coupling Reactions: Efficient Synthesis of GDP-Fucose, GDP-Mannose, and UDP-Galactose", The Journal of Organic Chemistry, vol. 62, No. 7, 1997, pp. 2144-2147 (4 pages).
Yamamoto et al., Preparation of Uridine Diphosphate-N-Acetylgalactosamine from Uridine Diphosphate-N-Acetylglucosamine by Using Microbial Enzymes., Applied and Environmental Microbiology, vol. 41, No. 2, 1981, pp. 392-395 (4 pages).
Zeglis et al., "Enzyme-mediated methodology for the site-specific radiolabeling of antibodies based on catalyst-free click chemistry", Bioconjugate Chemistry, vol. 24, No. 6, 2013, pp. 1057-1067 (23 pages).
Zou et al., "One-pot three-enzyme synthesis of UDP-Glc, UDP-Gal, and their derivatives", Carbohydrate Research, vol. 373, 2013, pp. 76-81 (6 pages).
International Search Report and Written Opinion of the International Searching Authority issued for PCT Appl. Ser. No. PCT/NL2020/050488 dated Jan. 28, 2021 (23 pages).
Bülter et al., "Enzymatic synthesis of nucleotide sugars", Glycoconjugate Journal, vol. 16, No. 2, 1999, pp. 147-159 (13 pages).
Bülter et al., Carbohydr. Res. 1997, 305, 469.
Cai et al., "Recent progress in enzymatic synthesis of sugar nucleotides", Journal of Carbohydrate Chemistry, vol. 31, No. 7, 2012, pp. 535-552.
Carlson et al., "Preparation of crystalline a-D-galactosamine-1-phosphoric acid and its conversion to UDP-N-acetylgalactosamine", Biochemistry, vol. 3, 1964, pp. 402-405.
Dabrowski-Tumanski et al., "Efficient and rapid synthesis of nucleoside diphosphate sugars from nucleoside phosphorimidazolides." European Journal of Organic Chemistry, 2013, No. 11, pp. 2147-2154.

Hang et al.,. "Probing glycosyltransferase activities with the Staudinger ligation", Journal of the American Chemical Society, vol. 126, No. 1, 2004, pp. 6-7.
Illarionov et al., "A novel synthesis of N-acetyl-a-d-fucosamine 1-phosphate and uridine 5"-diphospho-N-acetyl-a-d-fucosamine", Russian Chemical Bulletin, vol. 50, No. 7, 2001, pp. 1303-1308.
MacDonald, "Preparation of Glycosyl Phosphates. β-D-Fructopyranose 2-Phosphate" The Journal of Organic Chemistry, vol. 31, No. 2, pp. 513-516, 1966.
Maley et al., "The synthesis of UDP-galactosamine and UDP-N-acetylgalactosamine", Biochemical and Biophysical Research Communications, vol. 39, 1970, 371-378 (8 pages).
Moffatt et al., "Nucleoside Polyphosphates. VIII. 1 New and Improved Syntheses of Uridine Diphosphate Glucose and Flavin Adenine Dinucleotide Using Nucleoside-5'Phosphoramidates2." Journal of the American Chemical Society, vol. 80, No. 14, 1958, pp. 3756-3761.
Moffatt et al., "Nucleoside Polyphosphates. X. 1 The Synthesis and Some Reactions of Nucleoside-5'Phosphoromorpholidates and Related Compounds. Improved Methods for the Preparation of Nucleoside-5'Polyphosphates1", Journal of the American Chemical Society, vol. 83, No. 3, 1961, pp. 649-658.
Morais et al., "Chemoenzymatic synthesis of thio-nod factor intermediates Enzymatic transfer of glucosamine on thiochitobiose derivatives", Canadian Journal of Chemistry, Vo. 84, No. 4, 2006, pp. 587-596.
Piller et al., "The preparation of UDP-N-acetylgalactosamine from UDP-N-acetylglucosamine employing UDP-N-acetylglucosamine-4-epimerase", Analytical Biochemistry, vol. 127, No. 1, 1982, pp. 171-177.
Pouilly et al., "Evaluation of analogues of GalNAc as substrates for enzymes of the mammalian GalNAc salvage pathway", ACS Chemical Biology, vol. 7, No. 4, pp. 753-760, 2012.
Wagner et al., "A survey of chemical methods for sugar-nucleotide synthesis", Natural Product Reports, vol. 26, pp. 1172-1194, 2009.
Guo et al., "Biosynthesis of the Carbamoylated D-Gulosamine Moiety of Streptothricins: Involvement of a Guanidino-N-glycosyltransferase and an N-Acetyl-D-gulosamine Deacetylase", Biosynthesis, Angew Chem. Int. Ed., 2015, vol. 54, pp. 5175-5178.
Knijnenburg et al., "Exploring the Conformational and Biological Versatility of b-Turn-Modified Gramicidin S by Using Sugar Amino Acid Homologues that Vary in Ring Size", Chemistry—A European Journal, Mar. 1, 2011, vol. 17, pp. 3995-4004.
Yeager et al., "Synthesis of Fluorescently Labeled UDP-GlcNAc Analogues and Their Evaluation as Chitin Synthase Substrates", Journal of Organic Chemistry, Sep. 15, 2004, vol. 70, pp. 1269-1275.
Wang et al., "Characterization of Two UDP-Gal:GalNAc-Diphosphate-Lipid β1,3-Galactosyltransferases WbwC from *Escherichia coli* Serotypes O104 and O5", Journal of Bacteriology, Sep. 2014, vol. 196, No. 17, pp. 3122-3133.

* cited by examiner

SYNTHESIS OF 6-AZIDO-6-DEOXY-2-N-ACETYL-HEXOSAMINE-NUCLEOSIDE DIPHOSPHATE

CROSS-REFERENCE TO RELATED APPLICATIONS

The present application is a Continuation of International Patent Application No. PCT/NL2020/050488, filed Jul. 27, 2020, which claims priority to Dutch Patent Application No. 2023572 filed Jul. 25, 2019; the entire contents of all of which are hereby incorporated by reference.

FIELD OF THE INVENTION

The present invention is in the field of functionalized nucleoside sugars and relates to an improved manufacturing of sugar nucleoside diphosphates. More in particular, the invention relates to a process for the chemical conversion of GalNAc or GlcNAc into their respective 6-azido derivatives proceeding through a cyclic sulfate, followed by conversion into respective UDP derivatives through an anomeric phosphorylation step and a UMP coupling step. The invention also relates to various specific intermediates and purification steps.

BACKGROUND OF THE INVENTION

Carbohydrates play a pivotal role in cellular biology through their function in energy metabolism and storage as well as being key components of genetic material and other structural elements. Moreover, carbohydrates attached to proteins or lipids, also referred to as glycans, are of significant importance in cellular communication during cell differentiation and development.

Glycans are defined as the oligosaccharide part of glycoconjugates such as glycoproteins, which may be connected to the protein through a glycosidic ether bond (as in an O-glycoprotein) or an amide bond (as in an N-glycoprotein). In both O- and N-glycoproteins, N-acetylgalactosamine (GalNAc) and N-acetylglucosamine (GlcNAc) are a frequently recurring building blocks, which may be connected directly (GalNAc) to serine or threonine as in O-glycoproteins or directly connect (GlcNAc) to asparagine as in N-glycoproteins. GalNAc or GlcNAc may also be part of a larger oligosaccharide chain in an glycoprotein, either internally or as the most remote monosaccharide, mostly connected via a β-glycosidic bond to another sugar. To incorporate a GalNAc moiety on a protein or oligosaccharide chain, nature has evolved a range of N-acetyl-galactosaminyltransferases (GalNAc-transferases) that are able to transfer the monosaccharide GalNAc from UDP-GalNAc (the donor) to the alcohol moiety of serine/threonine or to another sugar (the acceptor). Similarly, N-acetyl-glucosaminyltransferases (GlcNAc-transferases) can attach GlcNAc to alcohol acceptors. The UDP-GalNAc donor substrate, to this end, is produced from glucose-6-phosphate and glutamate in what is known as the hexosamine pathway. Five subsequent enzymatic transformations result in the formation of UDP-GlcNAc which in turn is converted to UDP-GalNAc under the action of UDP-galactose-4-epimerase, as for example disclosed in Yamamoto et al., Applied Environ. Microbiol. 1981, 41, 392, incorporated by reference.

To investigate in-depth the mechanism and functional role of incorporation of GalNAc into naturally occurring glycans, or for the identification of novel galactosaminyltransferases, requires significant amounts of (labelled) UDP-GalNAc, as for example disclosed in Maley et al., Biochem. Biophys. Res. Commun. 1970, 39, 371, incorporated by reference. As a result, different methodologies for the preparation of UDP-GalNAc (and analogues thereof) have been devised over the years, typically following either chemical procedures, enzymatic transformations or a combination thereof.

Chemical synthesis of sugar nucleotides generally follows one of two routes, as summarized in Ahmadipour et al., Carbohydr. Res. 2017, 451, 95, incorporated by reference: (a) pyrophosphorylation using a sugar-1-phosphate and an activated nucleoside monophosphate (NMP) or (b) direct glycosylation of a glycosyl donor using a nucleoside diphosphate (NDP), with the pyrophosphorylation route being more commonly applied. Pyrophosphorylation therefore requires first the synthesis of a sugar-1-phosphate derivative, for which a large number of approaches have been published, as summarized in Ahmadipour et al., Carbohydr. Res. 2017, 451, 95, incorporated by reference. One of the difficulties in these procedures is to obtain the requisite sugar-1-phosphate with exclusive α-selectivity, the anomeric configuration in the vast majority of sugar nucleotides. The second step of the pyrophosphorylation approach involves the coupling of the sugar-1-phosphate with an activated NMP. The seminal work on coupling with phosphomorpholidates of Moffatt et al., J. Am. Chem. Soc. 1958, 80, 3756, incorporated by reference, is still widely applied, alongside the 1-H-tetrazole modification reported by Wittmann et al., J. Org. Chem. 1997, 62, 2144. However, advances beyond this classical phosphomorpholidate strategy have provided a range of other approaches, summarized in Ahmadipour et al., Carbohydr. Res. 2017, 451, 95, incorporated by reference. One particularly useful approach towards sugar nucleotides involves coupling of the sugar-1-phosphate with an imidazolide-activated NMP, as reviewed in Wagner et al., Nat. Prod. Rep. 2009, 26, 1172, incorporated by reference. The requisite imidazolide may be readily generated from nucleoside monophosphates and activated with $ZnCl_2$ or $MgCl_2$ by a procedure reported by Dabrowski-Tumanski et al., Eur. J. Org. Chem. 2013, 2147, incorporated by reference. However, no generally accepted chemical route towards sugar nucleotides has emerged. Particularly, the majority of the methods are centered around common hexose sugars, with only a subset being suitable for N-acetylated hexosamines, for example due to the use of strongly basic conditions, and/or azido-modified sugars, for example due to the use of phosphate deprotection conditions that are not compatible with azides.

Enzymatic synthesis of sugar nucleotides avoids the use of protection and deprotection steps as is required during chemical synthesis. Moreover, enzymatic formation of a pyrophosphate bond typically proceeds with better efficiency and stereoselectivity compared to the chemical bond formation. Different enzymatic methods have been reported, summarized in Bülter et al., Glycoconj. J. 1999, 16, 147, incorporated by reference, varying in the number of enzymes employed, as well as the type of starting material employed, as reported in Cai et al., J. Carbohydr. Chem. 2012, 31, 535, incorporated by reference. For example, it was reported by Piller et al., Anal. Biochem. 1982, 127, 171, incorporated by reference, that the UDP derivative of N-acetylglucosamine (GlcNAc) can be converted into UDP-GalNAc by a mammalian Gal-4 epimerase. The major drawback of this method is the low yield (30% of an equilibrium GalNAc:GlcNAc) in combination with the difficult separation of UDP-GalNAc from the excess UDP-GlcNAc. An enzymatic route reported by Carlson et al., Biochemistry 1964, 3, 402, incorporated by reference, starts from D-galactosamine and utilizes yeast moult galactokinase to form galactosamine-1-phosphate (GalNH$_2$-1-P). In the next step the purified GalNH$_2$-1-P is coupled to UMP either chemically or enzymatically using a yeast UDP-glucose uridyltransferase, as reported by Heidlas et al., *J. Org. Chem.* 1992, 57, 152, incorporated by reference. In both cases, UDP-GalNH$_2$ is chemically N-acetylated in the final step, resulting in poor overall yields after purification (typically not exceeding 20%). Another enzymatic synthesis, as described by Bülter et al., *Carbohydr. Res.* 1997, 305, 469, incorporated by reference, facilitates the production of UDP-GalNAc by means of a coupled seven-enzyme system converting UMP, sucrose and GalNH$_2$-1-P into UDP-GalNH$_2$ which is finally chemically converted to the N-acetylated product, with an appreciable overall yield of 34%. Zou et al., *Carb. Res.* 2013, 373, 76, incorporated by reference, devised an elegant one-pot-three-enzyme protocol to produce UDP-GalNAc and derivatives, utilizing enzymes derived from *Streptococcus pneumoniae*, i.e. UTP-glucose-1-phosphate uridylyltransferase (SpGalU), galactokinase (SpGalK), and inorganic phosphatase (PPase). In the presence of ATP, SpGalK converts GalNAc to GalNAc-1-P which, in combination with uridine triphosphate (UTP), is the substrate for SpGalK to produce UDP-GalNAc in reasonable yield (32%). The third enzyme in this reaction, yeast inorganic pyrophosphatase (PPase) drives UDP-GalNAc production forward by preventing the reverse reaction, cleaving PPi into two molecules of monophosphate (Pi). Following earlier work, Liu et al., *Bioorg. Med. Chem. Lett.* 2013, 23, 3764, incorporated by reference, applied the same one-pot-three-enzyme methodology whereby UDP-sugar pyrophosphorylase from *Arabidopsis thaliana* (AtUSP) was used instead of SpGalU. A similar three-enzyme method was applied by Bourgeaux et al., *Bioorg. Med. Chem. Lett.* 2005, 15, 5459, incorporated by reference, to produce UDP-GalNAc. Thus, starting from GalNAc, UTP and ATP, using recombinant human GalNAc kinase (GK2) and UDP-GalNAc pyrophosphorylase (AGX1), UDP-GalNAc was synthesised in high yield (68%). Mammalian Here GK2 catalyses the phosphorylation of GalNAc using ATP as phosphate donor. Next, the mammalian AGX1 uses UTP to convert GalNAc-1-P into UDP-GalNAc whereby PPase is used to increase product formation and obtain substantial amounts of UDP-GalNAc. Subsequently, Pouilly et al., *ACS Chem. Biol.* 2012, 7, 753, incorporated by reference, showed the versatility of this methodology by producing several UDP-GalNAc analogues for their use as substrates for polypeptide GalNAc transferase T1 (ppGalNAcT1). Besides the reported enzymatic protocols for the preparation of UDP-GalNAc, a few chemoenzymatic procedures, i.e. employing a combination of enzymatic and chemical steps, have been reported. For instance, Cai et al., *Bioorg. Med. Chem. Lett.*, 2009, 19, 18, 5433 and Guan et al., *Chem. Commun.*, 2009, 6976 and *Chem. Eur. J.* 2010, 16, 13343, incorporated by reference, have described two strategies for the synthesis of UDP-GalNAc and several analogues thereof starting from N-acetylgalactosamine.

Despite the elegancy of (chemo)enzymatic UDP-sugar synthesis, in particular by elimination of lengthy syntheses involving a plethora of (de)protection steps, it is clear that the scalability of enzymatic UDP-sugar synthesis is challenging. Moreover, various enzymes need to be recombinantly expressed, hence a protocol involving (multiple) enzymes will be expensive. Obviously, costs would further increase in case such a UDP-sugar is to be GMP-produced for manufacturing of clinical grade material, as for example disclosed by Warneck et al., *Biotechnol. Bioengin.* 2005, 92, 831, incorporated by reference. Finally, it is likely that most of the requisite enzymes preclude the use of alternative N-substituted galactosamine variants, making enzymatic synthesis of unnatural UDP-GalNAc analogues a challenging task, if not impossible. In this regard, a strong interest has emerged in the use of azido-modified sugars for application in for example metabolic reporter strategy, as reported by Hang et al., *PNAS* 2003, 100, 14846, incorporated by reference, or by controlled labelling of glycoproteins as reported by Zeglis et al. *Bioconj. Chem.* 2013, 24, 1057 and Li et al., *Angew. Chem. Int. Ed.* 2014, 53, 7179, incorporated by reference. In the latter field, van Geel et al., *Bioconj. Chem.* 2015, 26, 2233, incorporated by reference, have shown that UDP-GalNAz can be cleanly installed on monoclonal antibodies, affording stable and homogeneous antibody-drug conjugates after metal-free click conjugation of toxic payload. More recently, it was shown by Verkade et al., *Antibodies*, 7, 12, incorporated by reference that moving azide to the 6-position of GalNAc affords antibody-drug conjugates with reduced aggregation propensity versus GalNAz-containing analogues. It is clear, however, that the manufacturing any ADC based on 6-azido-GalNAc incorporation would require the availability of multigram to kilogram quantities of UDP-6-azidosugar, not accessible by a known route.

With regard to 6-azido-GalNAc, several fully synthetic strategies have been reported and are disclosed herein. Without exception, introduction of the azido group is achieved by S$_N$2 nucleophilic substitution of a 6-O-sulfonylated derivative of N-protected D-galactosamine. The efficiency of the latter substitution, however, is highly dependent on the specific protective group the 0-3 and 0-4 positions, with a strong reaction rate correlation at in the order diacetyl <isopropylidene <no protection. The consequence of such strong structure-reactivity relationships is that nucleophilic substitution is either slow, requiring lengthy treatment with azide anion at elevated conditions (e.g. 5 d at 100° C.), and low-yielding (<50%), or a lengthy synthetic route is required to achieve at a properly protected galactosamine derivative (up to 10 synthetic steps). In addition, the particular synthetic route chosen may require expensive, odorous and/or dangerous reagents (e.g. thiophenol, triflic anhydride, 15-crown-5, ceric ammonium nitrate) and eventually require cumbersome amine protective group exchange and anomeric deprotection protocols (e.g. phthalimide removal with hydrazine or allyl removal with palladium reagents). Finally, one procedure reported by Hang et al., *PNAS* 2003, 100, 14846, incorporated by reference reports a quick procedure (three synthetic steps) from GalNAc to 6-azido-GalNAc, however, due to the lack of selectivity in the tosylation step, the desired product is obtained as a near intractable mixture of components, thereby requiring extensive and cumbersome silica gel purification. From a manufacturing perspective, neither of these features is desirable, thus necessitating a short and high-yielding route towards a suitably protected 6-azido-GalNAc derivative (formally 6-azido-6-deoxy-N-acetyl-D-galactosamine).

The second challenge to obtain UDP 6-azido-GalNAc at a suitable scale lies in the cumbersome subsequent steps, i.e. the conversion of 6-azido-GalNAc monosaccharide into the uridine diphosphate derivative (UDP). Although various routes can be considered, typically this involves first phosphorylation at the anomeric position, followed by a coupling step with UMP, either step of which can be performed chemically or with enzymatic catalysis. With regard to chemical phosphorylation of the anomeric position, neat phosphoric acid has been applied for example by MacDonald et al., *J. Org. Chem.* 1966, 31, 513 and Masuko et al., *J. Org. Chem.* 2012, 77, 1449, incorporated by reference, however products are obtained as anomeric α/β mixtures and yields are low (<50%), thus requiring cumbersome purification and substantial late-stage loss of precious material. Alternatively, an anomeric, selectively deprotected, 6-$N_3$-GalNAc derivative may be reacted with a phosphitylating reagent, such as a chlorophosphinate or phosphoramidite, which may be activated for reaction with the anomeric hydroxyl group in the presence of a proton scavenger or mild acid, respectively. Either of these phosphitylating reagents will carry protective groups for removal after the phosphitylation step and subsequent oxidation of the intermediate phosphite triester to phosphate trimester, performed with mCPBA, $H_2O_2$, iodine or other oxidizing agents. Use of phosphoramidite reagent for anomeric phosphorylation is for example demonstrated by Hang et al., *J. Am. Chem. Soc.* 2004, 126, 6, incorporated by reference. Disadvantages of such a route are the high costs and sensitivity of phosphoramidite reagents, while typically the phosphorylation at O-1 will provide a mixture of α-anomeric and β-anomeric forms.

With regard to the coupling step of the sugar-monophosphate with UMP, a known procedure involves the activation of UMP through the nucleoside 5'-phosphoramidates as described by Moffatt et al., *J. Am. Chem. Soc.* 1961, 83, 649, incorporated by reference, and later improved by Wittmann et al., *J. Org. Chem.* 1997, 62, 2144, incorporated by reference, based 1-H-tetrazole activation. One other common strategy for coupling of sugar-1-phosphates and UMP involves the use of carbonylation-type reagents, as for example reported by Illarionov et al., *Russ. Chem. Bull.* 2001, 50, 1303 and Loureiro Morais, *Can. J. Chem.* 2006, 84, 587, incorporated by reference. Alternatively, the sugar-1-phoshate may be coupled with a morpholidate derivative of UMP, as reported by Moffatt et al., *J. Am. Chem. Soc.* 1958, 80, 3756, incorporated by reference, optionally in the presence of 1-H-tetrazole, as reported by Wittmann et al., *J. Org. Chem.* 1997, 62, 2144, incorporated by reference. Coupling of sugar-1-phosphate with an imidazolide-activated NMP, as reviewed in Wagner et al., *Nat. Prod. Rep.* 2009, 26, 1172, incorporated by reference, may be particularly effective. However, despite the availability of a plethora of methods, there is no commonly accepted, high-yielding and scalable route to obtain UDP derivatives of monosaccharides, in particular N-acetylated hexosamines. Moreover, the presence of the 6-azido group in UDP 6-azido-N-acetyl-hexosamines further limits the choice of conditions, due to its electron-withdrawing character and the incompatibility with a range of (reducing) conditions. Therefore, an improved protocol for manufacturing of UDP 6-azido-6-deoxy-N-acetyl-hexosamines such as UDP 6-azido-6-deoxy-GalNAc and UDP 6-azido-6-deoxy-GlcNAc is highly needed.

SUMMARY OF THE INVENTION

The inventors have developed a process for the synthesis of 6-azido-6-deoxy-2-N-acetyl-monosaccharide-nucleoside diphosphate, in particular 6-azido-6-deoxy-2-N-acetyl-D-galactosamine-nucleoside diphosphate or 6-azido-6-deoxy-2-N-acetyl-D-glucosamine-nucleoside diphosphate and different salt forms thereof. This target compound of the present invention is herein represented by structure (IX):

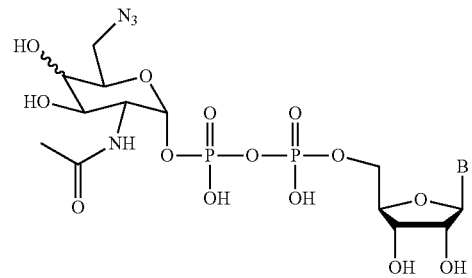

Herein, B is a nucleobase.

The present invention concerns processes for the (partial) synthesis of the target compound according to the invention, as well as key intermediates in these processes. The invention also concerns several approaches towards the total synthesis of the compound having structure (IX).

The synthetic methods according to the invention are characterized by being highly efficient and high yielding. In particular, the drawbacks of the prior art processes as identified above are obviated. With the present invention, 6-azido-6-deoxy-2-N-acetyl-D-galactosamine-nucleoside diphosphate and 6-azido-6-deoxy-2-N-acetyl-D-glucosamine-nucleoside diphosphate have become readily available to the skilled practitioner.

DETAILED DESCRIPTION

Definitions

The verb "to comprise", and its conjugations, as used in this description and in the claims is used in its non-limiting sense to mean that items following the word are included, but items not specifically mentioned are not excluded. In addition, reference to an element by the indefinite article "a" or "an" does not exclude the possibility that more than one of the elements is present, unless the context clearly requires that there is one and only one of the elements. The indefinite article "a" or "an" thus usually means "at least one".

The compounds disclosed in this description and in the claims may comprise one or more asymmetric centres, and different diastereomers and/or enantiomers may exist of the compounds. The description of any compound in this description and in the claims is meant to include all diastereomers, and mixtures thereof, unless stated otherwise. In addition, the description of any compound in this description and in the claims is meant to include both the individual enantiomers, as well as any mixture, racemic or otherwise, of the enantiomers, unless stated otherwise. When the structure of a compound is depicted as a specific enantiomer, it is to be understood that the invention of the present application is not limited to that specific enantiomer.

The compounds may occur in different tautomeric forms. The compounds according to the invention are meant to include all tautomeric forms, unless stated otherwise. When the structure of a compound is depicted as a specific tautomer, it is to be understood that the invention of the present application is not limited to that specific tautomer.

The compounds according to the invention may exist in salt form, which are also covered by the present invention. The salt is typically a pharmaceutically acceptable salt, containing a pharmaceutically acceptable anion. The term "salt thereof" means a compound formed when an acidic proton, typically a proton of an acid, is replaced by a cation, such as a metal cation or an organic cation and the like. Where applicable, the salt is a pharmaceutically acceptable salt, although this is not required for salts that are not intended for administration to a patient. For example, in a salt of a compound the compound may be protonated by an inorganic or organic acid to form a cation, with the conjugate base of the inorganic or organic acid as the anionic component of the salt. Pharmaceutically accepted salts are acceptable for administration to a patient, such as a mammal (salts with counter ions having acceptable mammalian safety for a given dosage regime). Such salts may be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions known in the art and include, for example, sodium, potassium, calcium, magnesium, ammonium, alkylammonium, dialkylammonium, trialkylammonium, tetraalkylammonium, etc., and when the molecule contains a basic functionality, salts of organic or inorganic acids, such as hydrochloride, hydrobromide, formate, tartrate, besylate, mesylate, acetate, maleate, oxalate, etc. In a preferred embodiment, the counter-ion of the salts according to the invention are selected from trialkylammonium, ammonium and sodium, more preferably from ammonium and sodium, most preferably sodium.

The term "monosaccharide" is herein used in its normal scientific meaning and refers to an oxygen-containing heterocycle resulting from intramolecular hemiacetal formation upon cyclisation of a chain of 5-9 (hydroxylated) carbon atoms, most commonly containing five carbon atoms (pentoses) or six carbon atoms (hexose). Typical monosaccharides are glucose (Glu), galactose (Gal) and mannose (Man).

The term "hexosamine" is herein used as a monosaccharide that has an amino group in position 2 of the carbon chain. Typical hexosamines are D-galactosamine (GalNH$_2$) and D-glucosamine (GlcNH$_2$). The hexosamine may be acetylated. Typical acetylated hexosamines are N-acetyl-D-glucosamine (GlcNAc) and N-acetyl-D-galactosamine (GalNAc).

The term "substantial" or "substantially" is herein defined as a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

Alkyl groups may be substituted and unsubstituted, may be linear or branched, may optionally contain a cyclic moiety. Optionally, the alkyl groups are substituted by one or more substituents. Examples of suitable alkyl groups include, but are not limited to, methyl, ethyl, propyl, 2-propyl, t-butyl and the like. In the context of the present invention, in particular in the definition of R$^1$ and R$^2$, it is preferred that alkyl is C$_{1-6}$ alkyl, more preferably C$_{1-2}$ alkyl, most preferably methyl.

Aryl groups comprise may include monocyclic, bicyclic and polycyclic structures. Optionally, the aryl groups may be substituted. Examples of aryl groups include groups such as for example phenyl, naphthyl, anthracyl and the like. In the context of the present invention, in particular in the definition of R$^1$ and R$^2$, it is preferred that aryl is C$_{5-6}$ aryl, most preferably phenyl.

Arylalkyl groups contain an alkyl (or alkylene) moiety and an aryl (or arylene) moiety and may be viewed as a substituted alkyl moiety or a substituted aryl moiety. The aryl (or arylene) moiety may include monocyclic and bicyclic structures. Optionally, the arylalkyl groups may be substituted by one or more substituents. An arylalkyl group is for example benzyl, naphthylmethyl, 4-t-butylphenyl and the like. In the context of the present invention, in particular in the definition of R$^1$ and R$^2$, it is preferred that arylalkyl is C$_{6-12}$ arylalkyl, more preferably C$_{6-8}$ arylalkyl, most preferably benzyl.

THE INVENTION

The inventors have developed an improved, high yielding, process for the synthesis of 6-azido-2-N-acetyl-hexosamine-nucleoside diphosphates or a salt thereof, in particular wherein the hexosamine is galactosamine or glucosamine and the corresponding acetylated hexosamines are N-acetyl-galactosamine (GalNAc) or N-acetylglucosamine (GlcNAc). This target compound of the present invention is herein represented by structure (IX):

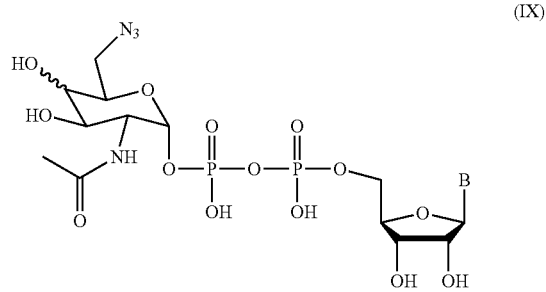

Herein, B is a nucleobase. Although any nucleobase may be used, B is preferably a pyrimidine nucleobase, most preferably B is uracil.

Herein, the wiggly bond at the carbon atom at position 4 of the monosaccharide moiety can either be axial (galactose configuration) or equatorial (glucose configuration). Both products can readily be obtained by the processes according to the present invention. In a preferred embodiment, the product with galactose configuration is prepared, as that compound (GalNAc) potentially finds application in its transfer onto the terminal GlcNAc moiety of the glycan of glycoproteins, which reaction is readily performed in the presence of a mutant galactosyltransferase (GalT) or an N-acetylgalactosaminyltransferase (GalNAcT) enzyme. This application of the compounds of the present invention is known in the art, e.g. from Ramakrishnan et al, *J. Biol. Chem.* 2002, 277, 20833 and WO 2016170186, which is incorporated herein in its entirety.

[A] Reaction Steps

The processes according to the various aspects of the invention involve one or more of the steps (a), (b), (c), (d), (e), (f), (g), (i), (j), (i1), (j1), (x1), (x2), (x3), (x4), (y1), (y2) and (z). These steps are defined here below.

[A.1] Step (a)

In the processes according to the present invention, step (a) is the conversion of N-acetylglucosamine or N-acetyl-galactosamine into a 1,3-di-acylated compound having structure (II).

Step (a) is typically performed by introduction of a 4,6-benzylidene group, then acylation of the remaining two hydroxyl groups in position 1 and 3 of the monosaccharide, followed by removal of the benzylidene group at positions 4 and 6 by acid hydrolysis or hydrogenation. These two hydroxyl groups are thus unprotected, such that compound (II) may also be referred to as a diol. The reaction scheme corresponding to step (a) is as follows:

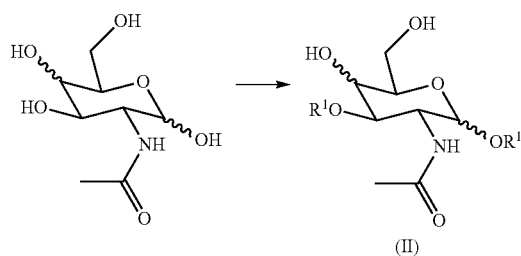

In a preferred embodiment, the reaction scheme corresponding to step (a) is as follows:

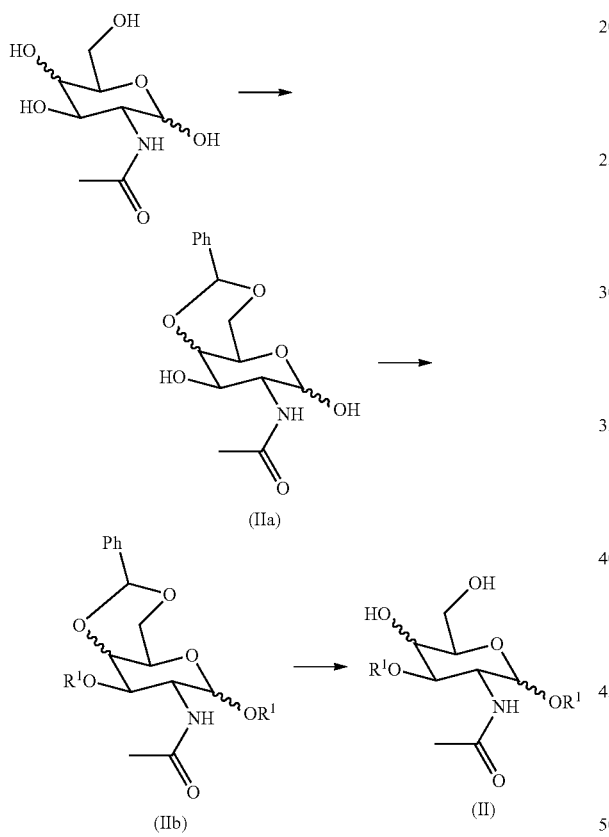

Benzylidene protection of 2-N-acetyl-monosaccharides is a procedure that is well-known in the art, typically involving treatment of the 2-N-acetyl-monosaccharide in a polar, aprotic solvent with benzaldehyde (or a substituted or acetal form thereof) in the presence of acid, as for example described by Yule et al., *Tetrahedr. Lett.*, 36, 1995, 6839, incorporated by reference. Acylation of the remaining alcohol functions in positions 1 and 3 is a procedure well-known in the art. Also removal of benzylidene with acidic hydrolysis or hydrogenation are procedures well-known in the art, as for example described by Jiaang et al., *Synlett*, 2000, 6, 797-800, and Nishimura et al., *Angew. Chem. Int. Ed.*, 2012, 51, 3386-3390, incorporated by reference. Typically, the reactions of step (a) are performed by treatment of monosaccharide with benzaldehyde (or an acetal derivative) with catalytic sulfonic acid (p-TsOH or CSA) in a polar, aprotic solvent like DMF or acetonitrile, next step acylation can be performed in pyridine by treatment with an acid anhydride or in a non-basic organic solvent (e.g. dichloromethane, acetonitrile, ethyl acetate) by treatment with an acid chloride in the presence of a tertiary amine (e.g. triethylamine or DIPEA), finally removal of benzylidene can be performed by acid hydrolysis in aqueous acid or hydrogenation with Pd—C in a suitable solvent (e.g. MeOH, i-PrOH or THF). The compound of structure (II) may be used as such for the next step, or may be purified and/or isolated by means known in the art.

$R^1$ represents the acyl groups that are introduced in step (a). $R^1$ is independently selected from optionally substituted C(O)-alkyl, C(O)-aryl and C(O)-arylalkyl. In one embodiment, $R^1$ is selected from C(O)-alkyl, C(O)-aryl and C(O)-arylalkyl. Given the reaction conditions, both occurrences of $R^1$ are typically the same. In a preferred embodiment, each occurrence of $R^1$ is C(O)Me, C(O)tBu, C(O)Ph or C(O)CH$_2$Ph. Most preferably, each occurrence of $R^1$ is C(O)Me, in which case "acylated" may be referred to as "acetylated". This definition of $R^1$ applies to all aspects of the present invention. In some aspects, $R^1$ may additionally be hydrogen.

[A.2] Step (b)

In the processes according to the present invention, step (b) is the reaction the diol having structure (II) with a sulfitylating agent to form a cyclic sulfite having structure (IIIa). The reaction scheme corresponding to step (b) is as follows:

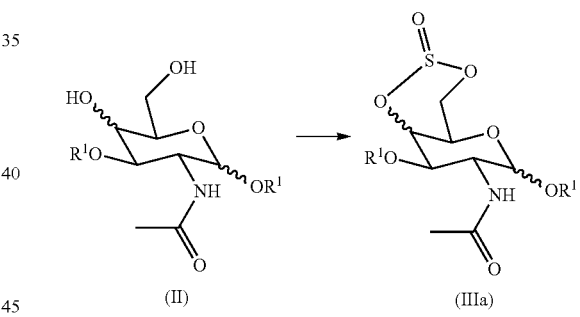

The formation of sulfite compounds from diols is well-known in the art, e.g. from Megia-Fernandez, *Curr. Org. Chem.* 2010, 14, 401, which is incorporated herein in its entirety. Typically, the reaction of step (b) is performed by treatment of a diol with thionyl chloride and tertiary base (e.g. triethylamine or DIPEA) in dichloromethane or ethyl acetate. Sulfitylating agents are known in the art and refer to compounds capable of introducing a sulfite moiety. In a preferred embodiment, the sulfitylating agent is a thionyl halide or 1,1'-thionylimidazole, preferably thionyl chloride. The diol having structure (II) is preferably prepared from N-acetyl-2-glucosamine (GlcNAc) or N-acetyl-2-galactosamine (GalNAc), most preferably obtained according to step (a) as defined above.

The compound of structure (IIIa) may be used as such for the next step, or may be purified and/or isolated by means known in the art.

[A.3] Step (c)

In the processes according to the present invention, step (c) is the reaction of cyclic sulfite having structure (IIIa) with an oxidizing agent to form a cyclic sulfate having structure (IIIb). The reaction scheme corresponding to step (c) is as follows:

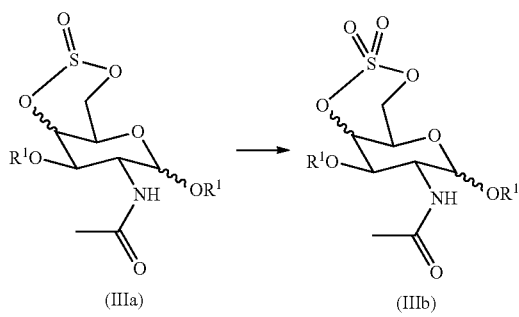

(IIIa)          (IIIb)

The oxidation of sulfite compounds to sulfate compounds is well-known in the art, e.g. from Megia-Fernandez, *Curr. Org. Chem.* 2010, 14, 401, which is incorporated herein in its entirety. Typically, the reaction of step (c) is performed by treatment of a crude cyclic sulfite with a strong oxidizing agent (e.g. m-CPBA, $MnO_2$, $KMnO_4$ TEMPO/NaOCl, $H_2O_2$, $RuO_4$) in dichloromethane, THF, AcOH or acetonitrile. Suitable oxidizing agents are known in the art and are typically selected from organic oxidizing agents and inorganic oxidizing agents. In a preferred embodiment, the oxidizing agent is an inorganic agent, more preferably the oxidizing agent is $RuO_4$. The oxidizing agent may be regenerated in situ, e.g. by addition of a catalytic amount of $RuCl_3$ and a stoichiometric amount of $NaIO_4$.

The compound of structure (IIIb) may be used as such for the next step, or may be purified and/or isolated by means known in the art.

[A.4] Step (d)

In the processes according to the present invention, step (d) is the reaction of the cyclic sulfate having structure (IIIb) with an inorganic azide (i.e. $N_3^-$ anion) to form the 6-azido-6-deoxy monosaccharide having structure (I). The reaction scheme corresponding to step (d) is as follows:

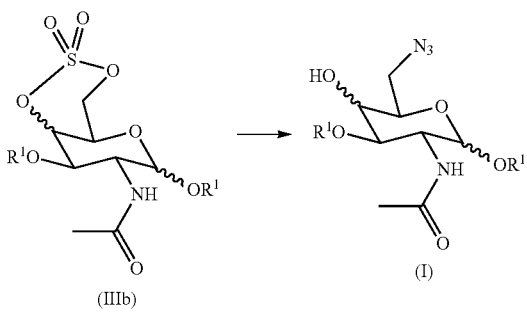

(IIIb)          (I)

The introduction of azido moieties by nucleophilic opening of sulfates is well-known in the art, e.g. from Megia-Fernandez, *Curr. Org. Chem.* 2010, 14, 401 and van der Klein et al., *J. Carbohydr. Chem.* 1992, 11, 837, which is incorporated herein in its entirety. Typically, the reaction of step (d) is performed by stirring the cyclic sulfate with an azide in a polar solvent, such as DMF, THF or acetonitrile, preferably DMF. The reaction may be accelerated by performing at elevated temperature (50-80° C.). The sulfate monoester formed after opening is typically hydrolysed by short treatment (1 h) with catalytic Brønsted acid, e.g. sulfuric acid. Suitable inorganic azides are known in the art and are typically selected from sodium azide, lithium azide or tetrabutylammonium azide. In a preferred embodiment, the inorganic azide is sodium azide.

The compound of structure (I) may be used as such for the next step, or may be purified and/or isolated by means known in the art.

The compound of structure (I) is preferably further converted in a 6-azido-2-N-acetyl-monosaccharide-nucleoside diphosphate having structure (IX) or a salt thereof. Such conversion may be accomplished in any suitable way. Preferably, this conversion involves conversion of the 6-azido-6-deoxy monosaccharide compound having structure (I) into a 1-monophosphate monosaccharide compound, which is reacted with a nucleoside monophosphate to form the compound having structure (IX). Such a reaction sequence involves a deprotecting step, either before or after reaction of the 1-monophosphate monosaccharide compound with the nucleoside monophosphate.

In a preferred embodiment, the conversion of the compounds of structure (I) into the compound of structure (IX) is performed by one of the following reaction sequences:
  Steps (e), (f), (g), (i), and (f);
  Steps (e), (f), (g), (1), and (i1);
  Steps (e), (x1), (x2), (x3), (x4), (i), and optionally (j);
  Steps (e), (x1), (x2), (x3), (x4), (1), (i1);
  Steps (y1), (y2), and (i).
Each of these steps is further defined here below.

[A.5] Step (e)

In the processes according to the present invention, step (e) is the protection of the 6-azido-6-deoxy monosaccharide having structure (I) to form per-acylated 6-azido-6-deoxy monosaccharide compound having structure (VI). The reaction scheme corresponding to step (e) is as follows:

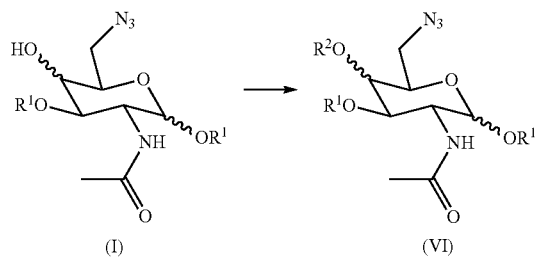

(I)          (VI)

The introduction of acyl moieties is well-known in the art. Typically, the reaction of step (e) is performed by treatment of an alcohol with an activated form of an acid, such as acid anhydride in pyridine, with an acid halide in dichloromethane in the presence of a tertiary base, e.g. triethylamine, or by in situ activation of an acid, e.g. with a carbodiimide reagent. The compound of structure (VI) may be used as such for the next step, or may be purified by means known in the art.

$R^2$ represents the acyl group that is introduced in step (e). $R^2$ is selected from optionally substituted C(O)-alkyl, C(O)-aryl and C(O)-arylalkyl. In one embodiment, $R^2$ is selected from C(O)-alkyl, C(O)-aryl and C(O)-arylalkyl. In a preferred embodiment, $R^2$ is C(O)Me, C(O)tBu, C(O)Ph or C(O)$CH_2$Ph. Most preferably, $R^2$ is C(O)Me, in which case "acylated" may be referred to as "acetylated". $R^1$ and $R^2$ may be the same or different, which is irrelevant for further conversion of the compound having structure (IV) in the methods of the present invention. This definition of $R^2$ applies to all aspects of the present invention. In some aspects, R² may additionally be hydrogen.

[A.6] Step (f)

In the processes according to the present invention, step (f) is the conversion of the compound having structure (VI) in the presence of one or more Lewis acids into oxazoline compound having structure (VII). The reaction scheme corresponding to step (f) is as follows:

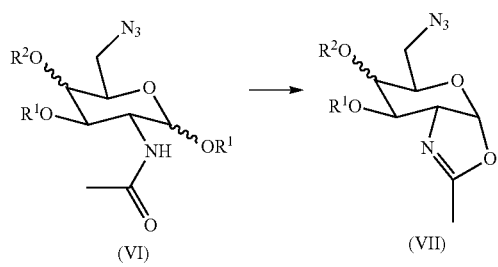

(VI)  (VII)

The formation of an oxazoline ring is well-known in the art, e.g. from Matta et al., *Carbohydr. Res.* 1973, 26, 215 and Srivastava et al. *Carbohydr. Res.* 1982, 103, 286 and Nakabayashi et al., *Carbohydr. Res.* 1986, 150, C7 and Colon et al., *Tetrahedron Lett.* 1991, 32, 4447 and Rising et al., *Carbohydr. Res.* 2006, 341, 1574, all of which are incorporated herein in its entirety. Typically, the reaction of step (f) is performed by treatment of a peracylated hexosamine monosaccharide with a Lewis acid in a chlorinated solvent, such as dichloromethane, dichloroethane or chloroform. Suitable Lewis acids are known in the art and are typically selected from ferric(III) chloride, tin(IV) chloride, boron trifluoride, zinc(II) iodide trimethylsilyl chloride, trimethylsilyl bromide and trimethylsilyl triflate, or a combination thereof. In a preferred embodiment, the Lewis acid is trimethylsilyl triflate or a combination of BF₃ (e.g. BF₃ etherate) and a trimethylsilyl halide (e.g. TMSBr). Alternatively, oxazoline formation can also be achieved from anomerically deprotected acetylated hexosamines by treatment with a chloroformamidinium reagent, as for example reported by Noguchi et al., *J. Org. Chem.* 2009, 74, 2210, incorporated by reference.

The compound of structure (VII) may be used as such for the next step, or may be purified and/or isolated by means known in the art.

[A.7] Step (g)

In the processes according to the present invention, step (g) is the reaction of the compound having structure (VII) with phosphoric acid to form the 1-monophosphate monosaccharide compound having structure (Va). The reaction scheme corresponding to step (g) is as follows:

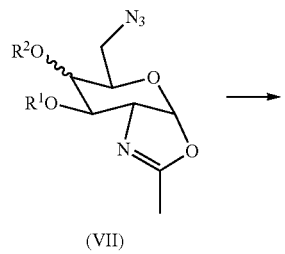

(VII)

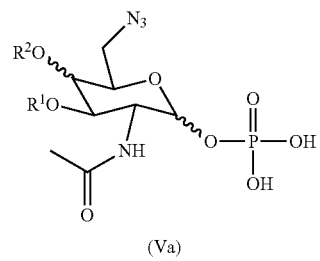

(Va)

The formation of a monophosphate monosaccharide from a peracylated hexosamine is well-known in the art, e.g. from MacDonald et al., *J. Org. Chem.* 1966, 31, 513 and Masuko et al., *J. Org. Chem.* 2012, 77, 1449, which is incorporated herein in its entirety. Typically, the reaction of step (g) is performed by treatment of the peracylated hexosamine with neat phosphoric acid at a temperature of 0-120° C., preferably 20-90° C., more preferably 40-80° C., more preferably 60-80° C. In contrast, conversion of oxazolines to anomeric phosphates under these conditions (neat phosphoric acid) has not been earlier reported. Typically, conversion of oxazoles is performed by treatment with 1-100 equivalents, preferably 2-8 equivalents, most preferably 5-7 equivalents phosphoric acid at a temperature of 0-120° C., preferably 20-90° C., more preferably 40-80° C., more preferably 60-80° C. in DMF. Similarly, conversion of oxazolines to anomeric phosphates by treatment with phosphoric acid in DMF has not been earlier reported.

The compound of structure (Va) may be used as such for the next step, or may be purified and/or isolated by means known in the art.

[A.8] Step (i)

In the processes according to the present invention, step (i) is the reaction of the compound having structure (Va) with a nucleoside monophosphate into an acylated nucleoside diphosphate having structure (VIII). Thus, the phosphate compound of structure (Va) is coupled to the nucleoside monophosphate, thus forming a diphosphate moiety. Acylation of the nucleoside monophosphate at the 2' and 3' positions (R⁴) may take place during the process of reaction with (Va), for example carbonylation may take place upon activation with 1,1'-carbonyldi-imidazool (CDI). Alternatively, the 2' and 3' positions of the nucleoside monophosphate may be acylated before coupling to (Va), for example by acetylation or benzoylation. The reaction scheme corresponding to step (i) is as follows:

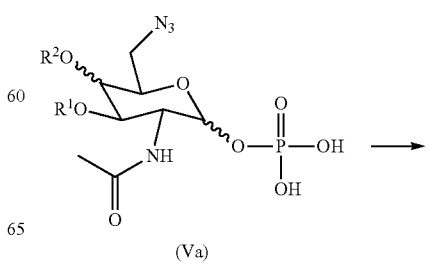

(Va)

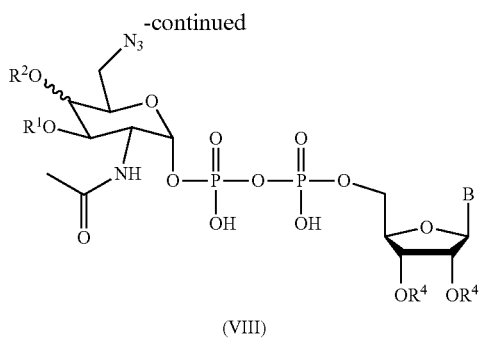

(VIII)

In a preferred embodiment, the reaction scheme corresponding to step (i) is as follows:

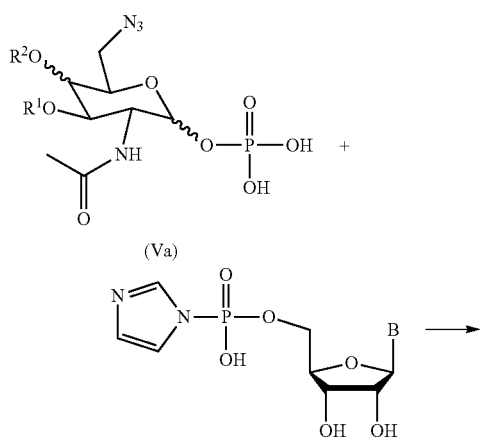

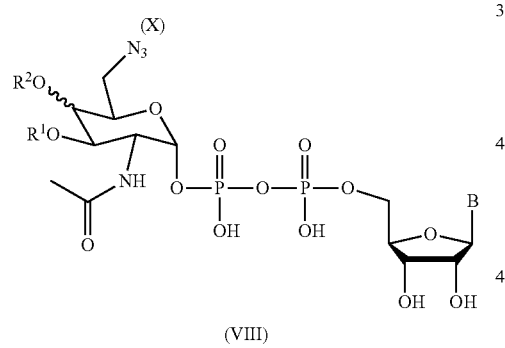

(VIII)

The formation of a nucleoside diphosphate monosaccharide is well-known in the art, and may be achieved via a large number of synthetic strategies, e.g. summarized in Ahmadipour et al., *Carbohydr. Res.* 2017, 451, 95, which is incorporated herein in its entirety. Most commonly, the reaction of step (i) is performed by in situ activation of a mixture of the sugar-1-phosphate and UMP, e.g. with a carbonylation reagent like carbonyl diimidazole (CDI), as reported by Illarionov et al., *Russ. Chem. Bull.* 2001, 50, 1303 and Loureiro Morais, *Can. J. Chem.* 2006, 84, 587, incorporated by reference. Alternatively, the sugar-1-phosphate may be coupled with a morpholidate derivative of UMP, as reported by Moffatt et al., *J. Am. Chem. Soc.* 1958, 80, 3756, incorporated by reference, optionally in the presence of 1-H-tetrazole, as reported by Wittmann et al., *J. Org. Chem.* 1997, 62, 2144, or by using sulfonyl imidazolium salts as reported by Mohamady et al., *Curr. Prot. Nucl. Acid Chem.* 2012, DOI: 10.1002/0471142700.nc3111s51, incorporated by reference, or in the presence of 4,5-dicyanoimidazole (DCI) as reported by Vargeese et al., *Nucleic Acids Res.* 1998, 26, 1046, incorporated by reference. Coupling of sugar-1-phosphate with an imidazolide-activated NMP under the action of $ZnCl_2$ or $MgCl_2$, as reported by Dabrowski-Tumanski, *Eur. J. Org. Chem.* 2013, 11, 2147, incorporated by reference, may be particularly effective. Alternatively, an enzymatic approach may be taken, such as by reaction of the compound of structure (Va) with a nucleoside triphosphate in the presence of pyrophosphatase (PPA), which converts the nucleoside triphosphate into a nucleoside monophosphate, and an pyrophosphorylase (e.g. UDP-Gal-NAc pyrophosphorylase AGX1), which transfers the nucleoside monophosphate to sugar derivative (Va), see e.g. Guan et al., *Chem. Eur. J.* 2010, 16, 13343-13345, incorporated by reference. The compound of structure (VIII) may be used as such for the next step, or may be purified and/or isolated by means known in the art.

$R^4$ represents the groups at the 2' and 3' positions of the ribosyl ring of the nucleoside moiety. Optimal results have been obtained with both occurrences of $R^4$ being hydrogen, and with both occurrences of $R^4$ being joined together via a carbonyl moiety, thus forming a carbonate ester with the two oxygen atoms connected to both $R^4$ groups. The most efficient synthesis and highest yields were obtained with both occurrences of $R^4$ being hydrogen, which is thus preferred in the context of the present invention.

[A.9] Step (j)

In the processes according to the present invention, step (j) is the deprotection of the acylated nucleoside diphosphate having structure (VIII) to obtain nucleoside diphosphate having structure (IX), or salt thereof. The reaction scheme corresponding to step 6) is as follows:

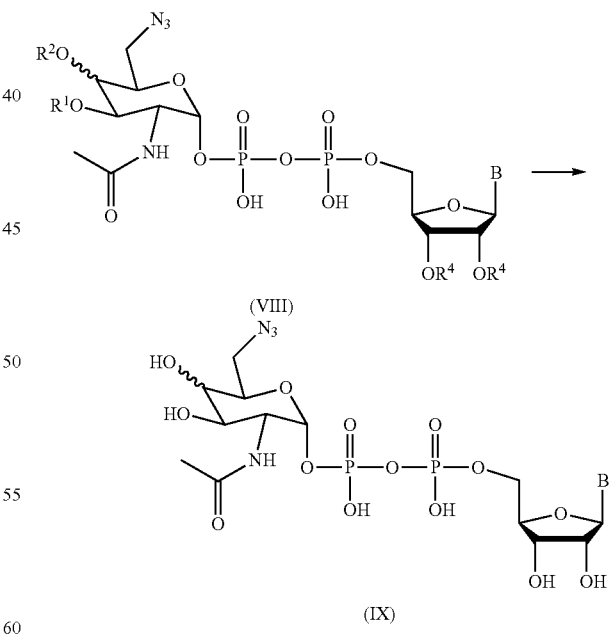

The deprotection of an acylated compound is well-known in the art. A large number of reaction conditions are suitable thereto, for example the reaction of step (j) is performed by treatment of the acylated compound with a (catalytic) amount of sodium methoxide in methanol or by treatment with a mixture of $Et_3N$, MeOH and $H_2O$. The compound of structure (IX) may be used as such for the next step, or may be purified and/or isolated by means known in the art.

Herein, B is a nucleobase. Although any nucleobase may be used, B is preferably a pyrimidine nucleobase, most preferably B is uracil.

In the processes according to the present invention, the coupling of step (i) and the deprotection of step 6) can also be performed the other way around, without any negative affect on the process efficacy and yields. These reactions are referred to herein as step (i1) and step (j1).

[A.10] Step (j1)

In the processes according to the present invention, step 61) is the deprotection of the acylated 1-monophosphate monosaccharide having structure (Va) to obtain 1-monophosphate monosaccharide having structure (Vb). The reaction scheme corresponding to step 61) is as follows:

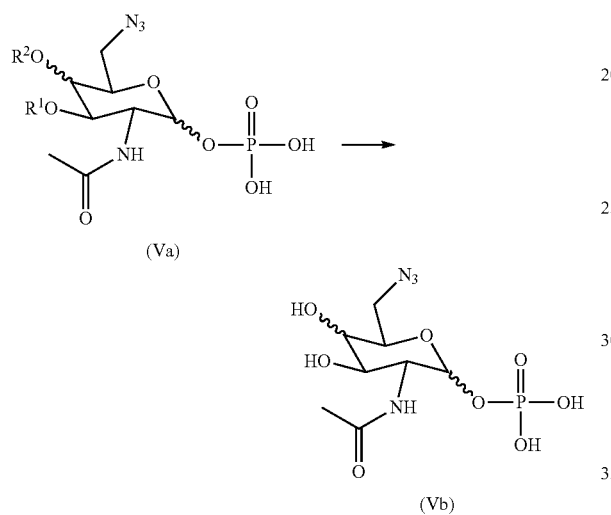

The deprotection of an acylated compound is well-known in the art. A large number of reaction conditions are suitable thereto, for example the reaction of step 6) is performed by treatment of the acylated compound with a (catalytic) amount of sodium methoxide in methanol or by triethylamine in a water/methanol mixture. The compound of structure (Vb) may be used as such for the next step, or may be purified and/or isolated by means known in the art.

[A.11] Step (i1)

In the processes according to the present invention, step (i1) is the reaction of the compound having structure (Vb) with a nucleoside monophosphate into a nucleoside diphosphate having structure (IX). Thus, the 1-monophosphate monosaccharide compound of structure (Vb) is coupled to the nucleoside monophosphate, thus forming a diphosphate moiety. The reaction scheme corresponding to step (i1) is as follows:

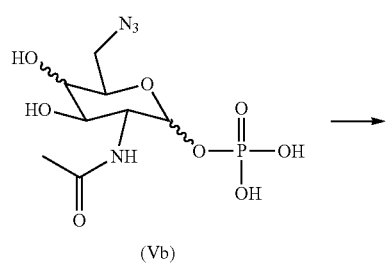

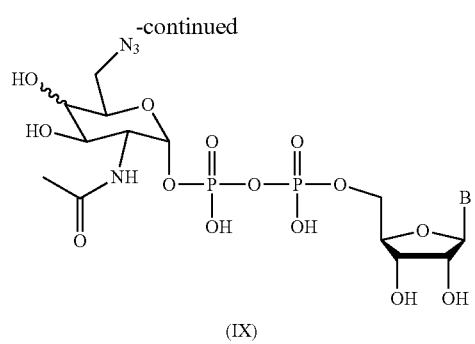

In a preferred embodiment, the reaction scheme corresponding to step (i1) is as follows:

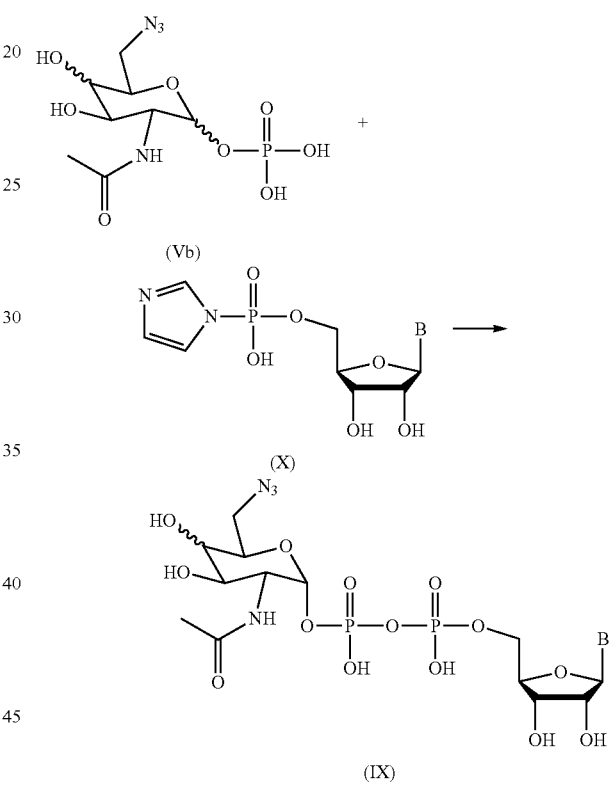

The formation of a nucleoside diphosphate monosaccharide is well-known in the art, and may be achieved via a large number of synthetic strategies, e.g. summarized in Ahmadipour et al., *Carbohydr. Res.* 2017, 451, 95, which is incorporated herein in its entirety. Most commonly, the reaction of step (i1) is performed by in situ activation of a mixture of a sugar-1-phosphate and UMP, e.g. with a carbonylation reagent like carbonyl diimidazole (CDI), as reported by Illarionov et al., *Russ. Chem. Bull.* 2001, 50, 1303 and Loureiro Morais, *Can. J. Chem.* 2006, 84, 587, incorporated by reference. Alternatively, the sugar-1-phoshate may be coupled with a morpholidate derivative of UMP, as reported by Moffatt et al., *J. Am. Chem. Soc.* 1958, 80, 3756, incorporated by reference, optionally in the presence of 1-H-tetrazole, as reported by Wittmann et al., *J. Org. Chem.* 1997, 62, 2144, incorporated by reference, or in the presence of 4,5-dicyanoimidazole (DCI) as reported by Vargeese et al., *Nucleic Acids Res.* 1998, 26, 1046, incorporated by reference. Coupling of sugar-1-phosphate with an imidazolide-activated NMP, as reviewed in Wagner et al., *Nat. Prod. Rep.* 2009, 26, 1172, incorporated by reference, may be particularly effective. Alternatively, an enzymatic approach may be taken, such as by reaction of the compound of structure (Vb) with a nucleoside triphosphate in the presence of pyrophosphatase (PPA), which converts the nucleoside triphosphate into a nucleoside monophosphate, and an pyrophosphorylase (e.g. UDP-GalNAc pyrophosphorylase AGX1), which transfers the nucleoside monophosphate to sugar derivative (Vb), see e.g. Guan et al., *Chem. Eur. J.* 2010, 16, 13343-13345, incorporated by reference. The compound of structure (IX) may be used as such for the next step, or may be purified and/or isolated by means known in the art.

Herein, B is a nucleobase. Although any nucleobase may be used, B is preferably a pyrimidine nucleobase, most preferably B is uracil.

[A.12] Step (z)

Both step (i) and step (i1) can be performed by reacting the compound having structure (Va) or (Vb) with the nucleoside monophosphate having structure (X). As this is applicable to both steps, this reaction is also independently referred herein as step (z). In the processes according to the present invention, step (z) is the reaction of the compound having structure (V) with a nucleoside monophosphate having structure (X) to form a nucleoside diphosphate having structure (IX). Thus, the phosphate compound of structure (V) is coupled to the nucleoside monophosphate, thus forming a diphosphate moiety. The reaction scheme corresponding to step (z) is as follows:

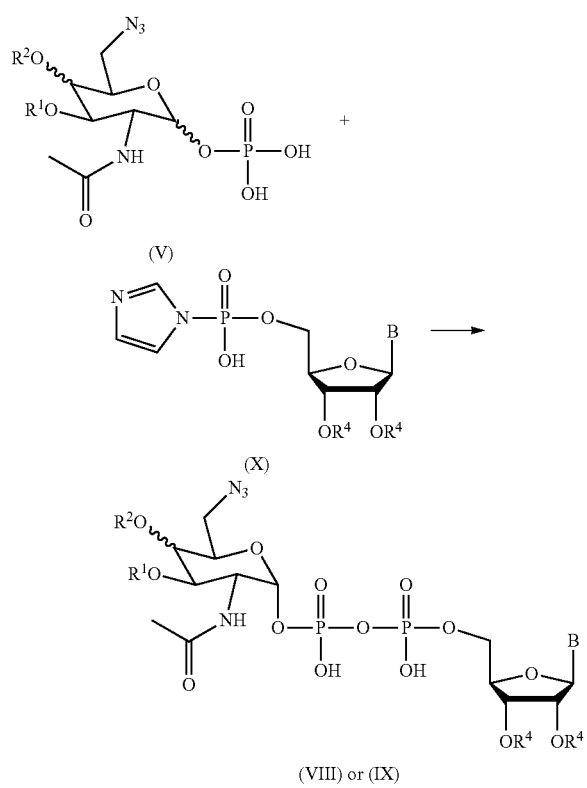

Herein, $R^1$ is selected from optionally substituted C(O)-alkyl, C(O)-aryl and C(O)-arylalkyl, and $R^2$ is selected from optionally substituted C(O)-alkyl, C(O)-aryl and C(O)-arylalkyl, wherein either both $R^1$ and $R^2$ are H (compound (Vb) or (IX)) or none of $R^1$ and $R^2$ is H (compound (Va) or (VIII)). B is a nucleobase. Although any nucleobase may be used, B is preferably a pyrimidine nucleobase, most preferably B is uracil.

$R^4$ represents the groups at the 2' and 3' positions of the ribosyl ring of the nucleoside moiety, and are both hydrogen or both occurrences of $R^4$ are joined together via a carbonyl moiety. Preferably, both occurrences of $R^4$ are hydrogen.

The formation of a nucleoside diphosphate monosaccharide is well-known in the art, and may be achieved via a large number of synthetic strategies, e.g. summarized in Ahmadipour et al., *Carbohydr. Res.* 2017, 451, 95, which is incorporated herein in its entirety. Most commonly, the reaction of step (i) is performed by in situ activation of the sugar-1-phosphate in the presence of UMP, e.g. with a carbonylation reagent like carbonyl diimidazole (CDI), as reported by Illarionov et al., *Russ. Chem. Bull.* 2001, 50, 1303 and Loureiro Morais, *Can. J. Chem.* 2006, 84, 587, incorporated by reference. Alternatively, the sugar-1-phosphate may be coupled with a morpholidate derivative of UMP, as reported by Moffatt et al., *J. Am. Chem. Soc.* 1958, 80, 3756, incorporated by reference, optionally in the presence of 1-H-tetrazole, or by using sulfonyl imidazolium salts as reported by Mohamady et al., *Curr. Prot. Nucl. Acid Chem.* 2012, DOI: 10.1002/0471142700.nc1311s51, incorporated by reference, or in the presence of 4,5-dicyanoimidazole (DCI) as reported by Vargeese et al., *Nucleic Acids Res.* 1998, 26, 1046, incorporated by reference. In one embodiment, step (z) is performed in the presence of an organic base such as 1-methylimidazolium chloride or 1-H-tetrazole, or a Lewis acid such as $MgCl_2$ or $ZnCl_2$. Coupling of sugar-1-phosphate with an imidazolide-activated NMP under the action of $ZnCl_2$ or $MgCl_2$, as reported by Dabrowski-Tumanski, *Eur. J. Org. Chem.* 2013, 11, 2147, as reviewed in Wagner et al., *Nat. Prod. Rep.* 2009, 26, 1172, incorporated by reference, may be particularly effective. The compound of structure (VIII) or (IX) may be used as such for the next step, or may be purified and/or isolated by means known in the art.

In an alternative embodiment, the compound having structure (VI) as obtained in step (e) is not converted into the oxazoline compound having structure (VII) by step (f, but instead is subjected to steps (x1)-(x4) to form the compound having structure (Va). This compound may then be converted into the compound having structure (IX) by steps (i)+(j) or by steps (1)+(i1).

[A.13] Step (x1)

In the processes according to the present invention, step (x1) is the deprotection of the hydroxyl moiety attached to the anomeric carbon of the compound having structure (VI) to form 1-hydroxy-monosaccharide compound having structure (XI). The reaction scheme corresponding to step (x1) is as follows:

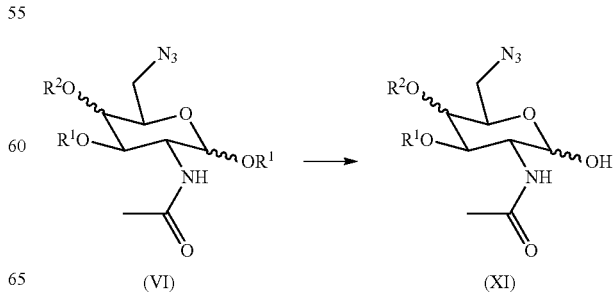

The selective deprotection of anomeric hydroxyl groups from peracylated monosaccharides is well-known in the art, e.g. as reported by Johnsson et al., *Synlett,* 2005, 2939 and Baumik et al., *Aus. J. Chem.* 2003, 56, 909, which is incorporated herein in its entirety. For example, the reaction of step (x1) is performed by treatment of the peracylated monosaccharide with a small molar excess of benzylamine, dimethylamine or hydrazine acetate in an organic solvent like THF or acetonitrile.

The compound of structure (XI) may be used as such for the next step, or may be purified and/or isolated by means known in the art.

[A.14] Step (x2)

In the processes according to the present invention, step (x2) is the conversion of the 1-hydroxy-monosaccharide compound having structure (XI) into the monophosphite diester having structure (XII). The reaction scheme corresponding to step (x2) is as follows:

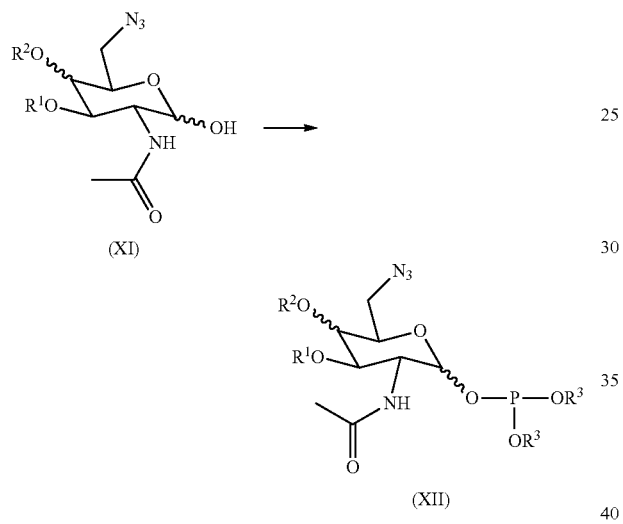

The phosphitylation of hydroxyl groups is well-known in the art, e.g. as summarized in Ahmadipour et al., *Carbohydr. Res.* 2017, 451, 95, which is incorporated herein in its entirety. Typically, the reaction of step (x2) is performed by treatment of anomerically deprotected monosaccharide with a phosphitylating reagent, such as a chlorophosphinate or phosphoramidite, which may be activated for reaction with the anomeric hydroxyl group in the presence of a proton scavenger or mild acid, respectively. The compound of structure (XII) may be used as such for the next step, or may be purified and/or isolated by means known in the art.

Herein, $R^3$ represents the moiety that is attached to both oxygen atoms of the phosphityl diester (i.e. not including the anomeric oxygen atom of the monosaccharide moiety). $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$alkyl, fluorenylmethyl, 2-pyridylethyl, phenyl-$C_{1-2}$-alkyl, wherein phenyl is optionally substituted with one or more halides or a nitro or methoxy group. Herein, phenyl-$C_{1-2}$-alkyl refers to 2-phenylethyl or phenylmethyl. The nitro or methoxy substituent, especially the methoxy substituent, is preferably in the para position. Although $R^3$ can be individually chosen, it is preferred that both moieties of $R^3$ are the same. In case $R^3$ is 2-alkylsulfonylethyl or $CH_2OC(O)$alkyl, it is preferred that alkyl is $C_{1-6}$ alkyl, more preferably $C_{1-2}$ alkyl, most preferably methyl. In case $R^3$ is 2-arylsulfonylethyl, it is preferred that aryl is phenyl. Each of the options of $R^3$ are easily removed in the subsequent step (x4), this deprotection can be optionally be performed concomitant with the deprotection of $R^1$ and $R^3$ in step (j1). Thus, in an especially preferred embodiment, $R^3$ is $CH_2OC(O)$alkyl, wherein alkyl is preferably $C_{1-6}$ alkyl, more preferably $C_{1-2}$ alkyl, most preferably methyl, and steps (x4) and (1) are performed in a single step (in one pot).

[A.15] Step (x3)

In the processes according to the present invention, step (x3) is the oxidation of the monophosphite diester having structure (XII) to form the 1-monophosphate diester having structure (XIII). The reaction scheme corresponding to step (x3) is as follows:

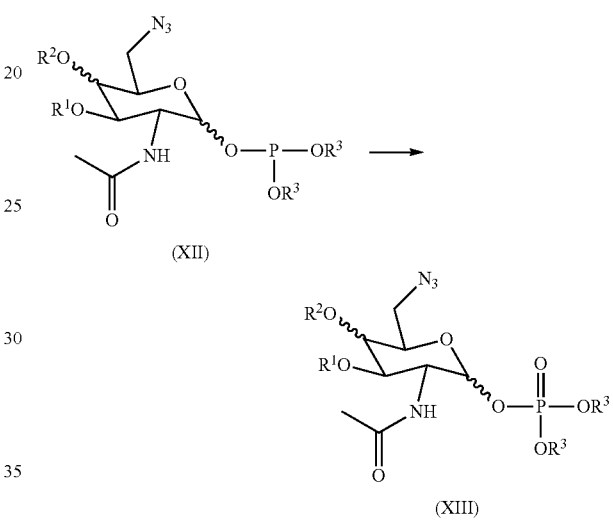

The oxidation of a phosphite moiety is well-known in the art, e.g. summarized in Ahmadipour et al., *Carbohydr. Res.* 2017, 451, 95, which is incorporated herein in its entirety. Typically, the reaction of step (x3) is performed by contacting the phosphite (XII) with an oxidizing agent, such as iodine, m-CPBA, t-BuOOH or $H_2O_2$ in a dichloromethane or acetonitrile solution. The compound of structure (XIII) may be used as such for the next step, or may be purified and/or isolated by means known in the art.

[A.16] Step (x4)

In the processes according to the present invention, step (x4) is the deprotection of the monophosphate diester having structure (XIII) to form the 1-monophosphate monosaccharide having structure (Va). The reaction scheme corresponding to step (x4) is as follows:

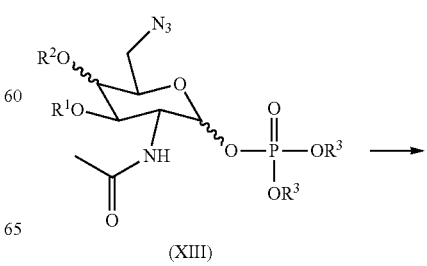

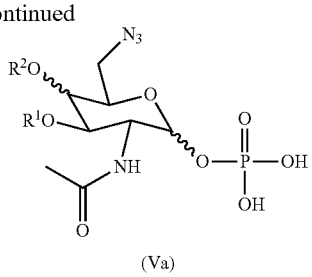

(Va)

Step (x4) may also entail the complete deprotection of compound (XIII), wherein acyl groups $R^1$ and $R^2$ are removed concomitantly with the removal of groups $R^3$. The reaction scheme corresponding to this embodiment of step (x4) is as follows:

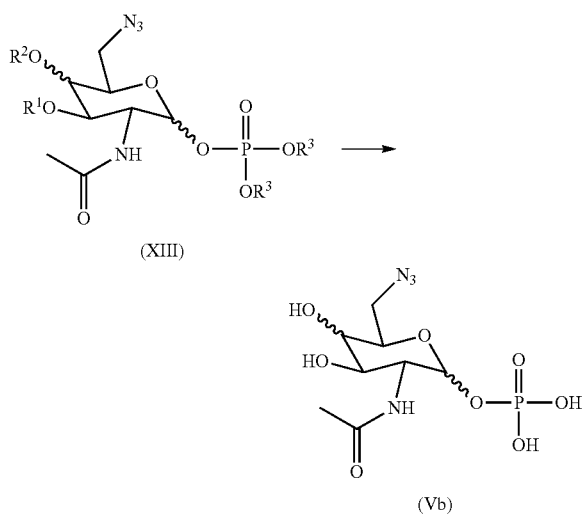

Overall, the reaction scheme for step (x4) is as follows:

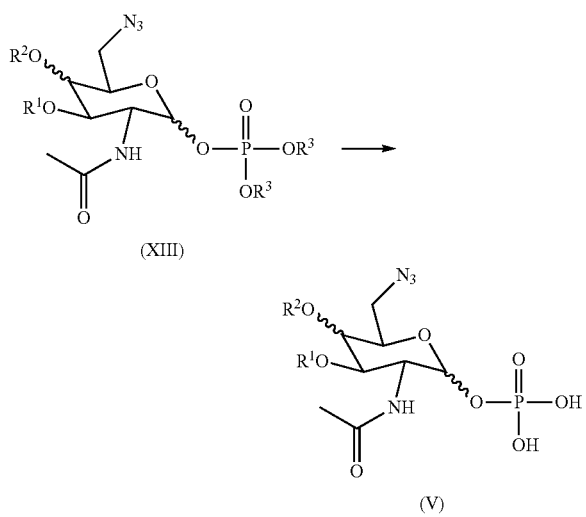

Herein, the following applies:

for compound (XIII): $R^1$ is selected from optionally substituted C(O)-alkyl, C(O)-aryl and C(O)-arylalkyl, and $R^2$ is selected from optionally substituted C(O)-alkyl, optionally substituted C(O)-aryl and C(O)-arylalkyl;

for compound (V), $R^1$ is selected from H and optionally substituted C(O)-alkyl, C(O)-aryl and C(O)-arylalkyl, $R^2$ is selected from H and optionally substituted C(O)-alkyl, C(O)-aryl and C(O)-arylalkyl, wherein either both $R^1$ and $R^2$ are H (compound (Vb)) or none of $R^1$ and $R^2$ is H (compound (Va)).

The deprotection of an acylated monosaccharide is well-known in the art. The compound of structure (Va) or (Vb) may be used as such for the next step, or may be purified and/or isolated by means known in the art.

In an alternative embodiment, the compound having structure (I) as obtained in step (d) is not converted into the triple-acylated compound having structure (VI) by step (e), but instead is subjected to steps (y1)-(y2) to form the compound having structure (Vb). This compound may then be converted into the compound having structure (IX) by step (i1).

[A.17] Step (y1)

In the processes according to the present invention, step (y1) is the deprotection of the 6-azido-6-deoxy monosaccharide having structure (I) to form the 1,3,4-trihydroxy-6-azido-monosaccharide having structure (XIV). The reaction scheme corresponding to step (y1) is as follows:

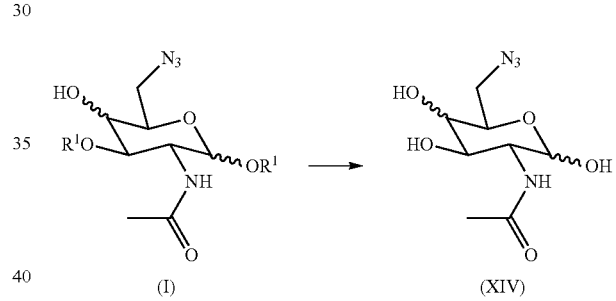

The deprotection of an acylated monosaccharide is well-known in the art. The compound of structure (XIV) may be used as such for the next step, or may be purified and/or isolated by means known in the art.

[A.18] Step (y2)

In the processes according to the present invention, step (y2) is the reaction of 1,3,4-trihydroxy-6-azido-monosaccharide having structure (XIV) phosphate source to form 1-monophosphate monosaccharide compound having structure (Vb). The reaction scheme corresponding to step (y2) is as follows:

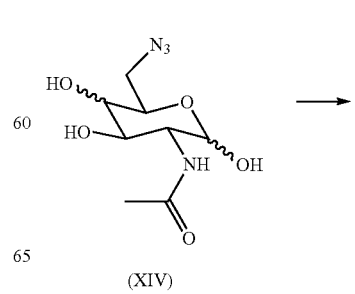

(XIV)

-continued

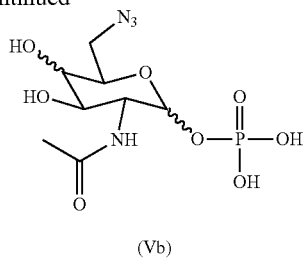

(Vb)

The regioselective phosphorylating of monosaccharides is well-known in the art, e.g. summarized in Bülter et al., *Glycoconj. J.* 1999, 16, 147, which is incorporated herein in its entirety. The reaction of step (y2) is performed in the presence of a phosphorylating enzyme, such as N-acetyl-hexosamine 1-kinase (NahK), see e.g. Cai et al., *Chem. Commun.* 2009, 2944-2946, incorporated by reference. The compound of structure (Vb) may be used as such for the next step, or may be purified and/or isolated by means known in the art. In case the compound of structure (Vb) is converted enzymatically into the nucleoside diphosphate having structure (IX) via step (i1) as next step, the entire reaction sequence can be performed in one-pot, see e.g. Heinzler et al., *Adv. Synth. Catal.* 2019, 361, 4506-4516, incorporated by reference.

[B] Compounds According to the Invention

The inventors have identified some crucial intermediates in the synthesis methods according to the invention. The present invention is also related to these intermediates.

[B.1] Compound (III)

Thus, the invention concerns the cyclic sulfate monosaccharide compound having structure (III):

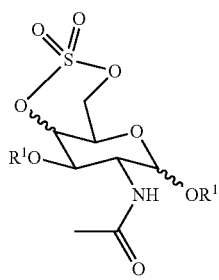

(III)

Herein, $R^1$ is independently selected from optionally substituted C(O)-alkyl, C(O)-aryl and C(O)-arylalkyl. The carbon atoms having a wiggly bond may be in the S-configuration or the R-configuration; all four diastereomers are covered.

$R^1$ represents the acyl groups that are introduced in step (a). $R^1$ is independently selected from optionally substituted C(O)-alkyl, C(O)-aryl and C(O)-arylalkyl. Given the reaction conditions, both occurrences of $R^1$ are typically the same. In a preferred embodiment, each occurrence of $R^1$ is C(O)Me, C(O)tBu, C(O)Ph or C(O)CH$_2$Ph. Most preferably, each occurrence of $R^1$ is C(O)Me.

[B.2] Compound (I)

The invention further concerns the 6-azido-6-deoxy monosaccharide compound having structure (I):

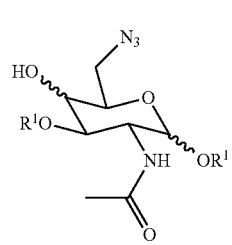

(I)

Herein, $R^1$ is identical as defined for the compound having structure (111). The carbon atoms having a wiggly bond may be in the S-configuration or the R-configuration; all four diastereomers are covered.

[B.3] Compound (VII)

The invention further concerns the oxazoline compound having structure (VII):

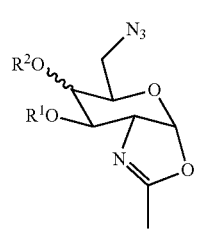

(VII)

Herein, $R^1$ is identical as defined for the compound having structure (111). The carbon atom having a wiggly bond may be in the S-configuration or the R-configuration; both diastereomers are covered. The oxygen of the oxazoline ring, positioned at carbon 1 of the GlcNAc or GalNAc moiety, is exclusively the α-anomer.

$R^2$ represents the acyl group that is introduced in step (e). $R^2$ represents the acyl group that is introduced in step (e). $R^2$ is selected from optionally substituted C(O)-alkyl, C(O)-aryl and C(O)-arylalkyl. In one embodiment, $R^2$ is selected from C(O)-alkyl, C(O)-aryl and C(O)-arylalkyl. In a preferred embodiment, $R^2$ is C(O)Me, C(O)tBu, C(O)Ph or C(O)CH$_2$Ph. Most preferably, $R^2$ is C(O)Me, in which case "acylated" may be referred to as "acetylated". $R^1$ and $R^2$ may be the same or different, which is irrelevant for further conversion of the compound having structure (IV) in the methods of the present invention.

[B.4] Compound (Va)

The invention further concerns a mixture comprising the α-anomeric form and the β-anomeric form of the 6-azido-6-deoxy-1-monophosphate monosaccharide compound having structure (Va), or a salt thereof:

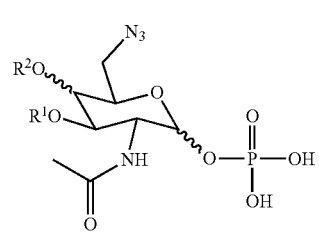

(Va)

Herein, $R^1$ and $R^2$ are identical as defined for the compound having structure (VII). The carbon atoms having a wiggly bond may be in the S-configuration or the R-configuration; all four diastereomers are covered, provided that in the mixture, the molar ratio between the α- and β-anomeric form is in the range of 3/1 to 10/1. Both anomeric forms of compound (Va) present in the mixture may be in salt form.

Known chemical methods to prepare the 6-azido-6-deoxy-1-monophosphate monosaccharide compound having structure (Va) typically yield a mixture of the α- and β-anomeric forms (by chemical conversion, i.e. reaction with a phoshitylating agent such as a phosphoramidite). Although these conventional methods are also suitable in the context of the present invention, it is preferred that phosphate group is introduced via compound (VII), in which case a mixture of the α- and β-anomers is formed containing predominantly but not purely the α-anomer. For the subsequent reactions towards compound (IX), the α-anomeric form is preferred as it is the sole substrate of a transferase enzyme that can be used to incorporate the azide-containing monosaccharide moiety in a glycan chain. To date, obtaining an enantiomeric excess of the α-anomer was only achievable via enzymatic methods. Compound (Va) is obtained as a mixture of isoforms but containing predominantly the α-anomer, via chemical synthesis steps and without the need for enzymatic conversions.

[B.5] Compound (VIII)

The invention further concerns a nucleoside diphosphate having structure (VIII):

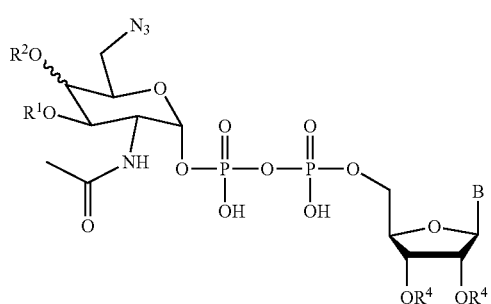

(VIII)

Herein, $R^1$ and $R^2$ are identical as defined for the compound having structure (VII). The carbon atom having a wiggly bond may be in the S-configuration or the R-configuration; both diastereomers are covered.

$R^4$ represents the groups at the 2' and 3' positions of the ribosyl ring of the nucleoside moiety, and are both hydrogen or both occurrences of $R^4$ are joined together via a carbonyl moiety.

Preferably, both occurrences of $R^4$ are hydrogen.

B is a nucleobase. Although any nucleobase may be used, B is preferably a pyrimidine nucleobase, most preferably B is uracil.

[B.6] Compound (XI)

The invention further concerns a 1-hydroxy-monosaccharide compound having structure (XI):

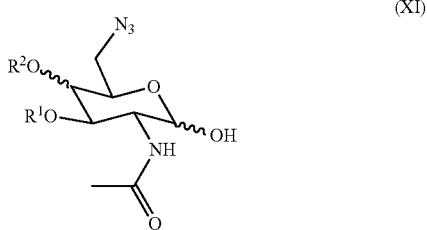

(XI)

Herein, $R^1$ and $R^2$ are identical as defined for the compound having structure (VI). The carbon atoms having a wiggly bond may be in the S-configuration or the R-configuration; all four diastereomers are covered.

[B.7] Compound (XII)

The invention further concerns a phosphite having structure (XII):

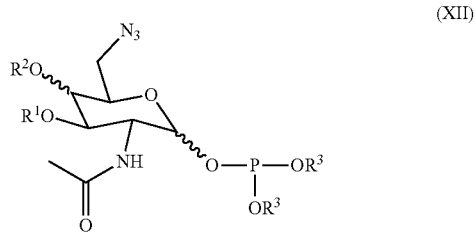

(XII)

Herein, $R^1$ and $R^2$ are identical as defined for the compound having structure (VI). The carbon atoms having a wiggly bond may be in the S-configuration or the R-configuration; all four diastereomers are covered.

Herein, $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$alkyl, fluorenylmethyl, 2-pyridylethyl, phenyl-$C_{1-2}$-alkyl, wherein phenyl is optionally substituted with one or more halides or a nitro or methoxy group.

Herein, phenyl-$C_{1-2}$-alkyl refers to 2-phenylethyl or phenylmethyl. The nitro or methoxy substituent, especially the methoxy substituent, is preferably in the para position. Although $R^3$ can be individually chosen, it is preferred that both moieties of $R^3$ are the same. In case $R^3$ is 2-alkylsulfonylethyl or $CH_2OC(O)$alkyl, it is preferred that alkyl is $C_{1-6}$ alkyl, more preferably $C_{1-2}$ alkyl, most preferably methyl. In case $R^3$ is 2-arylsulfonylethyl, it is preferred that aryl is phenyl. In an especially preferred embodiment, $R^3$ is $CH_2OC(O)$alkyl, wherein alkyl is preferably $C_{1-6}$ alkyl, more preferably $C_{1-2}$ alkyl, most preferably methyl.

[B.8] Compound (XIII)

The invention further concerns a phosphate diester having structure (XIII):

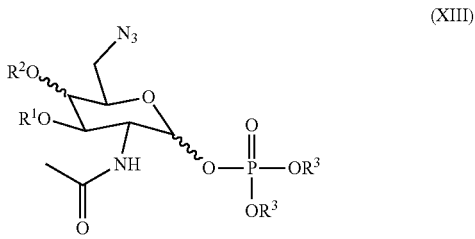

(XIII)

Herein, $R^1$, $R^2$ and $R^3$ are identical as defined for the compound having structure (XII). The carbon atoms having a wiggly bond may be in the S-configuration or the R-configuration; all four diastereomers are covered.

[C] Synthetic processes

In pursuit of the overall aim of the present invention, i.e. providing an efficient synthesis of 6-azido-2-N-acetyl-monosaccharide-nucleoside diphosphate having structure (IX), the inventors have identified some crucial synthetic steps. The present invention is also related to these processes for the partial synthesis of the compound having structure (IX). The processes according to these aspects of the invention are ideally suited in the context of the overall aim of the synthesis of 6-azido-2-N-acetyl-monosaccharide-nucleoside diphosphate having structure (IX).

[C.1] Synthesis of compound (I)

In one aspect, the invention concerns a process for preparing a 6-azido-6-deoxy monosaccharide compound having structure (I) according to the scheme:

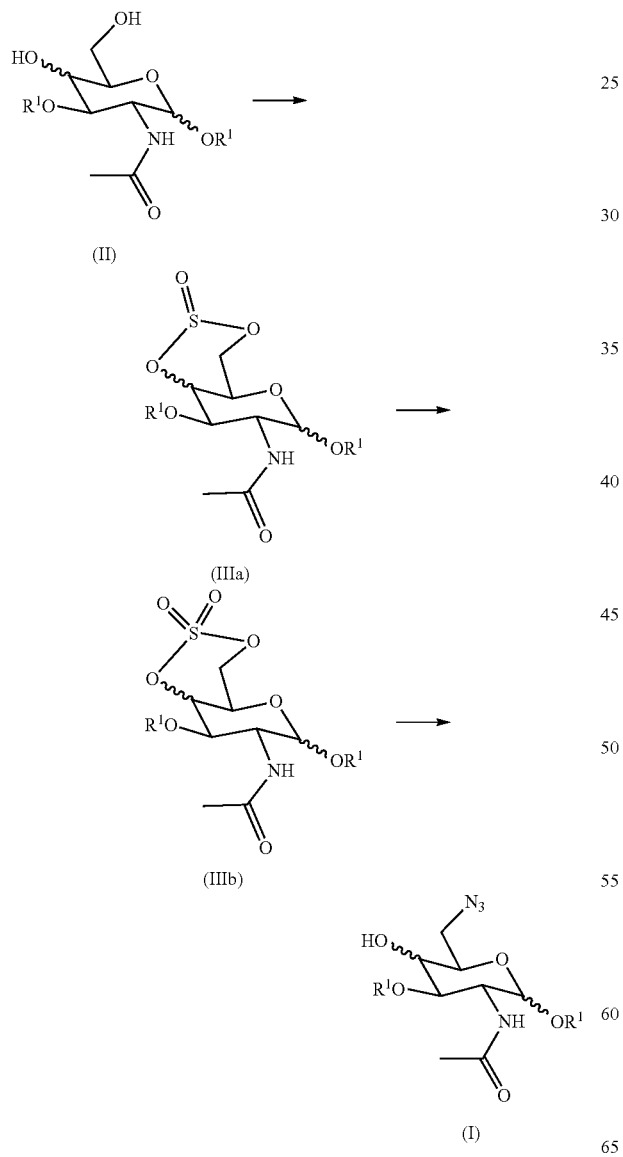

The process comprises:
(b) reacting a diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form the 6-azido-6-deoxy monosaccharide having structure (I).

Steps (b), (c) and (d) are defined above. $R^1$ represents acyl groups that are present as protecting groups for the hydroxyl groups attached to carbon atoms at positions 1 and 3 of the monosaccharide moiety. These acyl protecting groups may be introduced via step (a) prior to step (b). $R^1$ is independently selected from optionally substituted C(O)-alkyl, C(O)-aryl and C(O)-arylalkyl. Preferably, both occurrences of $R^1$ are the same. In a preferred embodiment, each occurrence of $R^1$ is C(O)Me, C(O)tBu, C(O)Ph or C(O)CH$_2$Ph. Most preferably, each occurrence of $R^1$ is C(O)Me, in which case "acylated" may be referred to as "acetylated".

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (II) is preferably prepared from N-acetyl-2-galactosamine (GalNAc) or N-acetyl-2-glucosamine (GlcNAc), preferably from GalNAc. This preparation is preferably accomplished by step (a) as defined above.

The process according to this aspect is ideally suited in the context of the overall aim of the present invention, i.e. the synthesis of 6-azido-2-N-acetyl-monosaccharide-nucleoside diphosphate having structure (IX). It is thus preferred that the compound having structure (I), obtained in step (d) is further converted into of 6-azido-2-N-acetyl-monosaccharide-nucleoside diphosphate having structure (IX) or a salt thereof. Such conversion may be accomplished in any suitable way.

Preferably, this conversion involves conversion of the 6-azido-6-deoxy monosaccharide compound having structure (I) into a 1-monophosphate monosaccharide compound, which is reacted with a nucleoside monophosphate to form the compound having structure (IX), which typically has structure (V). This reaction sequence involves a deprotecting step, either before or after reaction of the 1-monophosphate monosaccharide compound with the nucleoside monophosphate.

The 1-monophosphate monosaccharide having structure (V) is defined as follows:

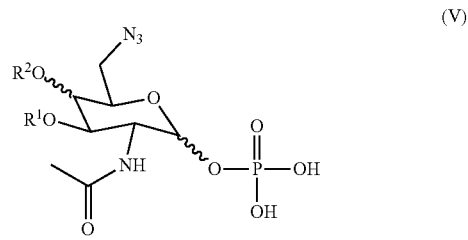

Herein, $R^1$ and $R^2$ are independently selected from H and optionally substituted C(O)-alkyl, C(O)-aryl and C(O)-arylalkyl. Furthermore, the following applies:

for compound (Va): $R^1$ and $R^2$ are independently selected from optionally substituted C(O)-alkyl, C(O)-aryl and C(O)-arylalkyl;

for compound (Vb): $R^1$ and $R^2$ are both H.

In a preferred embodiment, the conversion of the compounds of structure (I) into the compound of structure (V), is performed by one of the following reaction sequences:

Steps (e), (f) and (g), which typically affords the compound having structure (Va);

Steps (e), (x1), (x2), (x3) and (x4), which typically affords the compound having structure (Va);

Steps (y1) and (y2), which typically affords the compound having structure (Vb).

The compound having structure (V) is preferably converted into the compound having structure (IX), preferably by steps (i) and (j) or by steps (1) and (i1). In case the compound having structure (Vb) is obtained, it is preferably converted into the compound having structure (IX) by step (i1). In that case, the deprotection of step (j) or (1) is not required. In case the reaction sequence towards the compound having structure (IX) involves both step (x4) and step (1), these can optionally be performed concomitantly, affording the compound having structure (Vb). Herein, it is preferred that $R^3$ is $CH_2OC(O)$alkyl, wherein alkyl is preferably $C_{1-6}$ alkyl, more preferably $C_{1-2}$ alkyl, most preferably methyl.

In a preferred embodiment, the conversion of the compounds of structure (I) into the compound of structure (IX), via the compound having structure (V), is performed by one of the following reaction sequences:

Steps (e), (f), (g), (i), and (j);

Steps (e), (f), (g), (j1), and (i1);

Steps (e), (x1), (x2), (x3), (x4), (i), and optionally (j);

Steps (e), (x1), (x2), (x3), (x4), 61), (i1);

Steps (y1), (y2), and (i).

Steps (e), (f), (g), (i), 6), (i1), 61), (x1), (x2), (x3), (x4), (y1) and (y2) are defined above.

[C.2] Synthesis of Compound (Va) Via Compound (VII)

In one aspect, the invention concerns a process for preparing a 6-azido-6-deoxy-1-monophosphate monosaccharide compound having structure (Va) according to the scheme:

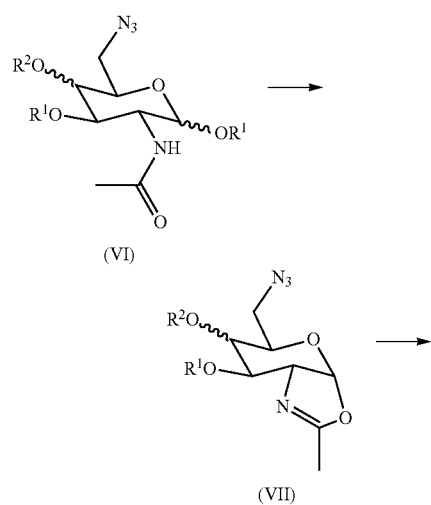

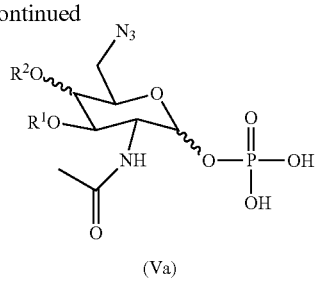

The process comprises:

(f) converting a 6-azido-6-deoxy monosaccharide having structure (VI) in the presence of one or more Lewis acids to form an oxazoline compound having structure (VII);

(g) reacting the oxazoline compound having structure (VII) with phosphoric acid to form the 6-azido-6-deoxy-1-monophosphate monosaccharide compound having structure (Va).

Steps (f) and (g) are defined above. $R^1$ represents the acyl group(s) that is/are present as protecting group(s) for the hydroxyl groups attached to carbon atoms at position 3 (and position 1 for (VI)) of the monosaccharide moiety. The acyl protecting group(s) may be introduced via step (a) prior to step (f. $R^1$ is independently selected from optionally substituted C(O)-alkyl, C(O)-aryl and C(O)-arylalkyl. In one embodiment, $R^1$ is selected from C(O)-alkyl, C(O)-aryl and C(O)-arylalkyl. Preferably, both occurrences of $R^1$ are the same. In a preferred embodiment, each occurrence of $R^1$ is C(O)Me, C(O)tBu, C(O)Ph or $C(O)CH_2Ph$. Most preferably, each occurrence of $R^1$ is C(O)Me, in which case "acylated" may be referred to as "acetylated".

$R^2$ represents the acyl group that are present as protecting groups for the hydroxyl group attached to carbon atoms at position 4 of the monosaccharide moiety. The acyl protecting group(s) may be introduced via step (e) prior to step (f). $R^2$ is selected from optionally substituted C(O)-alkyl, C(O)-aryl and C(O)-arylalkyl. In one embodiment, $R^2$ is selected from C(O)-alkyl, C(O)-aryl and C(O)-arylalkyl. In a preferred embodiment, $R^2$ is C(O)Me, C(O)tBu, C(O)Ph or $C(O)CH_2Ph$. Most preferably, $R^2$ is C(O)Me, in which case "acylated" may be referred to as "acetylated". $R^1$ and $R^2$ may be the same or different, which is irrelevant for further conversion of the compound having structure (Va) in the methods of the present invention.

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (VI) is preferably prepared from N-acetyl-2-galactosamine (GalNAc) or N-acetyl-2-glucosamine (GlcNAc), preferably from GalNAc. This preparation is preferably accomplished by step (e) as defined above, more preferably by steps (b), (c), (d) and (e) as defined above, most preferably by steps (a), (b), (c), (d) and (e) as defined above.

The process according to this aspect is ideally suited in the context of the overall aim of the present invention, i.e. the synthesis of 6-azido-2-N-acetyl-monosaccharide-nucleoside diphosphate having structure (IX). It is thus preferred that the compound having structure (Va), obtained in step (g) is further converted into of 6-azido-2-N-acetyl-monosaccharide-nucleoside diphosphate having structure (IX) or a salt thereof. Such conversion may be accomplished in any suitable way. Preferably, this conversion involves steps (i) and (j) or steps (1) and (i1) as defined above.

[C.3] Synthesis of Compound (Va) Via Compound (XII)

In one aspect, the invention concerns a process for preparing a 6-azido-6-deoxy-1-monophosphate monosaccharide compound having structure (Va) according to the scheme:

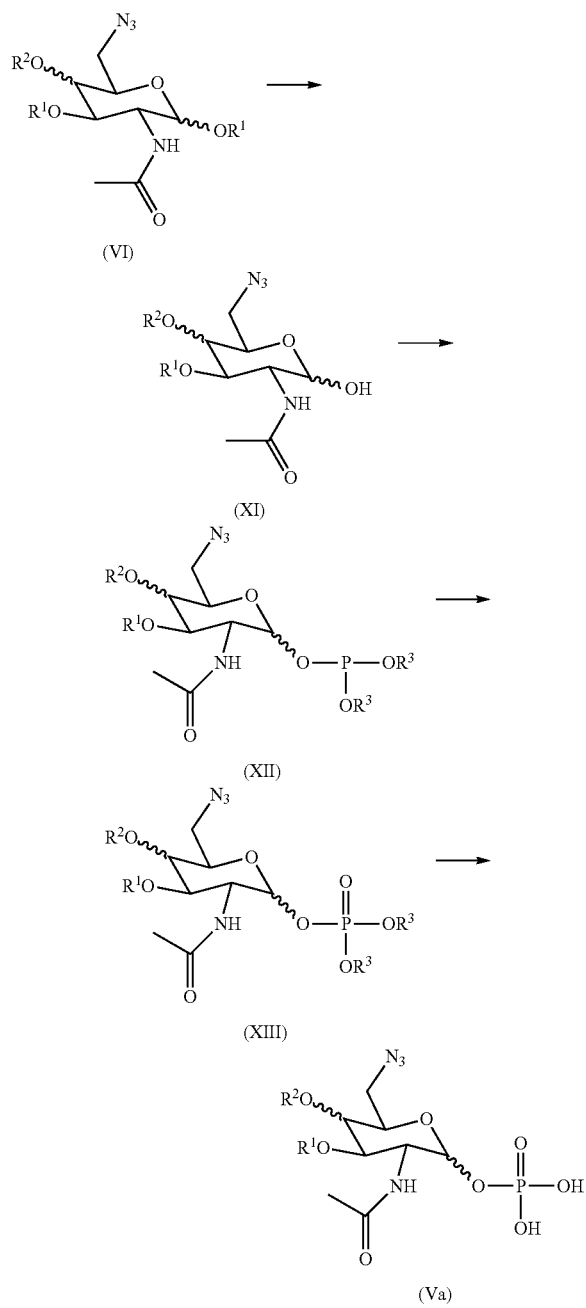

The process comprises:

(x1) deprotecting the anomeric position of compound having structure (VI) to form 1-hydroxy-monosaccharide compound having structure (XI);

(x2) converting the 1-hydroxy-monosaccharide compound having structure (XI) into the 6-azido-6-deoxy-1-monophosphite diester having structure (XII);

(x3) oxidizing the monophosphite diester having structure (XII) in the presence of an oxidizing agent, to form the 1-monophosphate diester compound having structure (XIII).

(x4) deprotecting the phosphate diester having structure (XIII) to form the 1-monophosphate monosaccharide compound having structure (Va).

Steps (x1), (x2), (x3) and (x4) are defined above. $R^1$ represents the acyl group(s) that are present as protecting group(s) for the hydroxyl groups attached to carbon atoms at position 3 (and position 1 for (VI)) of the monosaccharide moiety. The acyl protecting group(s) may be introduced via step (a) prior to step (x1). $R^1$ is independently selected from optionally substituted C(O)-alkyl, C(O)-aryl and C(O)-arylalkyl. Preferably, both occurrences of $R^1$ are the same. In a preferred embodiment, each occurrence of $R^1$ is C(O)Me, C(O)tBu, C(O)Ph or C(O)CH$_2$Ph. Most preferably, each occurrence of $R^1$ is C(O)Me, in which case "acylated" may be referred to as "acetylated".

$R^2$ represents the acyl group that are present as protecting groups for the hydroxyl group attached to carbon atoms at position 4 of the monosaccharide moiety. The acyl protecting group(s) may be introduced via step (e) prior to step (x1). $R^2$ is selected from optionally substituted C(O)-alkyl, C(O)-aryl and C(O)-arylalkyl. In a preferred embodiment, $R^2$ is C(O)Me, C(O)tBu, C(O)Ph or C(O)CH$_2$Ph. Most preferably, $R^2$ is C(O)Me, in which case "acylated" may be referred to as "acetylated". $R^1$ and $R^2$ may be the same or different, which is irrelevant for further conversion of the compound having structure (Va) in the methods of the present invention.

$R^3$ represents the phosphite substituent that is introduced in step (x2). $R^3$ is selected from $C_{1-6}$ alkyl, allyl, 2-cyanoethyl, 2-alkylsulfonylethyl, 2-arylsulfonylethyl, 2,2,2-trichloroethyl, CH$_2$OC(O)alkyl, fluorenylmethyl, 2-pyridylethyl, phenyl-$C_{1-2}$-alkyl (2-phenylethyl or phenylmethyl), wherein phenyl is optionally substituted with one or more halides or a nitro or methoxy group. In case $R^3$ is 2-alkylsulfonylethyl or CH$_2$OC(O)alkyl, it is preferred that alkyl is $C_{1-6}$ alkyl, more preferably $C_{1-2}$ alkyl, most preferably methyl. In case $R^3$ is 2-arylsulfonylethyl, it is preferred that aryl is phenyl.

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (VI) is preferably prepared from N-acetyl-2-galactosamine (GalNAc) or N-acetyl-2-glucosamine (GlcNAc), preferably from GalNAc. This preparation is preferably accomplished by step (e) as defined above, more preferably by steps (b), (c), (d) and (e) as defined above, most preferably by steps (a), (b), (c), (d) and (e) as defined above.

The process according to this aspect is ideally suited in the context of the overall aim of the present invention, i.e. the synthesis of 6-azido-2-N-acetyl-monosaccharide-nucleoside diphosphate having structure (IX). It is thus preferred that the compound having structure (Va), obtained in step (x4) is further converted into of 6-azido-2-N-acetyl-monosaccharide-nucleoside diphosphate having structure (IX) or a salt thereof. Such conversion may be accomplished in any suitable way.

Preferably, this conversion involves steps (i) and (j) or steps (1) and (i1) as defined above.

[C.4] Synthesis of Compound (Vb) Via Compound (XII)

In one aspect, the invention concerns a process for preparing a 6-azido-6-deoxy-1-monophosphate monosaccharide compound having structure (Vb) according to the scheme:

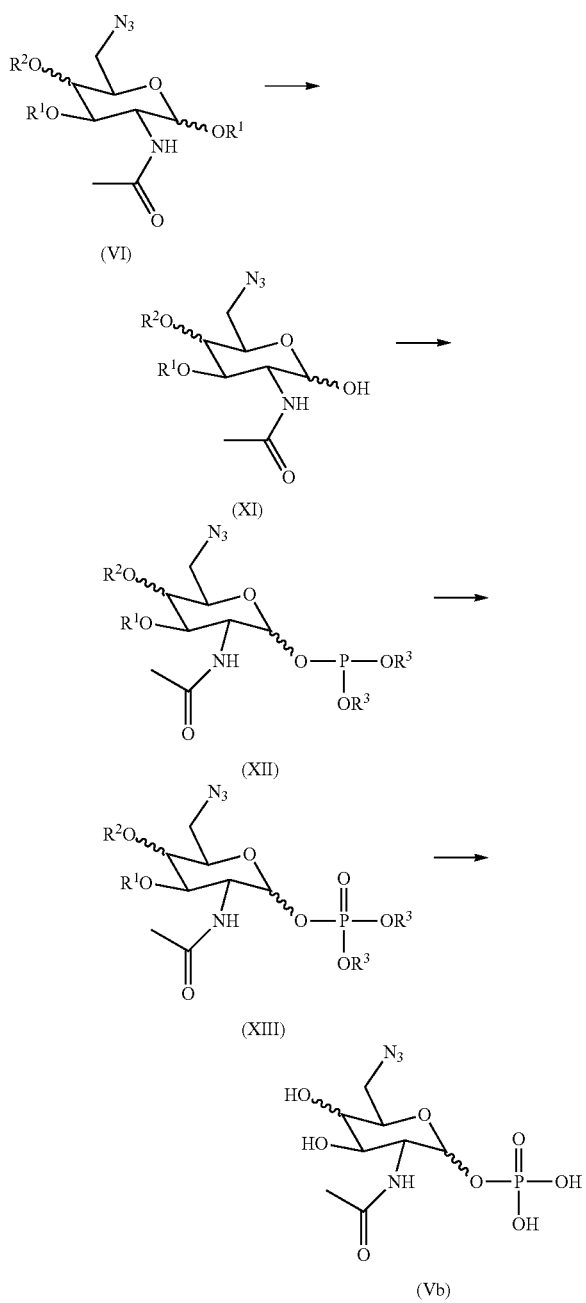

The process comprises:
(x1) deprotecting the anomeric position of compound having structure (VI) to form 1-hydroxy-monosaccharide compound having structure (XI);
(x2) converting the 1-hydroxy-monosaccharide compound having structure (XI) into the 6-azido-6-deoxy-1-monophosphite diester having structure (XII);
(x3) oxidizing the monophosphite diester having structure (XII) in the presence of an oxidizing agent, to form the 1-monophosphate diester compound having structure (XIII);
(x4) concomitantly deprotecting the phosphate diester and monosaccharide having structure (XIII) to form the 1-monophosphate monosaccharide compound having structure (Vb).

Steps (x1), (x2), (x3) and (x4) are defined above. $R^1$ represents the acyl group(s) that are present as protecting group(s) for the hydroxyl groups attached to carbon atoms at position 3 (and position 1 for (VI)) of the monosaccharide moiety. The acyl protecting group(s) may be introduced via step (a) prior to step (x1). $R^1$ is independently selected from optionally substituted C(O)-alkyl, C(O)-aryl and C(O)-arylalkyl. Preferably, both occurrences of $R^1$ are the same. In a preferred embodiment, each occurrence of $R^1$ is C(O)Me, C(O)tBu, C(O)Ph or C(O)CH$_2$Ph. Most preferably, each occurrence of $R^1$ is C(O)Me, in which case "acylated" may be referred to as "acetylated".

$R^2$ represents the acyl group that are present as protecting groups for the hydroxyl group attached to carbon atoms at position 4 of the monosaccharide moiety. The acyl protecting group(s) may be introduced via step (e) prior to step (x1). $R^2$ is selected from optionally substituted C(O)-alkyl, C(O)-aryl and C(O)-arylalkyl. In a preferred embodiment, $R^2$ is C(O)Me, C(O)tBu, C(O)Ph or C(O)CH$_2$Ph. Most preferably, $R^2$ is C(O)Me, in which case "acylated" may be referred to as "acetylated". $R^1$ and $R^2$ may be the same or different, which is irrelevant for the suitability of the process of the present aspect of the invention.

$R^3$ represents the phosphite substituent that is introduced in step (x2). $R^3$ is selected from $C_{1-6}$ alkyl, allyl, 2-cyanoethyl, 2-alkylsulfonylethyl, 2-arylsulfonylethyl, 2,2,2-trichloroethyl, CH$_2$OC(O)alkyl, fluorenylmethyl, 2-pyridylethyl, phenyl-$C_{1-2}$-alkyl (2-phenylethyl or phenylmethyl), wherein phenyl is optionally substituted with one or more halides or a nitro or methoxy group. In case $R^3$ is 2-alkylsulfonylethyl or CH$_2$OC(O)alkyl, it is preferred that alkyl is $C_{1-6}$ alkyl, more preferably $C_{1-2}$ alkyl, most preferably methyl. In case $R^3$ is 2-arylsulfonylethyl, it is preferred that aryl is phenyl.

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (VI) is preferably prepared from N-acetyl-2-galactosamine (GalNAc) or N-acetyl-2-glucosamine (GlcNAc), preferably from GalNAc. This preparation is preferably accomplished by step (e) as defined above, more preferably by steps (b), (c), (d) and (e) as defined above, most preferably by steps (a), (b), (c), (d) and (e) as defined above.

The process according to this aspect is ideally suited in the context of the overall aim of the present invention, i.e. the synthesis of 6-azido-2-N-acetyl-monosaccharide-nucleoside diphosphate having structure (IX). It is thus preferred that the compound having structure (Vb), obtained in step (x4) is further converted into of 6-azido-2-N-acetyl-monosaccharide-nucleoside diphosphate having structure (IX) or a salt thereof. Such conversion may be accomplished in any suitable way. Preferably, this conversion involves step (i) as defined above.

[C.5] Synthesis of Compound (Vb) Via Compound (XIV)

In one aspect, the invention concerns a process for preparing a 6-azido-6-deoxy-1-monophosphate monosaccharide compound having structure (Vb) according to the scheme:

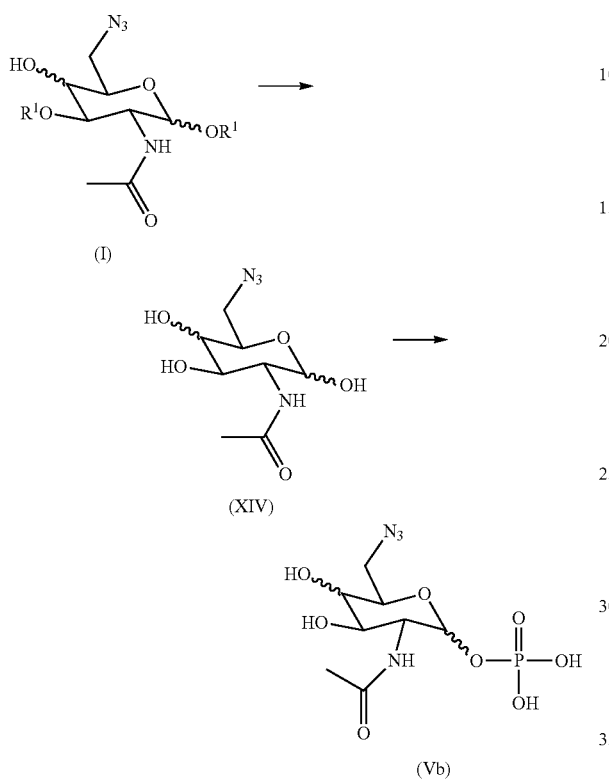

The process comprises the steps:
(y1) deprotecting the 6-azido-6-deoxy monosaccharide having structure (I) to form 1,3,4-trihydroxy-6-azido-monosaccharide compound having structure (XIV);
(y2) contacting the compound having structure (XIV) with a phosphorylating enzyme in the presence of a phosphate source to form 1-monophosphate monosaccharide compound having structure (Vb).

Steps (y1) and (y2) are defined above. $R^1$ represents the acyl groups that are present as protecting groups for the hydroxyl groups attached to carbon atoms at positions 1 and 3 of the monosaccharide moiety of compound (1). The acyl protecting group(s) may be introduced via step (a) prior to step (y1). $R^1$ is independently selected from optionally substituted C(O)-alkyl, C(O)-aryl and C(O)-arylalkyl. Preferably, both occurrences of $R^1$ are the same. In a preferred embodiment, each occurrence of $R^1$ is C(O)Me, C(O)tBu, C(O)Ph or C(O)CH$_2$Ph. Most preferably, each occurrence of $R^1$ is C(O)Me, in which case "acylated" may be referred to as "acetylated".

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (I) is preferably prepared from N-acetyl-2-galactosamine (GalNAc) or N-acetyl-2-glucosamine (GlcNAc), preferably from Gal-NAc. This preparation is preferably accomplished by steps (b), (c) and (d) as defined above, more preferably by steps (a), (b), (c) and (d) as defined above.

The process according to this aspect is ideally suited in the context of the overall aim of the present invention, i.e. the synthesis of 6-azido-2-N-acetyl-monosaccharide-nucleoside diphosphate having structure (IX). It is thus preferred that the compound having structure (Vb), obtained in step (x4) is further converted into of 6-azido-2-N-acetyl-monosaccharide-nucleoside diphosphate having structure (IX) or a salt thereof. Such conversion may be accomplished in any suitable way.

Preferably, this conversion involves step (i1) as defined above.

[C.6] Synthesis of Compound (VIII)

In one aspect, the invention concerns a process for preparing a 6-azido-6-deoxy-1-monophosphate monosaccharide compound having structure (VIII) according to the scheme:

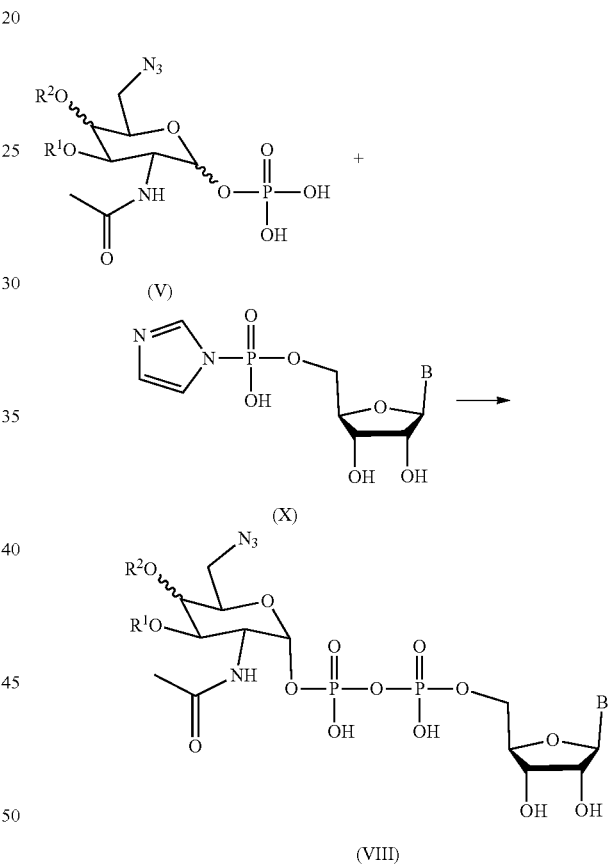

The process comprises:
(z) reacting a compound having structure (Va) with a nucleoside monophosphate having structure (X) to form a nucleoside diphosphate having structure (VIII), optionally wherein the reaction is performed in the presence of an organic base, MgCl$_2$ or ZnCl$_2$.

Step (z) is defined above. In the process according to the present aspect, $R^1$ may be H or an acyl group that is present as protecting group for the hydroxyl groups attached to the carbon atom at position 3 of the monosaccharide moiety. The acyl protecting group may be introduced via step (a) prior to step (z). $R^1$ is selected from H and optionally substituted C(O)-alkyl, C(O)-aryl and C(O)-arylalkyl. In a preferred embodiment, $R^1$ is H, C(O)Me, C(O)tBu, C(O)Ph or C(O)CH$_2$Ph. Most preferably, each occurrence of R$^1$ is C(O)Me, in which case "acylated" may be referred to as "acetylated". In one embodiment, the compound having structure (V) is a compound having structure (Va) and R$^1$ is selected from H, C(O)-alkyl, C(O)-aryl and C(O)-arylalkyl. In an alternative embodiment, the compound having structure (V) is a compound having structure (Vb) and R$^1$ is H.

In the process according to the present aspect, R$^2$ may be H or an acyl group that is present as protecting groups for the hydroxyl group attached to carbon atoms at position 4 of the monosaccharide moiety. The acyl protecting group may be introduced via step (e) prior to step (z).

R$^2$ is selected from H and optionally substituted C(O)-alkyl, C(O)-aryl and C(O)-arylalkyl. In a preferred embodiment, R$^2$ is H, C(O)Me, C(O)tBu, C(O)Ph or C(O)CH$_2$Ph. Most preferably, R$^2$ is C(O)Me, in which case "acylated" may be referred to as "acetylated". In one embodiment, the compound having structure (V) is a compound having structure (Va) and R$^2$ is selected from H, optionally substituted C(O)-alkyl, C(O)-aryl and C(O)-arylalkyl. In an alternative embodiment, the compound having structure (V) is a compound having structure (Vb) and R$^2$ is H.

The monosaccharide is preferably N-acetyl-2-galactosamine (GalNAc) or N-acetyl-2-glucosamine (GlcNAc). In other words, the wiggly bond at the carbon atom at position 4 of the monosaccharide moiety can either be axial (galactose configuration) or equatorial (glucose configuration). Preferably, the monosaccharide moiety is GalNAc. Similarly, the compound having structure (V) is preferably prepared from N-acetyl-2-galactosamine (GalNAc) or N-acetyl-2-glucosamine (GlcNAc), preferably from GalNAc. This preparation is preferably accomplished by:

Steps (f) and (g), in which case a compound having structure (Va) is obtained;
Steps (e), (f) and (g), in which case a compound having structure (Va) is obtained;
Steps (b), (c), (d), (e), (f) and (g), in which case a compound having structure (Va) is obtained;
Steps (a), (b), (c), (d), (e), (f) and (g), in which case a compound having structure (Va) is obtained;
Steps (x1), (x2), (x3) and (x4), in which case a compound having structure (Va) or (Vb) is obtained;
Steps (e), (x1), (x2), (x3) and (x4), in which case a compound having structure (Va) or (Vb) is obtained;
Steps (b), (c), (d), (e), (x1), (x2), (x3) and (x4), in which case a compound having structure (Va) or (Vb) is obtained;
Steps (a), (b), (c), (d), (e), (x1), (x2), (x3) and (x4), in which case a compound having structure (Va) or (Vb) is obtained;
Steps (y1) and (y2), in which case a compound having structure (Vb) is obtained;
Steps (b), (c), (d), (y1) and (y2), in which case a compound having structure (Vb) is obtained;
Steps (a), (b), (c), (d), (y1) and (y2), in which case a compound having structure (Vb) is obtained.

Steps (a), (b), (c), (d), (e), (f), (g), (x1), (x2), (x3), (x4), (y1) and (y2) are defined above.

The process according to this aspect is ideally suited in the context of the overall aim of the present invention, i.e. the synthesis of 6-azido-2-N-acetyl-monosaccharide-nucleoside diphosphate having structure (IX). In one embodiment, both R$^1$ and R$^2$ are H and the process according to this aspect affords this compound already. Alternatively, it is preferred that the compound having structure (VIII), obtained in step (z) is further converted into of 6-azido-2-N-acetyl-monosaccharide-nucleoside diphosphate having structure (IX) or a salt thereof. Such conversion may be accomplished in any suitable way. Preferably, this conversion involves step (j) as defined above.

[D] Syntheses of Compound (IX)

The present invention provides several approaches towards the total synthesis of target compound (IX), which make use of the steps, processes and intermediates defined above. Each of these approaches offers one or more unique advantages over prior art processes.

[D.1] Synthesis of Compound (IX) Via Compound (VII) and (VIII)

In one aspect, the invention concerns a process for preparing a nucleoside diphosphate having structure (IX) or salt thereof according to the scheme:

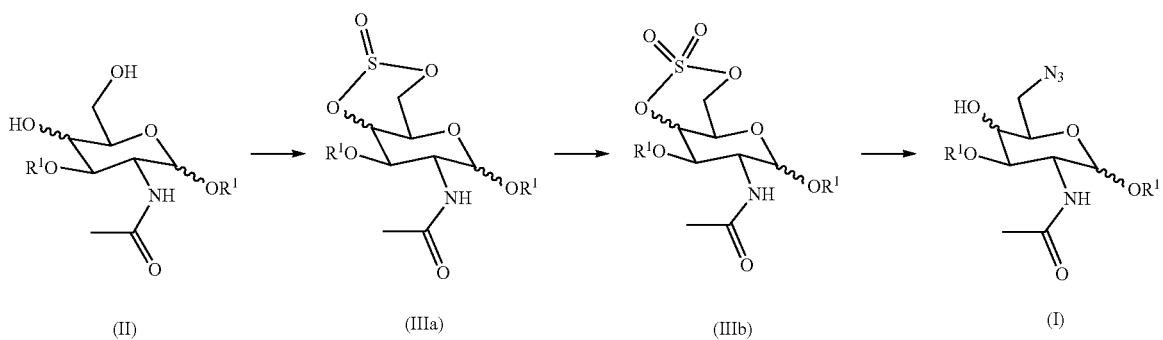

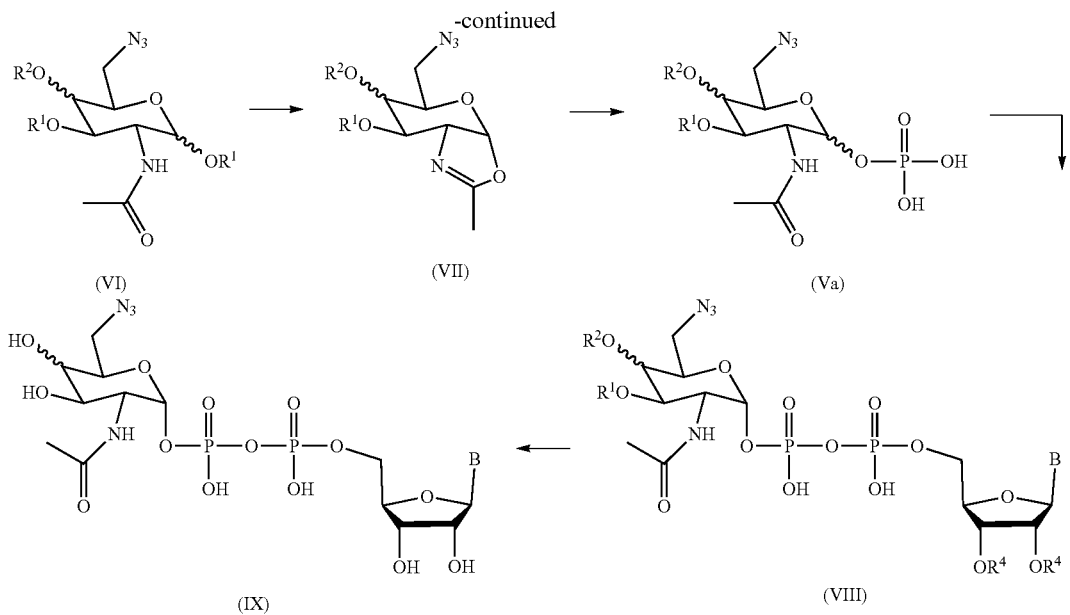

The process comprises:
(a) converting N-acetylglucosamine or N-acetylgalactosamine into a 1,3-di-acylated compound having structure (II);
(b) reacting the diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form a 6-azido-6-deoxy monosaccharide having structure (I);
(e) protecting the 6-azido-6-deoxy monosaccharide having structure (I) to form 6-azido-6-deoxy monosaccharide compound having structure (VI);
(f) converting the compound having structure (VI) in the presence of one or more Lewis acids to form an oxazoline compound having structure (VII);
(g) reacting the compound having structure (VII) with phosphoric acid to form the 1-monophosphate monosaccharide compound having structure (Va);
(i) reacting the compound having structure (Va) with a nucleoside monophosphate into an acylated nucleoside diphosphate having structure (VIII); and
(j) deprotecting the acylated nucleoside diphosphate having structure (VIII) to obtain nucleoside diphosphate having structure (IX), or salt thereof.

Herein, $R^1$ is independently selected from optionally substituted C(O)-alkyl, C(O)-aryl and C(O)-arylalkyl; $R^2$ is selected from optionally substituted C(O)-alkyl, C(O)-aryl and C(O)-arylalkyl; $R^4$ are both hydrogen or both occurrences of $R^4$ are joined together via a carbonyl moiety; and B is a nucleobase. Preferred embodiments for each of the steps and compounds in this process are defined above.

[D.2] Synthesis of Compound (IX) Via Compounds (VII) and (Vb)

In one aspect, the invention concerns a process for preparing a nucleoside diphosphate having structure (IX) or salt thereof according to the scheme:

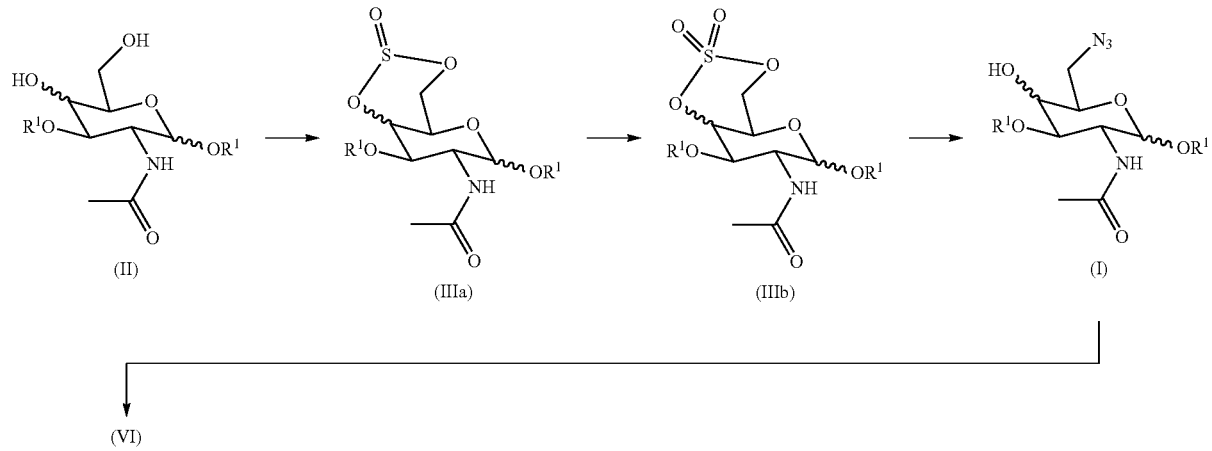

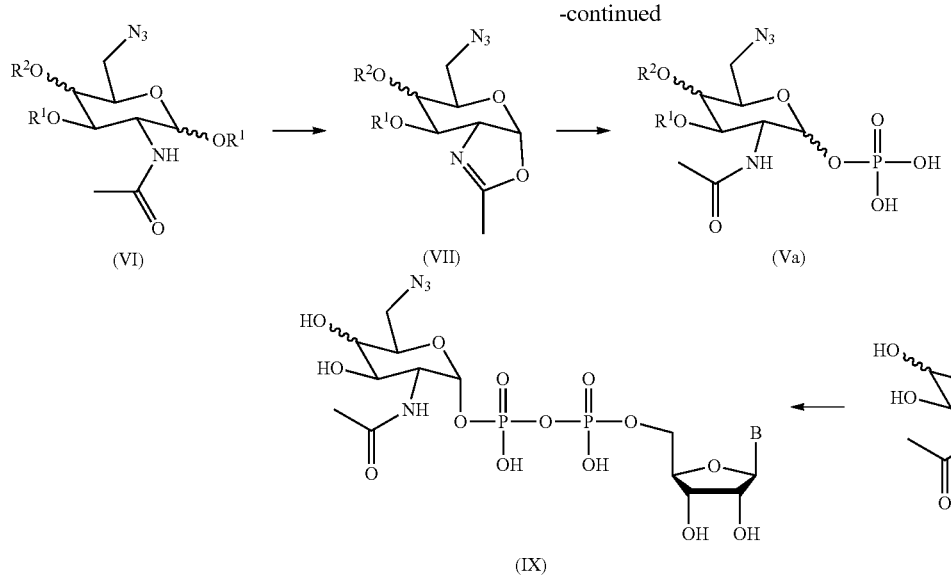

(VI) → (VII) → (Va) →

(IX) ← (Vb)

The process comprises:
(a) converting N-acetylglucosamine or N-acetylgalactosamine into a 1,3-di-acylated compound having structure (II);
(b) reacting the diol having structure (I) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form a 6-azido-6-deoxy monosaccharide having structure (I);
(e) protecting the 6-azido-6-deoxy monosaccharide having structure (I) to form 6-azido-6-deoxy monosaccharide compound having structure (VI);
(f) converting the compound having structure (VI) in the presence of one or more Lewis acids to form an oxazoline compound having structure (VII);
(g) reacting the compound having structure (VII) with phosphoric acid to form the 1-monophosphate monosaccharide compound having structure (Va);

(j1) deprotecting the compound having structure (Va) to obtain a 1-monophosphate monosaccharide compound having structure (Vb);
(i1) reacting the compound having structure (Vb) with a nucleoside monophosphate into a nucleoside diphosphate having structure (IX).

Herein, $R^1$ is independently selected from optionally substituted C(O)-alkyl, C(O)-aryl and C(O)-arylalkyl; $R^2$ is selected from optionally substituted C(O)-alkyl, C(O)-aryl and C(O)-arylalkyl; and B is a nucleobase. Preferred embodiments for each of the steps and compounds in this process are defined above.

In one embodiment according to this aspect of the invention, step (f is omitted and the compound having structure (VI) is subjected to step (g1) to afford the compound having structure (Va).

[D.3] Synthesis of Compound (IX) Via Compounds (XII) and (VIII)

In one aspect, the invention concerns a process for preparing a nucleoside diphosphate having structure (IX) or salt thereof according to the scheme:

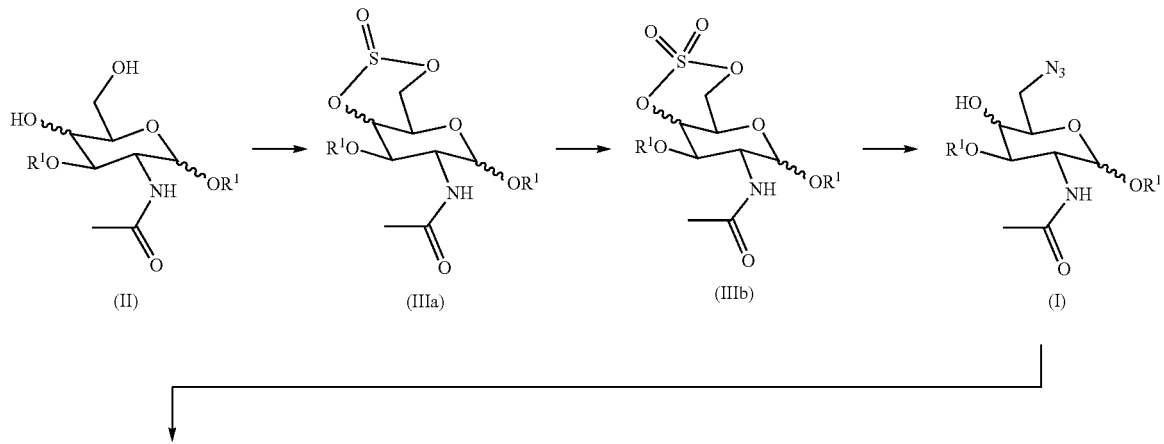

(II) → (IIIa) → (IIIb) → (I)

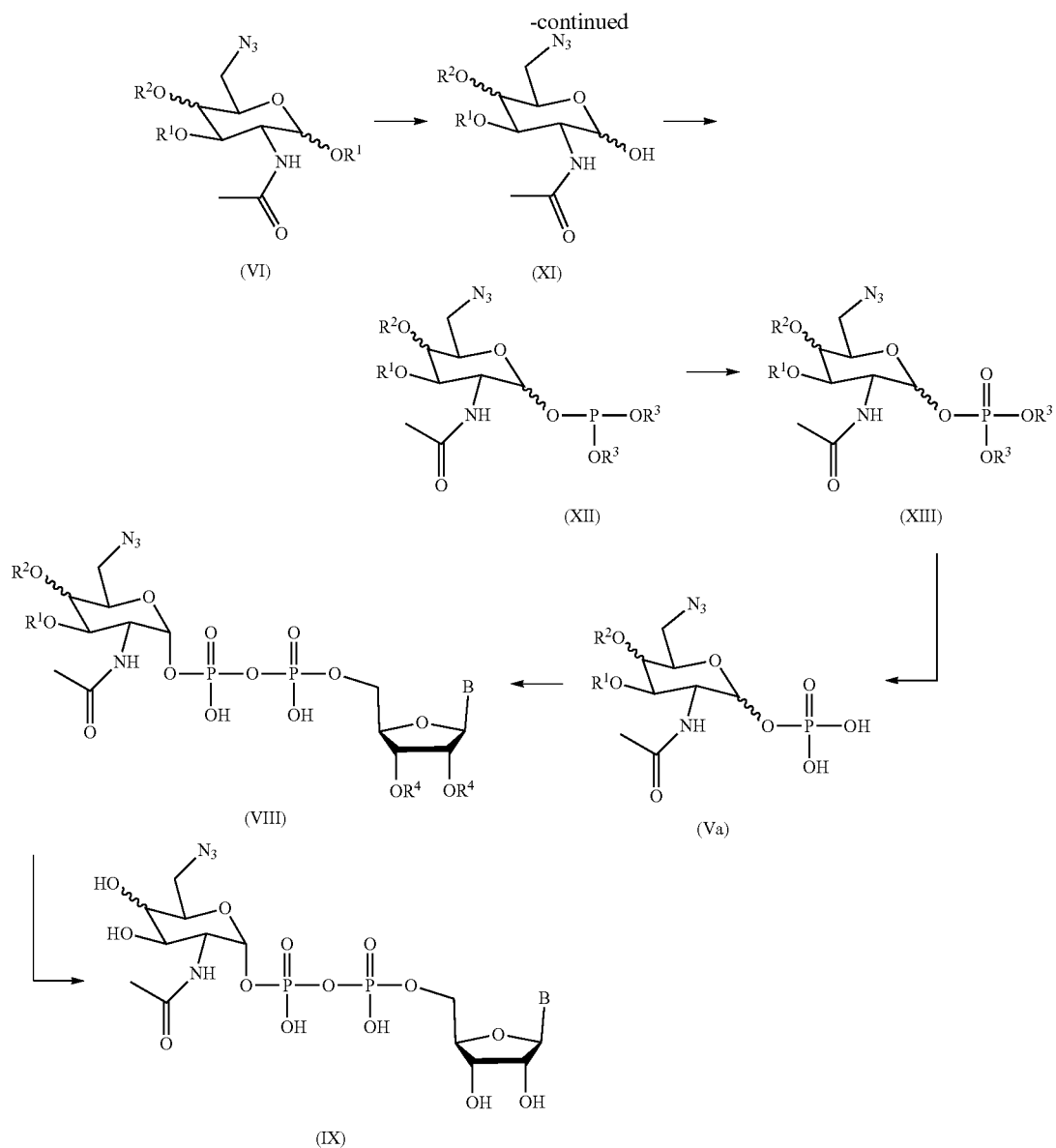

The process comprises:
(a) converting N-acetylglucosamine or N-acetylgalactosamine into a 1,3-di-acylated compound having structure (II);
(b) reacting the diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form a 6-azido-6-deoxy monosaccharide having structure (I);
(e) protecting the 6-azido-6-deoxy monosaccharide having structure (I) to form 6-azido-6-deoxy monosaccharide compound having structure (VI);
(x1) deprotecting the anomeric position of compound having structure (VI) to form 1-hydroxy-monosaccharide compound having structure (XI);

(x2) converting the 1-hydroxy-monosaccharide compound having structure (XI) into the 6-azido-6-deoxy-1-monophosphite diester having structure (XII);
(x3) oxidizing the monophosphite diester having structure (XII) in the presence of an oxidizing agent, to form the 1-monophosphate diester compound having structure (XIII);
(x4) deprotecting the phosphate diester having structure (XIII) to form the 1-monophosphate monosaccharide compound having structure (Va);
(i) reacting the compound having structure (Va) with a nucleoside monophosphate into an acylated nucleoside diphosphate having structure (VIII); and
(j) deprotecting the acylated nucleoside diphosphate having structure (VIII) to obtain nucleoside diphosphate having structure (IX), or salt thereof.

Herein, $R^1$ is independently selected from optionally substituted C(O)-alkyl, C(O)-aryl and C(O)-arylalkyl; $R^2$ is selected from optionally substituted C(O)-alkyl, C(O)-aryl and C(O)-arylalkyl; $R^3$ is selected from $C_{1-6}$ alkyl, allyl, 2-cyanoethyl, 2-alkylsulfonylethyl, 2-arylsulfonylethyl, 2,2,2-trichloroethyl, fluorenylmethyl, 2-pyridylethyl, phenyl-$C_{1\text{-}2}$-alkyl (2-phenylethyl or phenylmethyl), wherein phenyl is optionally substituted with one or more halides or a nitro or methoxy group; $R^4$ are both hydrogen or both occurrences of $R^4$ are joined together via a carbonyl moiety; and B is a nucleobase. Preferred embodiments for each of the steps and compounds in this process are defined above.

[D.4] Synthesis of Compound (IX) Via Compounds (XII) and (Vb)

In one aspect, the invention concerns a process for preparing a nucleoside diphosphate having structure (IX) or salt thereof according to the scheme:

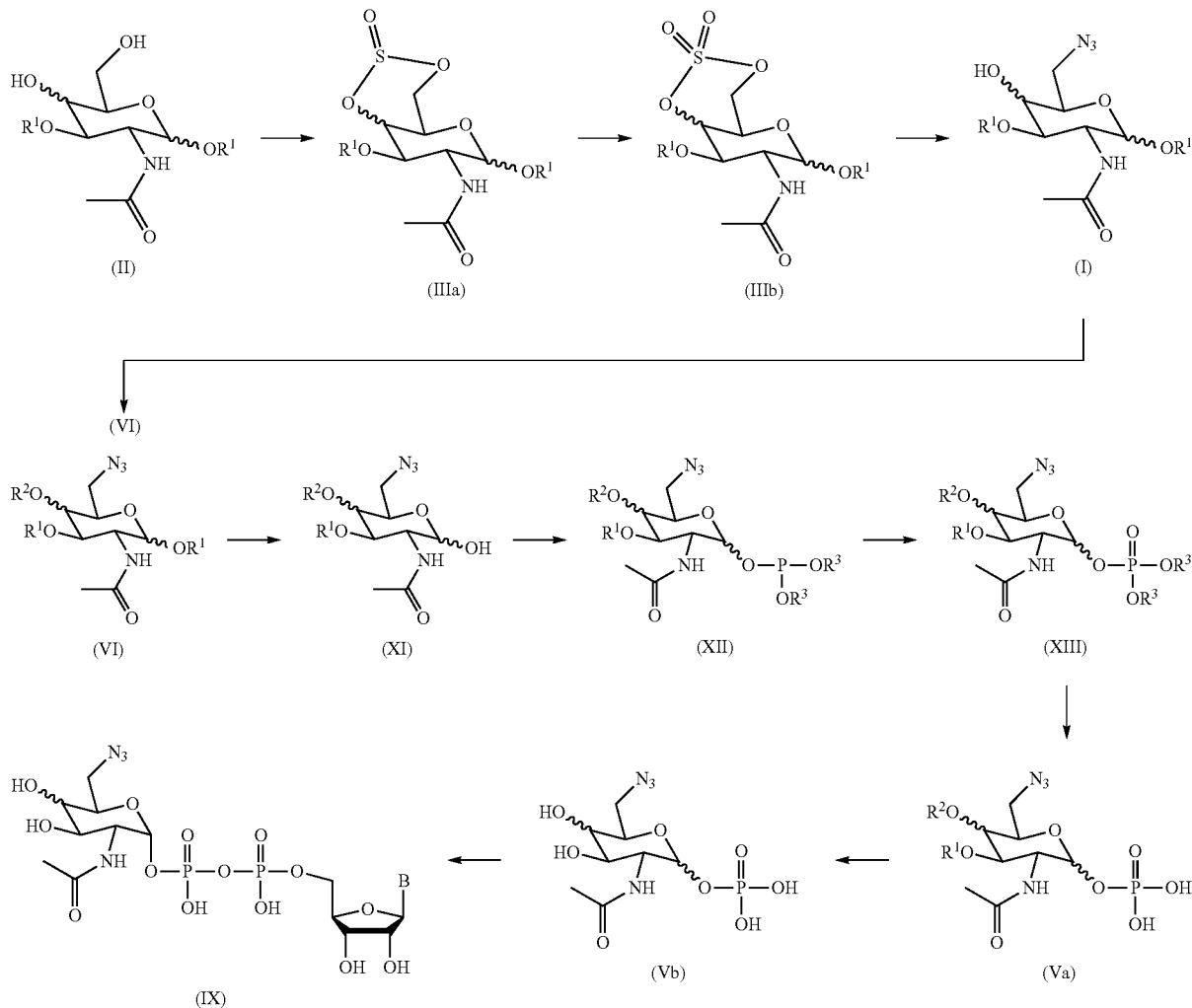

The process comprises:

(a) converting N-acetylglucosamine or N-acetylgalactosamine into a 1,3-di-acylated compound having structure (II);

(b) reacting the diol having structure (II) with a sulfitylating agent to form a cyclic sulfite having structure (IIIa);

(c) reacting the cyclic sulfite having structure (IIIa) with an oxidizing agent to form a cyclic sulfate having structure (IIIb);

(d) reacting the cyclic sulfate having structure (IIIb) with an inorganic azide to form a 6-azido-6-deoxy monosaccharide having structure (I);

(e) protecting the 6-azido-6-deoxy monosaccharide having structure (I) to form 6-azido-6-deoxy monosaccharide compound having structure (VI);

(x1) deprotecting the anomeric position of compound having structure (VI) to form 1-hydroxy-monosaccharide compound having structure (XI);

(x2) converting the 1-hydroxy-monosaccharide compound having structure (XI) into the 6-azido-6-deoxy-1-monophosphite diester having structure (XII);

(x3) oxidizing the monophosphite diester having structure (XII) in the presence of an oxidizing agent, to form the 1-monophosphate diester compound having structure (XIII);
(x4) deprotecting the phosphate diester having structure (XIII) to form the 1-monophosphate monosaccharide compound having structure (Va);
(j1) deprotecting the compound having structure (Va) to obtain a 1-monophosphate monosaccharide compound having structure (Vb);
(i1) reacting the compound having structure (Vb) with a nucleoside monophosphate into an acylated nucleoside diphosphate having structure (IX).

Herein, $R^1$ is independently selected from optionally substituted C(O)-alkyl, C(O)-aryl and C(O)-arylalkyl; $R^2$ is selected from optionally substituted C(O)-alkyl, C(O)-aryl and C(O)-arylalkyl; $R^3$ is selected from $C_{1-6}$ alkyl, allyl, 2-cyanoethyl, 2-alkylsulfonylethyl, 2-arylsulfonylethyl, 2,2,2-trichloroethyl, fluorenylmethyl, 2-pyridylethyl, phenyl-$C_{1-2}$-alkyl (2-phenylethyl or phenylmethyl), wherein phenyl is optionally substituted with one or more halides or a nitro or methoxy group; and B is a nucleobase. Preferred embodiments for each of the steps and compounds in this process are defined above.

[D.5] Synthesis of Compound (IX) Via Compound (XIV)

In one aspect, the invention concerns a process for preparing a nucleoside diphosphate having structure (IX) or salt thereof according to the scheme:

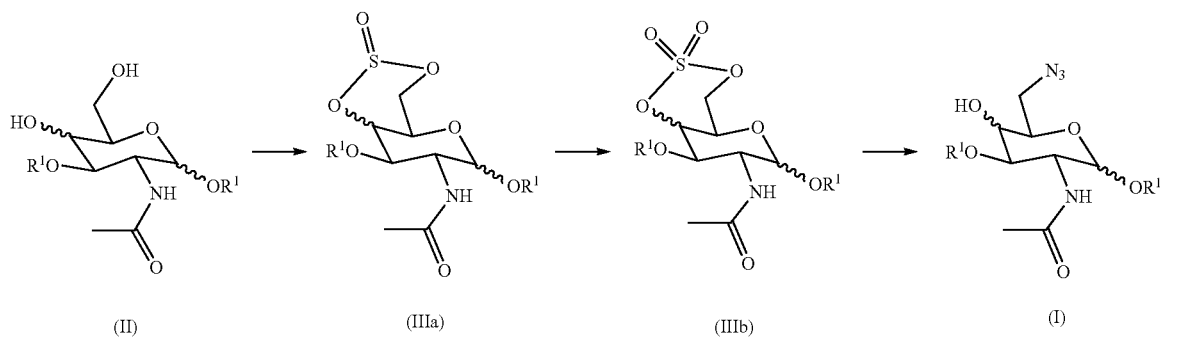

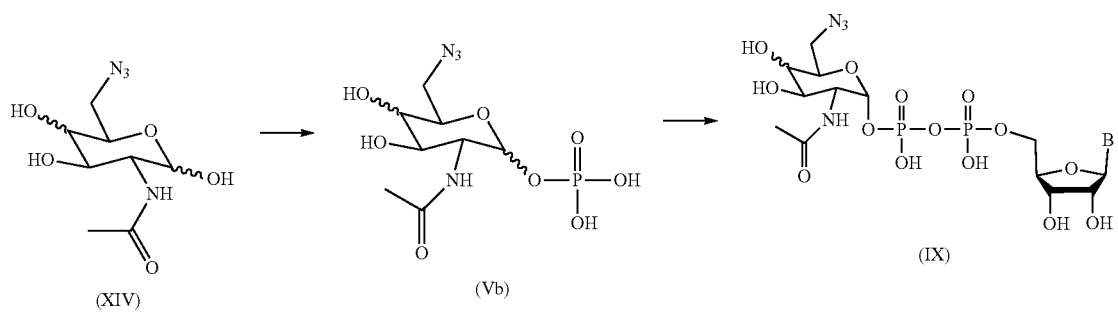

The process comprises:
(a) converting N-acetylglucosamine or N-acetylgalactosamine into a 1,3-di-acylated compound having structure (II);
(b) reacting the diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form a 6-azido-6-deoxy monosaccharide having structure (I);
(y1) deprotecting the 6-azido-6-deoxy monosaccharide having structure (I) to form 1,3,4-trihydroxy-6-azido-monosaccharide compound having structure (XIV);
(y2) contacting the compound having structure (XIV) with a phosphorylating enzyme in the presence of a phosphate source to form 1-monophosphate monosaccharide compound having structure (Vb);
(i) reacting the compound having structure (Vb) with a nucleoside monophosphate into a nucleoside diphosphate having structure (IX), or salt thereof.

Herein, $R^1$ is independently selected from optionally substituted C(O)-alkyl, C(O)-aryl and C(O)-arylalkyl; and B is a nucleobase. Preferred embodiments for each of the steps and compounds in this process are defined above.

EXAMPLES

Chemicals were purchased from commonly used suppliers (Sigma-Aldrich, Acros, Alfa Aesar, Fluorochem, Apollo Scientific Ltd and TCI) and were used without further purification. Solvents (including dry solvents) for chemical transformations, work-up and chromatography were purchased from Aldrich (Dorset, UK) at HPLC grade, and used without further distillation. Silica gel 60 F254 analytical thin layer chromatography (TLC) plates were from Merck (Darmstadt, Germany) and visualized under UV light, with potassium permanganate stain or anisaldehyde stain. Chromatographic purifications were performed using Acros silica gel (0.06-0.200, 60A) or prepacked columns (Screening Devices) in combination with a Buchi Sepacor C660 fraction collector (Flawil, Switzerland). Deuterated solvents used for NMR spectroscopy were obtained from Cambridge Isotope Laboratories.

Conditions for examples 1-1 to 1-3 were based on Yule et al., *Tet. Lett.*, 36, 1995, 6839-6842, Jiaang et al., *Synlett*, 2000, 6, 797-800, and Nishimura et al., *Angew. Chem. Int. Ed.*, 2012, 51, 3386-3390, incorporated by reference.

Example 1-1: Synthesis of 4,6-O-benzylidene-N-acetyl-D-galactosamine

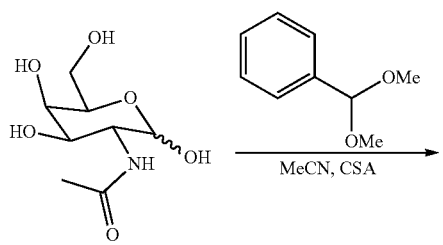

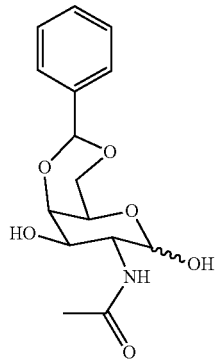

To a suspension of N-acetyl-D-galactosamine (1299 g, 5.9 mol) in MeCN (13 L) was added DL-camphorsulfonic acid (81 g, 352 mmol) and benzaldehyde dimethylacetal (2190 g, 2160 mL, 14.4 mol). The reaction was stirred at room temperature and filtered over a Buchner filter. The white filter cake was rinsed with MeCN (10×1 L) and dried on the filter overnight. Drying in a circulation oven at 35° C. for four days yielded the product (1938 g, 107%). The pure product was obtained by crystallization from EtOH/H$_2$O (13:1-9:1) at 5-8° C. for 16-24 hours as a white crystalline solid. $^1$H NMR (400 MHz, DMSO) δ (ppm) 7.49-7.46 (m, 2H), 7.38-7.34 (m, 3H), 5.56 (s, 1H), 5.04-5.03 (m, 1H), 4.14-4.13 (m, 1H), 4.08-3.94 (m, 3H), 3.85-3.78 (m, 2H), 1.82 (s, 3H).

Example 1-2: Synthesis of 1,3-di-O-acetyl-4,6-O-benzylidene-N-acetyl-D-galactosamine

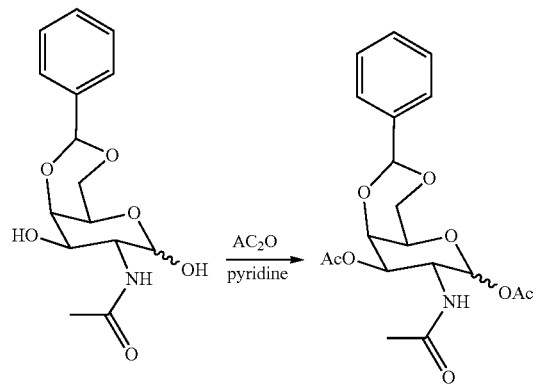 [SMILES: CC(=O)NC1C(O)OC2COC(c3ccccc3)OC2C1O ; CC(=O)NC1C(OC(C)=O)OC2COC(c3ccccc3)OC2C1OC(C)=O]

Starting material 4,6-O-benzylidene-N-acetyl-D-galactosamine (1938 g, 6.3 mmol) was dissolved in pyridine (7750 mL) and dropwise acetic anhydride (1919 g, 1.765 L, 18.8 mol) was added over 10 minutes. The reaction mixture was stirred at room temperature overnight, followed by addition of ice water (19.5 L). After 15 minutes stirring an extra scoop of ice was added and after another 15 minutes the mixture was filtrated. The cake was washed with ice water (3×6 L) and dried overnight on the filter followed by drying in a circulation oven at 45° C. overnight. The crude material was dissolved in methanol (13.7 L) and the mixture was heated to reflux to get a clear solution. The solution was cooled to room temperature overnight and subsequent to 0° C. in an ice bath for 4 h followed by filtration. The cake was washed with the filtrate for three times and dried on the filter for 1.5 h. Drying in a circulation oven at 45° C. for 3.5 days yielded the product 2 (1450 g, 3.7 mol, 59%). $^1$H NMR (400 MHz, CDCl$_3$) δ (ppm) 7.53-7.50 (m, 2H), 7.39-7.53 (m, 3H), 6.34 (d, J=4.8 Hz, 1H), 5.57 (d, J=12 Hz, 1H), 5.24 (dd, J=11.2, 4.4 Hz, 1H), 4.92-4.85 (m, 1H), 4.34 (d, J=4 Hz, 1H), 4.29-4.24 (m, 1H), 4.05-4.00 (m, 1H), 2.15 (s, 3H), 2.10 (s, 3H), 1.93 (s, 3H).

Example 1-3: Synthesis of 1,3-di-O-acetyl-N-acetyl-D-galactosamine (2)

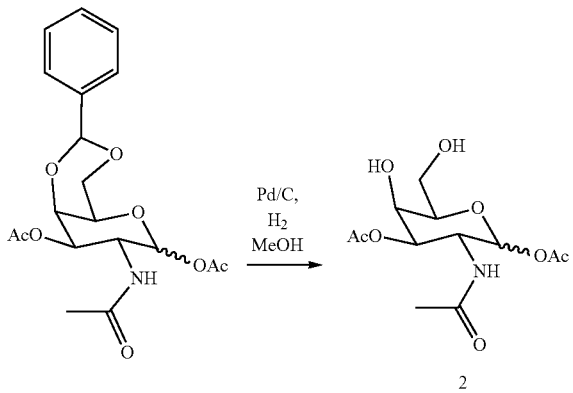 [SMILES: CC(=O)NC1C(OC(C)=O)OC2COC(c3ccccc3)OC2C1OC(C)=O ; CC(=O)NC1C(OC(C)=O)OC(CO)C(O)C1OC(C)=O]

Starting material 1,3-di-O-acetyl-4,6-O-benzylidene-N-acetyl-D-galactosamine (230 g, 585 mmol) was dissolved in a mixture of MeOH/dioxane (1:1, 3 L), placed in a Parr vessel and AcOH (1.9 g, 1.77 mL, 31 mmol) was added. Subsequently, Pd—C(37.3 g, 175 mmol) was added and the vessel was fitted to Parr apparatus. The reaction was stirred overnight under H$_2$ atmosphere (5 bar). Subsequently, the mixture was filtered over a Celite pad and washed with 1,4-dioxane (1200 mL). Acetic acid (12 mL) was added to the filtrate followed by concentration under reduced pressure to yield product 3 (224 g, 126%). $^1$H NMR (400 MHz, DMSO) δ (ppm) 7.91 (d, J=8.4 Hz, 1H), 5.96 (d, J=3.6 Hz, 1H), 5.20 (d, J=5.2 Hz, 1H), 4.84 (dd, J=8.8, 2.8 Hz, 1H), 4.49-4.43 (m, 1H), 3.79 (t, J=6.4 Hz, 1H), 3.55-3.50 (m, 1H), 3.44-3.40 (m, 1H), 2.11 (s, 3H), 2.01 (s, 3H), 1.78 (s, 3H).

Example 1-4: Synthesis of 4,6-O-sulfoxyl-1,3-di-O-acetyl-N-acetyl-D-galactosamine (3a)

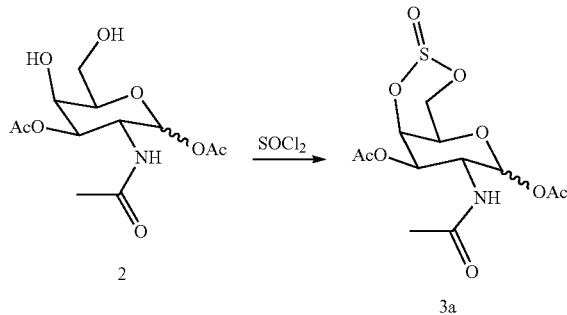 [SMILES: CC(=O)NC1C(OC(C)=O)OC(CO)C(O)C1OC(C)=O ; "SOCl2" ; CC(=O)NC1C(OC(C)=O)OC2COS(=O)OC2C1OC(C)=O]

Method A: Compound 2 (190 g, 622 mmol) was dissolved in DCM (11.5 L) and placed under an N$_2$ atmosphere. Next, SOCl$_2$ (182 mL, 933 mmol) was added dropwise and subsequent the reaction mixture was cooled to 0° C. followed by the slow addition of Et$_3$N (500 mL, 1306 mmol). Upon complete addition the reaction was warmed to room temperature and stirred for one hour. The reaction was quenched by careful addition of water (2.3 L). The layers were separated and the organic layer extracted twice more with water (2×2.3 L). The combined organic layers were dried over Na$_2$SO$_4$, filtered, and concentrated in vacuo. The crude product (4a) was used without further purification in the next step. $^1$H NMR (400 MHz, MeOD) δ (ppm) 6.23 (d, J=3.6 Hz, 1H), 5.34-5.35 (m, 1H), 5.24 (dd, J=8.4, 3.2 Hz, 1H), 4.94-0.495 (m, 1H), 4.63 (dd, J=8.4, 3.2 Hz, 1H), 4.11 (s, 1H), 3.96 (dd, J=10.8, 1.6 Hz, 1H), 2.17 (s, 3H), 2.07 (s, 3H), 1.95 (s, 3H).

Method B: Compound 2 (1 equiv.) was dissolved in EtOAc (0.15 M) and place under an N$_2$ atmosphere. SOCl$_2$ (1.05 equiv.) was added dropwise followed by the addition of pyridine (2.1 equiv.). The reaction progress was followed by TLC analysis (100% EtOAc) and full conversion was obtained after 30 minutes. The reaction was quenched by addition of H$_2$O (0.07 M) and EtOAc (0.03 M). The layers were separated and the aqueous layer extracted once more with EtOAc (0.03 M). The combined organic layers were dried over Na$_2$SO$_4$, filtered, and concentrated in vacuo. The crude product (3a) was used without further purification in the next step.

Example 1-5: Synthesis of 4,6-O-sulfonyl-1,3-di-O-acetyl-N-acetyl-D-galactosamine (3b)

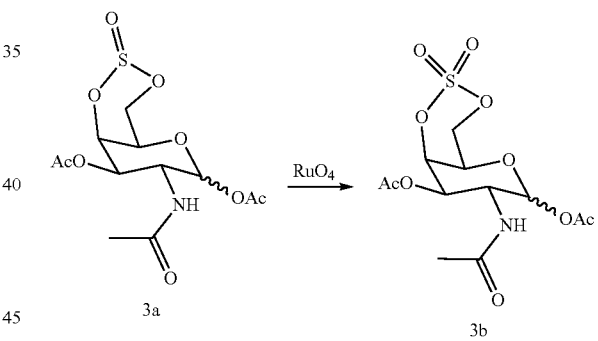

Crude 3a (176 g, 501 mmol) was dissolved in a mixture of DCM (1460 mL) and MeCN (1460 mL). Subsequently NaIO$_4$ (214 g, 1002 mmol) in water (2199 mL) and the mixture was stirred vigorously. A solution of RuCl$_3$.xH$_2$O (2.08 g, 10.0 mmol) in water (106 mL) was added dropwise and the reaction was cooled with an ice bath to prevent a further exothermic reaction. The reaction was stirred at room temperature for approximately 30 minutes (reaction progress was followed by TLC analysis (100% EtOAc)). Upon completion of the reaction (1 h), the reaction mixture was cooled to 5° C. with an ice/NaCl bath. Then, a solution of sodium metabisulfite (438 g, 2304 mmol) in water (704 mL) was added via dropwise addition over 45 minutes. The reaction mixture was transferred to a separation funnel and the layers separated. The aqueous layer was extracted twice more with DCM (850 mL). The combined organic layers were washed with half saturated NaCl solution and dried over Na$_2$SO$_4$, filtered and concentrated in vacuo. The white solid was triturated in diisopropyl ether (alternative: diethyl ether) (700 mL) overnight and subsequent filtrated and rinsed with an additional diisopropyl ether (3×200 mL) (alternative: diethyl ether). The solids were dried under a mild nitrogen flow to yield to product 3b (153 g, 416 mmol, 83%) as an off-white solid.

Work-up procedure B: Upon completion of the reaction, the mixture was diluted DCM (0.2 M). The reaction mixture was transferred to a separation funnel and the layers separated. The aqueous layer was extracted once with DCM (0.2 M). The combined organic layers were dried over Na$_2$SO$_4$, filtered (optional: perform the filtration over Celite) and concentrated in vacuo. Performing a gradient flash chromatography (DCM:MeOH; 100:0→90:10) yielded the purified product 3b (79-82%). $^1$H NMR (400 MHz, DMSO) δ (ppm) 8.07 (d, J=8.8 Hz, 1H), 6.07 (d, J=3.2 Hz, 1H), 5.45 (d, J=3.2 Hz, 1H), 5.25 (dd, J=8.0, 2.8 Hz, 1H), 4.83 (AB system, 36.4, 12.8 Hz, 2H), 4.42-4.37 (m, 2H), 2.15 (s, 3H), 2.09 (s, 3H), 1.83 (s, 3H).

Example 1-6: Synthesis of 6-azido-6-deoxy-1,3-di-O-acetyl-N-acetyl-D-galactosamine (1)

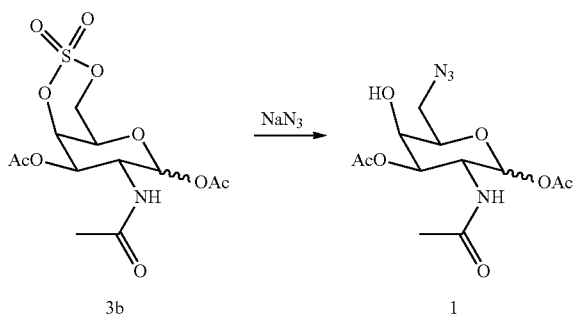 [SMILES: CC(=O)NC1C(OC(C)=O)OC2COS(=O)(=O)OC2C1OC(C)=O ; CC(=O)NC1C(OC(C)=O)OC(CN=[N+]=[N-])C(O)C1OC(C)=O ; "NaN3"]

Method A: Crude 3b (1 equiv.) was dissolved in DMF (0.1-0.2 M) and NaN$_3$ (1.2-5 equiv.) was added. The reaction mixture was stirred at room temperature, and was concentrated when finished (1-24 h, depending on the amount of NaN$_3$ used). The residue was dissolved in THF (0.2 M) and H$_2$SO$_4$ (1.2 equiv.) and H$_2$O (1.2 equiv.) were added. The reaction was stirred at room temperature (1-4 h) and analyzed with TLC (DCM:MeOH 9:1).

Work-up procedure: EtOAc (0.2 M), saturated aqueous NaHCO$_3$ solution (0.4 M) and water (0.4 M) were added. The water layer was extracted with EtOAc (2×0.2 M) and dried over Na$_2$SO$_4$, filtrated and concentrated under reduced pressure. The crude product 1, was obtained in 80-100% yield. NMR analysis indicated that partial acetyl migration from 3-OH to 4-OH had taken place, but the crude product 1 was used in the next step. Small scale separation of these two regioisomers by silica column chromatography gave pure samples of compound 1 and its regioisomer compound 1' (having a 3-OH and 4-OAc group) for NMR.

Purification: After concentration, gradient flash chromatography (DCM:MeOH; 100:0→90:10) yielded product 1 (61%).

$^1$H-NMR (400 MHz, CDCl$_3$) 3-OAc (compound 1): δ (ppm) 6.19 (d, J=3.6 Hz, 1H), 5.67 (d, J=9.3 Hz, 1H), 5.17 (dd, J=3.2, 8.4 Hz, 1H), 4.84-4.76 (m, 1H), 4.08 (s, 1H), 3.99 (t, J=6.4 Hz, 1H), 3.53 (ddd, J=6.4, 6.4, 8.8 Hz, 2H), 2.88 (d, J=3.6 Hz, 1H), 2.18 (s, 3H), 2.14 (s, 3H), 1.95 (s, 3H).

$^1$H-NMR (400 MHz, CDCl$_3$) 4-OAc (compound 1'): δ (ppm) 6.24 (d, J=3.6 Hz, 1H), 6.05 (d, J=8.0 Hz, 1H), 5.35 (d, J=2.8 Hz, 1H), 4.52 (ddd, J=3.2, 3.6, 4.8 Hz, 1H), 4.07 (dd, J=1.6, 5.2 Hz, 1H), 4.01-3.95 (m, 1H), 3.43-3.38 (m, 1H), 3.28-3.24 (m, 2H), 2.24 (s, 3H), 2.18 (s, 3H), 2.04 (s, 3H).

Method B: Crude 3b (150 g, 408 mmol, 1 equiv.) was dissolved in DMF (1500 mL) and NaN$_3$ (26.8 g, 412 mmol) was added. The reaction mixture was stirred at room temperature overnight, followed by the addition of 2-(bromomethyl)naphthalene (4.51 g, 20.4 mmol). The reaction was stirred for another hour and subsequent concentrated under reduced pressure. The residue was dissolved in THF (900 mL) and water (8.9 mL, 490 mmol) by heating in a water bath (40° C.). Subsequent the reaction was cooled in an ice bath and sulfuric acid (26.1 mL, 490 mmol) was added dropwise. The reaction was stirred for an hour at room temperature followed by addition of saturated aqueous NaHCO$_3$ (1.2 L) and the mixture was extracted with EtOAc (7×1 L). The combined organic layers were dried over Na$_2$SO$_4$, filtrated and concentrated under reduced pressure. The residue was dissolved in EtOAc (1 L) and dried over Na$_2$SO$_4$, filtrated and concentrated to afford crude 1 as a yellow oil. NMR analysis indicated that partial acetyl migration from 3-OH to 4-OH had taken place, but the crude product 1 was used in the next step. Small scale separation of these two regioisomers by silica column chromatography gave pure samples of compound 1 and its regioisomer compound 1' (having a 3-OH and 4-OAc group) for NMR.

$^1$H-NMR (400 MHz, CDCl$_3$) 3-OAc (compound 1): δ (ppm) 6.19 (d, J=3.6 Hz, 1H), 5.57 (d, J=9.2 Hz, 1H), 5.18 (dd, J=3.2, 8.4 Hz, 1H), 4.84-4.78 (m, 1H), 4.08 (s, 1H), 3.98 (t, J=6.4 Hz, 1H), 3.53 (ddd, J=6.4, 6.4, 8.8 Hz, 2H), 2.81 (d, J=3.6 Hz, 1H), 2.18 (s, 3H), 2.14 (s, 3H), 1.95 (s, 3H).

$^1$H-NMR (400 MHz, CDCl$_3$) 4-OAc (compound 1'): δ (ppm) 6.23 (d, J=3.6 Hz, 1H), 5.61 (d, J=8.0 Hz, 1H), 5.35 (d, J=2.8 Hz, 1H), 4.52 (ddd, J=3.2, 3.6, 4.8 Hz, 1H), 4.07 (dd, J=1.6, 5.2 Hz, 1H), 4.01-3.95 (m, 1H), 3.43-3.38 (m, 1H), 3.28-3.24 (m, 2H), 2.24 (s, 3H), 2.18 (s, 3H), 2.04 (s, 3H).

Example 1-7: Synthesis of 6-O-tosyl-1,3,4-tri-O-acetyl-N-acetyl-D-galactosamine (3c)

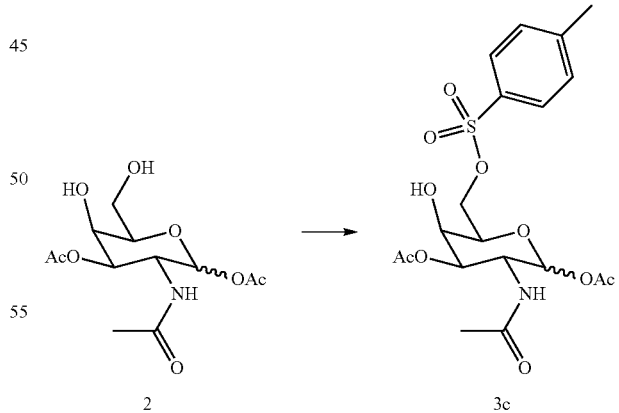

Compound 2 (1.3 g, 4.3 mmol) was dissolved in pyridine (20 mL), cooled to 0° C. and p-toluenesulfonyl chloride (989 mg, 5.2 mmol) was added. After 2 h, additional p-toluenesulfonyl chloride (380 mg, 2.4 mmol) was added and the reaction was stirred for another hour. The reaction mixture was concentrated under reduced pressure followed by the addition of DCM (50 mL) and 1 M HCl (30 mL). After separation of the layers the organic layer was washed with 1 M aqueous HCl (2×30 mL), dried over Na$_2$SO$_4$, filtrated and concentrated under reduced pressure. Purification by flash chromatography (DCM:MeOH=100:0→94:6) yielded product 3c (1.45 g, 3.1 mmol, 72%) as a white solid. $^1$H-NMR (400 MHz, CDCl$_3$): δ 7.77 (d, J=8.8 Hz, 2H), 7.34 (d, J=8.8 Hz, 2H), 6.11 (d, J=4 Hz, 1H), 5.54 (d, J=9.6 Hz, 1H), 5.17 (dd, J=2.8, 8.4 Hz, 1H), 4.77-4.71 (m, 1H), 4.27 (AB-system, J=3.2, 6.4 Hz, 1H), 4.06 (AB-system, J=3.2, 6.4 Hz, 1H) 4.16-4.13 (m, 2H), 2.46 (s, 3H), 2.17 (s, 3H), 2.11 (s, 3H), 1.93 (s, 3H).

Example 1-8: Synthesis of 1 by Nucleophilic Substitution of 3c with Azide, Followed by Acetylation To compound 3c (1.4 g, 3 mmol) in DMF (15 mL) were added NaN$_3$ (1 gram, 15 mmol), tetrabutylammonium iodide (575 mg, 1.5 mmol) and 15-crown-5 (341 mg, 1.5 mmol). The suspension was heated to 70° C. for 48 h followed by concentration under reduced pressure. The crude mixture was dissolved in pyridine (20 mL) followed by the addition of acetic anhydride (3 mL, mmol). The reaction was stirred overnight at room temperature. Next, DCM (30 mL) was added and the reaction mixture was washed with 1 M aqueous HCl (3×20 mL) and with saturated aqueous NaHCO$_3$ solution (2×20 mL). The organic layer was dried over Na$_2$SO$_4$, filtrated and concentrated under reduced pressure. Purification by flash chromatography (DCM:MeOH=100:0→95:5) yielded 1 (515 mg, 1.4 mmol, 47%). $^1$H-NMR (400 MHz, CDCl$_3$): δ 6.24 (d, J=4 Hz, 1H), 5.48-5.46 (m, 1H), 5.41-5.40 (m, 1H), 5.24-5.21 (m, 1H), 4.77-4.71 (m, 1H), 4.12-4.09 (m, 1H), 3.44 (AB-system, J=7.2, 5.6 Hz, 1H), 3.22 (AB-system, J=7.2, 5.6 Hz, 1H), 2.20 (s, 3H), 2.18 (s, 3H), 2.04 (s, 3H), 1.97 (s, 3H).

Example 1-9: Synthesis of 6-O-mesyl-1,3,4-tri-O-acetyl-N-acetyl-D-galactosamine (3d)

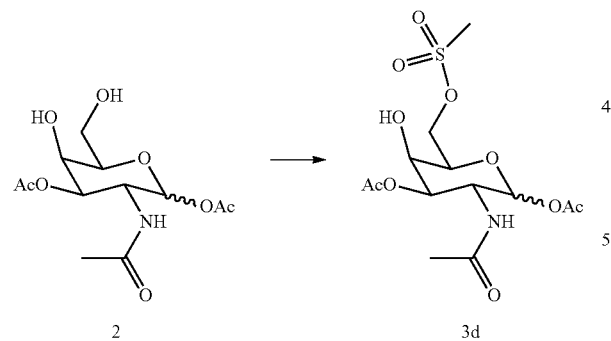

To a solution of compound 2 (100 mg, 0.327 mmol, 1.00 equiv.) in MeCN (0.5 mL) was added DCM (1.0 mL), Et$_3$N (63.0 μL, 0.452 mmol, 1.4 equiv.) and MsCl (27 μL, 0.349 mmol, 1.07 equiv.). The resulting reaction mixture was stirred at rt and monitored by TLC analysis. After stirring the reaction for 1 hour, TLC analysis showed incomplete conversion. Following this analysis, additional MsCl (10 μL) was added, followed by another addition of MsCl (10 μL) together with Et$_3$N (20 μL) after 1 more hour. After stirring the reaction mixture for another 30 minutes, DCM and sat. aq. NH$_4$Cl were added. The resulting mixture was shaken vigourisly and the resulting biphasic system was separated. The organic layer was washed with sat. aq. NH$_4$Cl (3×) and then dried (Na$_2$SO$_4$), filtered and conc. in vacuo. In addition, the combined water layers were extracted with EtOAc (3×) and the combined organic layers were dried (Na$_2$SO$_4$), filtered and conc. in vacuo. The resulting residue was combined with the residue from the DCM-extraction and purified by flash column chromatography (0-5% MeOH in DCM), affording compound 3d (40 mg, 32% yield). LCMS (ESI+) calculated for C$_{13}$H$_{21}$N$_4$O$_{10}$S$^+$ (M+Na$^+$) 406.08. found 405.95.

Example 1-10a: Synthesis of 1 by Nucleophilic Substitution of 3d with NBu$_4$N$_3$ To a mixture of 3d (20 mg, 49 μmol, 1.0 equiv.) in MeCN (200 μL) was added NBu$_4$N$_3$ (18 mg, 63 μmol, 1.3 equiv.), followed by heating to reflux. The mixture was refluxed over the weekend. The resulting mixture was refluxed over the weekend, showing the formation of compound 1. LCMS (ESI+) calculated for C$_{10}$H$_{15}$N$_4$O$_5$$^+$ (M-OAc$^-$) 271.1. found 271.23.

Example 1-10b: Synthesis of 1 by Nucleophilic Substitution of 3d with NaN$_3$

To a mixture of 3d (20 mg, 49 μmol, 1.0 equiv.) in DMF (200 μL) was added NaN$_3$ (16 mg, equiv.), followed by heating to reflux. The mixture was refluxed over the weekend, showing the formation of compound 1. LCMS (ESI+) calculated for C$_{10}$H$_{15}$N$_4$O$_5$$^+$ (M-OAc$^-$) 271.1. found 271.23.

Example 1-11: Synthesis of 1 by Substitution of 3d with Azide Under Mitsunobu Conditions

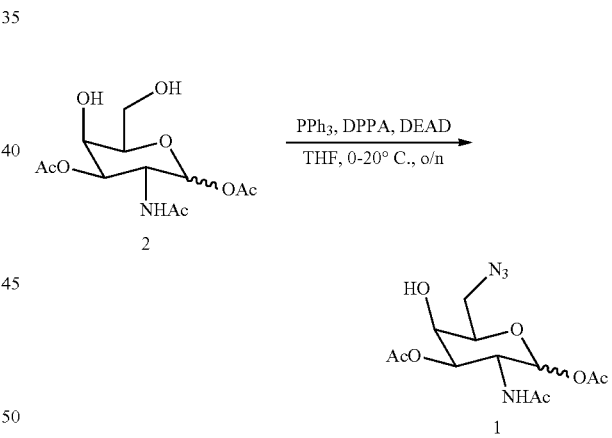

Compound 2 (50 mg, 0.16 mmol) was mixed with PPh$_3$ (58 mg, 0.22 mmol, 1.4 equiv.), diphenylphosphoryl azide (47 μL, 0.22 mmol, 1.4 equiv.) and diethyl azodicarboxylate (100 μL, 40 wt % solution in toluene, 0.22 mmol, 1.4 equiv.) were taken up in cold THF (1.0 mL) while cooling in an ice-bath. The reaction was left at 0° C. for 4 hours and then allowed to warm to rt. TLC-analysis indicated limited conversion. The reaction mixture was cooled to 0° C. and PPh$_3$ (30 mg, 0.13 mmol, 0.83 equiv.), diphenylphosphoryl azide (24 μL, 0.11 mmol, 0.71 equiv.) and diethyl azodicarboxylate (49 μL, 40 wt % solution in toluene, 0.11 mmol, 0.68 equiv.) were added. The resulting mixture was allowed to warm to rt and stirred overnight. Next, the reaction mixture was partially concentrated under reduced pressure and purified by silica gel column chromatography (DCM:

MeOH=100:0→95:5), affording crude compound 1 (38 mg). LCMS (ESI+) calculated for $C_{10}H_{15}N_4O_5^+$ (M-OAc⁻) 271.1. found 271.23.

Example 1-12: Synthesis of 6-azido-6-deoxy-1,3,4-tri-O-acetyl-N-acetyl-D-galactosamine (6)

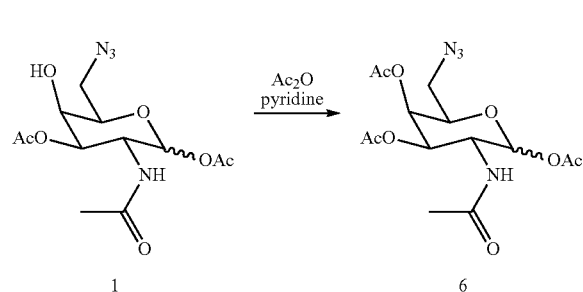 [SMILES: CC(=O)NC1C(OC(C)=O)OC(CN=[N+]=[N-])C(O)C1OC(C)=O ; "Ac2Opyridine" ; CC(=O)NC1C(OC(C)=O)OC(CN=[N+]=[N-])C(OC(C)=O)C1OC(C)=O]

Method A: Crude product 1 (152 g, 416 mmol) was dissolved in pyridine (750 mL) and acetic anhydride (236 mL, 2496 mmol) was added. The reaction was stirred at room temperature overnight and concentrated under reduced pressure. Next, EtOAc (1 L) was added and suspension was added to a stirred 1 M aqueous HCl solution (2.16 L). After vigorous stirring for 15 minutes, the layers were separated and the aqueous layer was extracted once more with EtOAc (1 L). The combined organic layers were washed with brine (2×1 L), dried over $Na_2SO_4$, filtrated and concentrated under reduced pressure. Subsequent diethyl ether (1.2 L) was added and heated to reflux. The mixture was mechanically stirred while allowing to cool down to room temperature. After stirring overnight the solids were filtrated and rinsed with diethyl ether (3×200 mL). After drying under a nitrogen stream product 6 (123 g, 333 mmol, 80% over 2 steps) was obtained as a white solid. Purification by flash chromatography (EtOAc:heptane; 50:50→100:0) yielded product 6 (77% over 5 steps) as a white solid. ¹H NMR (400 MHz, CDCl₃) δ (ppm) 6.24 (d, J=3.6 Hz, 1H), 5.57 (d, J=9.2 Hz, 1H), 5.41-5.40 (m, 1H), 5.21 (dd, J=8.4, 3.2 Hz, 1H), 4.76-4.70 (m, 1H), 4.12 (t, J=6.8 Hz, 1H), 3.43 (AB system, J=7.2, 5.6 Hz, 1H), 3.22 (AB system, J=7.2, 5.6 Hz, 1H), 2.20 (s, 3H), 2.19 (s, 3H), 2.04 (s, 3H), 1.96 (s, 3H).

Method B: Crude product 1 (9 mg, 0.03 mmol) was dissolved in DCM (0.02 M) and acetic anhydride (5 equiv.), DMAP (0.1 equiv.) and Et₃N (5 equiv.) were added. The reaction was stirred at room temperature for 3 h. Next, EtOAc (0.03 M) was added and the reaction mixture was washed with 1 M HCl (0.03 M) and saturated aqueous NaHCO₃ solution (0.03 M). The organic layer was dried over Na₂SO₄, filtered and concentrated under reduced pressure to yield product 6 (71%). ¹H NMR (400 MHz, CDCl₃) δ (ppm) 6.24 (d, J=3.6 Hz, 1H), 5.57 (d, J=9.2 Hz, 1H), 5.41-5.40 (m, 1H), 5.21 (dd, J=8.4, 3.2 Hz, 1H), 4.76-4.70 (m, 1H), 4.12 (t, J=6.8 Hz, 1H), 3.43 (AB system, J=7.2, 5.6 Hz, 1H), 3.22 (AB system, J=7.2, 5.6 Hz, 1H), 2.20 (s, 3H), 2.19 (s, 3H), 2.04 (s, 3H), 1.96 (s, 3H).

Example 2-1: Synthesis of 6-azido-6-deoxy-3,4-tri-O-acetyl-N-acetyl-D-galactosamine (11)

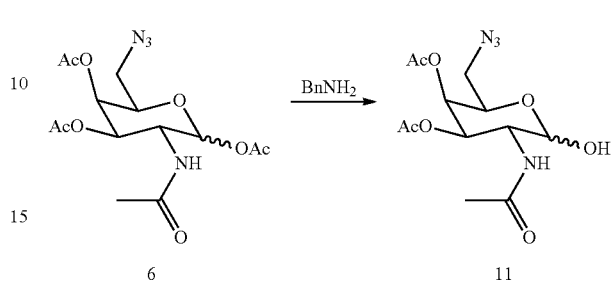

Method A: A solution of compound 6 (420 mg, 1.13 mmol) in dry THF (11 mL) was cooled to 0° C., followed by the addition of benzylamine (130 μL, 1.18 mmol, 1.04 equiv.) The resulting mixture was stirred at 0° C. for 2 hours and then conc. in vacuo. The residue was purified by flash chromatography (EtOAc:heptane; 60:40→100:0), affording 353 mg (95%) of compound 11. ¹H NMR (400 MHz, CDCl₃) δ (ppm) 6.24 (d, J=3.6 Hz, 1H), 5.74 (d, J=9.1 Hz, 1H), 5.44-5.37 (m, 1H), 5.25-5.18 (m, 1H), 4.77-4.65 (m, 1H), 4.16-4.08 (m, 1H), 3.49-3.38 (m, 1H), 3.28-3.15 (m, 1H), 2.18 (s, 3H), 2.03 (s, 3H), 1.95 (s, 3H).

Method B: A stirred solution of compound 6 (2.3 g, 6.18 mmol) in dry THF (40 mL) was treated with BnNH₂ (0.95 mL, 8.65 mmol, 1.4 eq) and the resulting mixture stirred until LCMS showed the reaction was complete, typically 18 h. The mixture was diluted with DCM (150 ml) and washed, in-turn, with saturated aq. NH₄Cl solution and Brine (100 mL each), dried (MgSO₄), filtered and concentrated. Flash-column chromatography (80 g SiO₂ cartridge; 50-100% EtOAc in petroleum ether 40-60) of the residue afforded compound 11 as a white foam (1.64 g, 4.96 mmol, 83% yield). NMR shows compound 11 is a 4:1 α/β anomeric mixture, and also contains BnNHAc (>5%).

Method C: A stirred solution of compound 6 (1.80 g, 4.83 mmol) in dry THF (24 mL) was treated with dimethylaminopropylamine (DMAPA, 0.9 mL, 7.2 mmol, 1.5 eq) and the resulting mixture stirred until LCMS shows the reaction is complete, typically 18 h. The yellow mixture was diluted with MeOH (75 ml) and treated with IR120 (H⁺ form) resin until LCMS showed DMAPA and its acetamide bi-product had disappeared (along with yellow color). Filtration, washing with MeOH and concentration of the filtrate afforded compound 11 as a white foam (1.64 g, 4.96 mmol, 92% yield). NMR shows compound 11 is a 4:1 α/β anomeric mixture.

Method D: A stirred solution of compound 6 (200 mg, 0.54 mmol) in dry THF (2.75 mL) was treated with DMAPA (0.1 mL, 0.81 mmol, 1.5 eq) and the resulting mixture stirred until LCMS shows the reaction is complete, typically 18 h. The yellow mixture was diluted with DCM (40 ml) and washed, in-turn, with 1M HCl and brine (15 mL each) and dried (MgSO₄). Filtration and concentration afforded compound 11 as a white foam (130 mg, 0.39 mmol, 73% yield). NMR shows compound 11 is a 4:1 α/β anomeric mixture and contains also residues of THF (~10%).

Example 2-2: Synthesis of (3aR,5R,6S,7R,7aR)-5-(azidomethyl)-2-methyl-3a,6,7,7a-tetrahydro-5H-pyrano[3,2-d]oxazole-6,7-diyl diacetate (7)

Method A

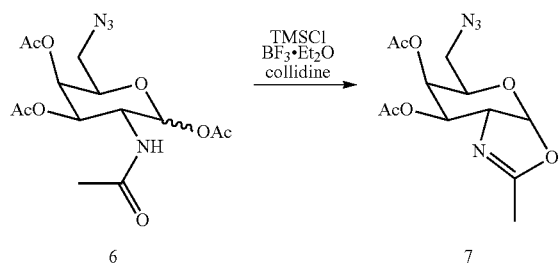 [SMILES: CC(=O)NC1C(OC(C)=O)OC(CN=[N+]=[N-])C(OC(C)=O)C1OC(C)=O ; "TMSClBF3·Et2Ocollidine" ; CC(=O)OC1C(CN=[N+]=[N-])OC2OC(C)=NC2C1OC(C)=O]

The reaction was performed in a three neck, 1000 ml flask, which was dried in an oven >100° C. overnight and flushed with nitrogen prior to use. In this flask, compound 6 (16.6 g, 44.6 mmol) was dissolved in dry dichloromethane (500 mL). To this solution 2,4,6-collidine (10 ml, 80 mmol) was added slowly via syringe. The reaction mixture was stirred for 10 minutes and to this clear solution, bromotrimethylsilane (10 ml, 76 mmol) was added slowly via dropping funnel. After 5 minutes, boron trifluoride etherate (ca. 48% $BF_3 \cdot Et_2O$ 20 mL, 158 mmol) was added via dropping funnel. After 10 minutes, the mixture was heated to 35° C. and stirred for 5 h. Then a TLC analysis (DCM:MeOH 93:7) showed almost full conversion. The heating was switched off and the mixture was allowed to reach room temperature overnight. TLC analysis showed full consumption of the starting material. The mixture was cooled down to 0° C. in an ice-bath and poured slowly and under gentle stirring into 1000 mL ice-cooled saturated $NaHCO_3$ solution. Significant $CO_2$-evolution was observed. The layers were separated and the water layer extracted two additional times (2×500 ml DCM). The organic layer was combined, dried over $Na_2SO_4$ and was concentrated under reduced pressure. The mixture was coated on hydromatrix (inert diatomaceous earth sorbent, 40 gram) and purified by flash column chromatography (heptane:EtOAc=70:30→0:100 with 1% $Et_3N$), affording compound 7 (13.1 g, 39.2 mmol, 88% yield) as an off-white solid. $^1$H-NMR (400 MHz, $CDCl_3$): δ 6.02 (d, J=7.2 Hz, 1H), 5.40 (t, J=3.2 Hz, 1H), 4.95 (dd, J=3.6, 3.6 Hz, 1H), 4.13-4.09 (m, 1H), 4.06-4.03 (m, 1H), 3.48 (AB system, J=5.2, 7.6 Hz, 1H), 3.27 (AB system, J=5.2, 8 Hz, 1H), 2.14 (s, 3H), 2.08 (s, 3H), 2.07-2.04 (m, 3H).

Alternative work-up procedure: The reaction mixture was cooled with an ice bath and subsequently $Et_3N$ (5 equiv.) was added. After stirring for 5 minutes the resulting reaction mixture was put directly on a silica column and purified by flash column chromatography (heptane: EtOAc 50:50→10:90). After concentration of appropriate column fractions, the residue was dissolved in DCM (0.1 M) and washed with 2% aqueous citric acid (2×0.2 M). The organic layer was dried over $Na_2SO_4$, filtrated and concentrated under reduced pressure to afford compound 7 (87-89% yield) as a yellow oil.

Extraction procedure for selective removal of collidine: The crude reaction mixture was conc. in vacuo and redissolved in EtOAc (100 mL). The resulting suspension was filtered and the fitrate was washed with 5% aq. $CuSO_4$ (3×100 mL). The organic layer was washed with brine, dried ($Na_2SO_4$) and concentrated in vacuo. The residue may be used crude in the next step or may be purified by silica gel column chromatography (heptane:EtOAc=70:30→0:100 with 1% $Et_3N$), affording compound 7 (1.31 g, 95% pure by qNMR, 58% yield).

Method B

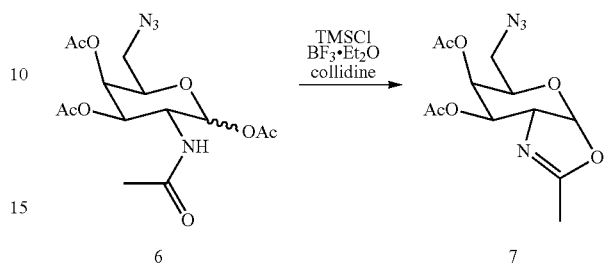

To a flame-dried round-bottom containing a stirrer and molecular sieves was added compound 6 (201 mg, 0.540 mmol, 1.00 equiv.), followed by dichloromethane (6.0 mL). The resulting solution was cooled to 0° C. and 2,4,6-collidine (220 µL, 1.62 mmol, 3.0 equiv.), chlorotrimethylsilane (206 µL ml, 1.62 mmol, 3.0 equiv.) and boron trifluoride etherate (210 µL, 1.62 mmol, 3 equiv.) were added sequentially. The resulting mixture was heated to 35-40° C. for 23 hours. The reaction was then cooled to 0° C. and quenched with $Et_3N$ (375 µL, 2.70 mmol, 5.0 equiv.). The resulting mixture was stirred for 5 minutes and then purified directly by silica gel column (pentane:EtOAc=50:50→10:90), affording compound 7 (137 mg, 93% pure by 1H-NMR, 76% yield) as a yellow oil. $^1$H NMR ($CDCl_3$): 6.02 (d, J=7.1 Hz, 1H), 5.40 (t, J=3.2 Hz, 1H), 5.02-4.89 (m, 1H), 4.19-4.07 (m, 1H), 4.07-3.93 (m, 1H), 3.55-3.43 (m, 1H), 3.32-3.20 (m, 1H), 2.14 (s, 3H), 2.08 (s, 3H), 2.07-2.03 (m, 3H).

Method C

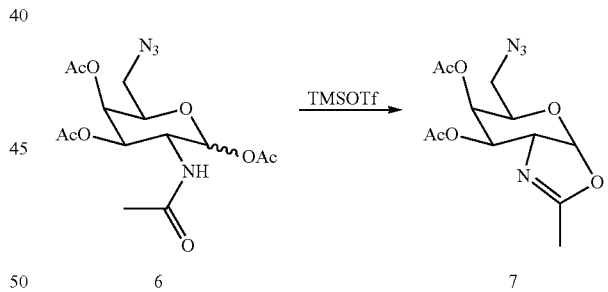

To a solution of compound 6 (1 equiv.) in dry 1,2-dichloroethane (0.1 M) was added TMSOTf (1.5 equiv.) at room temperature under $N_2$ atmosphere. The resulting reaction mixture was heated to 50° C. and the reaction was monitored by TLC (DCM:MeOH 9:1) until complete (optionally additional TMSOTf is added, up to 3 equiv.). After TLC-analysis indicated complete conversion (4-16 h), the reaction mixture was cooled to 0° C., followed by the dropwise addition of $Et_3N$ (1.5-5 equiv.) over 2 minutes and stirred for an extra 10 minutes. The resulting reaction mixture was purified directly by silica gel column chromatography (heptane:EtOAc=50:50→10:90 with 1% $Et_3N$), affording compound 7 (62-90% yield) as a light yellow oil. $^1$H NMR ($CDCl_3$): 6.02 (d, J=7.1 Hz, 1H), 5.40 (t, J=3.2 Hz, 1H), 5.02-4.89 (m, 1H), 4.19-4.07 (m, 1H), 4.07-3.93 (m, 1H), 3.55-3.43 (m, 1H), 3.32-3.20 (m, 1H), 2.14 (s, 3H), 2.08 (s, 3H), 2.07-2.03 (m, 3H).

Example 3-1a: Synthesis of dihydrophosphoryl 6-azido-6-deoxy-3,4-tri-O-acetyl-N-acetyl-d-galactosaminopyranose (5a) in Neat Phosphoric Acid

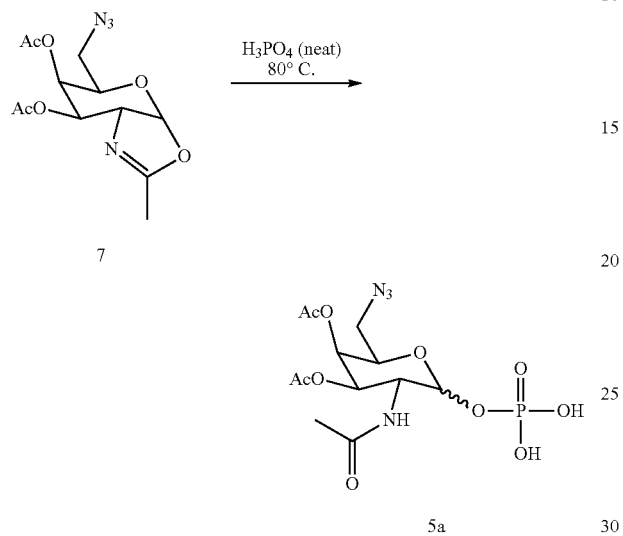

5a

Compound 7 (4 g, 10.7 mmol) was put under N$_2$ atmosphere and subsequently phosphoric acid (8.5 g, 91 mmol, pre-dried over P$_2$O$_5$) was added. The reaction was placed under vacuum over P$_2$O$_5$ and heated to 60° C. After 5 h the reaction was cooled to room temperature and THF (50 mL) was added. Subsequent the mixture was cooled to 0° C. and neutralized with aqueous NH$_4$OH until pH 7. The solids were removed by filtration, rinsed with THF and the filtrate was concentrated under reduced pressure. Purification by flash chromatography (MeCN:MeOH=100:0→50:50) yielded product 5a (888 mg, 2.2 mmol, 20%) with an α:β ratio of 1:1. $^1$H-NMR (400 MHz, CDCl$_3$): δ 5.47-5.44 (m, 1H), 5.35-5.34 (m, 1H), 5.25-5.24 (m, 1H), 5.11 (dd, J=3.2, 8.7 Hz, 1H), 5.03 (t, J=8.4 Hz, 1H), 4.97 (dd, J=3.2, 8 Hz, 1H), 4.41-4.36 (m, 1H), 4.27-4.30 (m, 1H), 4.09-4.04 (m, 1H), 3.84-3.80 (m, 1H), 3.49-3.38 (m, 4H), 2.07-2.06 (m, 6H), 1.88-1.85 (m, 12H).

TABLE 1

α:β ratio of 5 formed at various temperatures and reaction times in neat phosphoric acid

| | α:β ratio | | |
|---|---|---|---|
| temperature | reaction time = 16 h | reaction time = 40 h | reaction time = 132 h |
| 50° C. | 4.5:2.4 | 4.5:1.6 | 5.5:0.5 |
| 70° C. | 3.5:0.3 | 3:0.2 | N.D. |
| 90° C. | 3.5:0.2 | 3.2:0.2 (messy) | N.D. |

Example 3-1b: Synthesis of dihydrophosphoryl 6-azido-6-deoxy-3,4-tri-O-acetyl-N-acetyl-d-galactosaminopyranose (5a) in with Phosphoric Acid in DMF

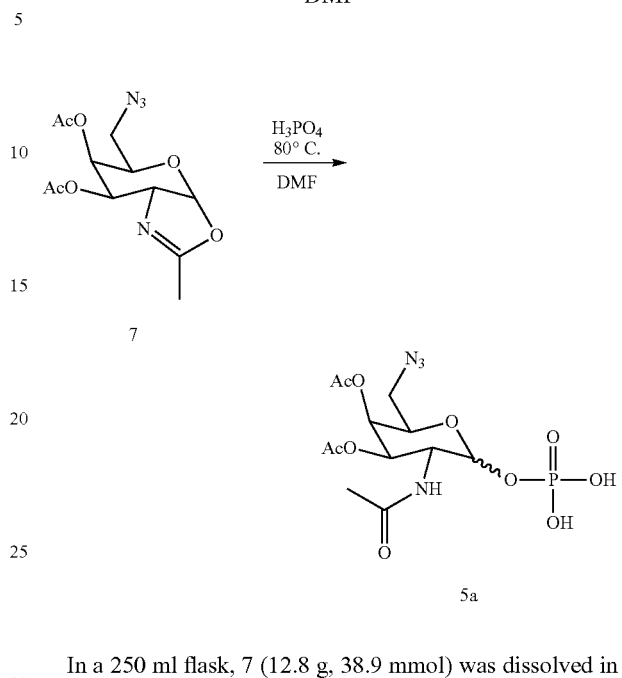

5a

In a 250 ml flask, 7 (12.8 g, 38.9 mmol) was dissolved in dry DMF (80 ml) and phosphoric acid (2.58 M solution in DMF, 91 ml, 234 mmol) was added via a syringe. The solution was reacted overnight at 80° C. $^1$H-NMR analysis (in CD$_3$OD) showed full consumption of the starting material and formation of predominantly the desired α-anomer of 5a. The reaction mixture was concentrated under reduced pressure and coated on hydromatrix (inert diatomaceous earth sorbent, 40 gram) and purified on C18 column silica gel column (water:MeCN 100:0→90:10 with 0.1% HCOOH). The combined batches containing the product were concentrated under reduced pressure and stripped 3 times with toluene to yield product 5a (10.1 g, 23.3 mmol, 60% yield) as a white solid. $^1$H-NMR (400 MHz, MeOD): δ 5.68-5-65 (m, 1H), 5.48-5.47 (m, 1H), 5.18 (dd, J=8.8, 2.8 Hz, 1H), 4.48-4.45 (m, 1H), 4.34-4.33 (m, 1H), 3.48 (AB system, J=6.8, 6 Hz, 1H), 3.34-3.30 (m, 1H, partly covered by solvent peak), 2.16 (s, 3H), 1.96 (s, 3H), 1.95 (s, 3H).

Alternative work-up: The reaction mixture was concentrated under reduced pressure followed by the addition of DCM (0.03 M) and MeOH (0.15 M) and 4-methylmorpholine (3.5 equiv.). Water (0.03 M) was added and the organic layer was extracted with water (3×0.03 M). The combined water layers were washed with EtOAc (3×0.03 M), concentrated and the residue was dissolved a small amount of MeOH followed by the addition of MeCN (0.05 M) and a precipitate was formed. The mixture was centrifuged at 10.000 rpm for 5 minutes Concentration of the liquid afforded compound 5a (53-76%) as an off-white solid.

Alternative work-up: After heating the reaction mixture at 80° C. for 24 h, the reaction was allowed to cool to rt and Et$_3$N (6.2 equiv.) was added and the solution was concentrated in vacuo. The residue was dissolved in 5% MeCN in water (0.1 M) and purification on silica-C18 (gradient 16-34% B, A=water, B=30% MeCN in water) afforded compound 5a (56%) as a fluffy white solid.

Alternative work-up: After heating the reaction mixture at 80° C. for 24 h, the reaction was conc. in vacuo. The thick brown syrup was taken up in a mixture of DCM and MeOH (82:18 ratio, 0.07M), followed by the addition of 4-methyl morpholine (6.4 equiv.). The mixture was then conc. in vacuo and the resulting residue was taken-up in a minimal amount of EtOAc/MeOH/H$_2$O (6/2/1). The suspension was transferred onto a silica column followed by purification by flash column chromatography (using a step-wise gradient going from 6/2/1→2/2/1 EtOAc/MeOH/H$_2$O). Compound 5a (59% yield) was obtained as a brown solid. $^1$H NMR (400 MHz, CD$_3$OD) δ (ppm): 5.70-5.60 (m, 1H), 5.49 (d, J=2.3 Hz, 1H), 5.23 (dd, J=11.4 Hz, 3.0 Hz, 1H), 4.54-4.45 (m, 1H), 4.45-4.35 (m, 1H), 3.57-3.46 (m, 1H), 3.40-3.34 (m, 1H), 2.20 (s, 3H), 2.03-1.96 (m, 6H).

Method B (less phosphoric acid in DMF and IEX-purification): To a flame-dried roundbottom containing a stirring bar was added compound 7 (2.1 g, 6.37 mmol, 1 equiv.), followed by dry DMF (2.72 mL). The resulting light-yellow solution was stirred at rt, followed by the addition of a 6.6 M solution of H$_3$PO$_4$ in dry DMF (1.93 mL, 12.73 mmol, 2.0 equiv.). The resulting reaction mixture was heated to 80° C. (by placement in a pre-heated oil-bath) under N$_2$ and stirred for 135 minutes. Note: before workup a sample should be analyzed by $^1$H NMR to assess if the α:β ratio is 210:1, which is typically achieved after 135 minutes. To this end, dissolve ~20 μL of reaction mixture in 0.5 mL MeOD-d$_3$). When the above ratio was achieved, the RM was allowed to cool to rt and then quenched by adding the reaction mixture to a stirred solution of aqueous 20 mM NH$_4$HCO$_3$ (1.27 L, 4 equiv.). Any remaining product can be removed from the reaction vessel by washing with dry DMF (a few mL), which may then be added to the aq. NH$_4$HCO$_3$ solution. The resulting solution is then loaded onto 300 mL Q-Sepharose Fast Flow® ion exchange column (A: 10 mM ammonium bicarbonate, B: 250 mM ammonium bicarbonate) at 10 ml/min. Then the column was washed with 10 mM ammonium bicarbonate solution followed by a gradient to 40% B to elute the product. Fractions containing the product were concentrated in vacuo to remove most of the buffer followed by overnight lyophilization of the remaining buffer to yield the 6-N$_3$-GalNAc-monophosphate (5a, 1.85 g, corrected 1.56 g (based on qNMR), 0.41 mmol, 58.1% yield) as an off-white solid. $^1$H NMR (400 MHz, CD$_3$OD) δ (ppm): 5.70-5.60 (m, 1H), 5.49 (d, J=2.3 Hz, 1H), 5.23 (dd, J=11.4 Hz, 3.0 Hz, 1H), 4.54-4.45 (m, 1H), 4.45-4.35 (m, 1H), 3.57-3.46 (m, 1H), 3.40-3.34 (m, 1H), 2.20 (s, 3H), 2.03-1.96 (m, 6H).

Example 3-2: Preparation of 5a' (NBu$_3$ Salt of 5a) by Quench with NBu$_3$

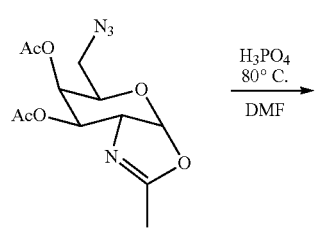

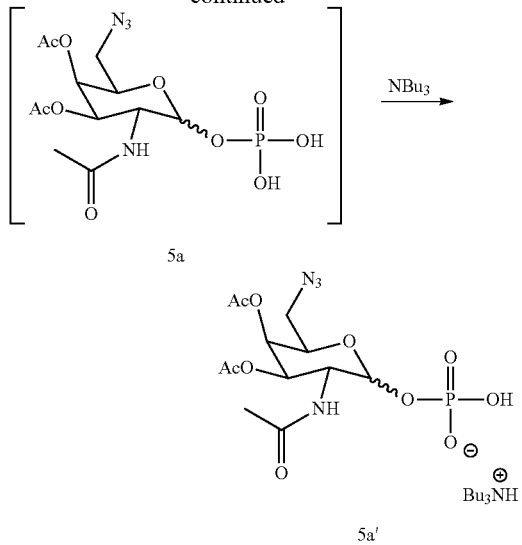

Method A: After heating the reaction mixture at 80° C. for 24 h, the reaction was allowed to cool to rt and Bu$_3$N (6.2 equiv.) was added and the solution was concentrated in vacuo. The residue was dissolved in 5% MeCN in water (0.1 M) and purification on silica-C18 (gradient 16-100% B, A=water, B=30% MeCN in water) afforded compound 5a' (117 mg, 44% pure by 1H-NMR, 37% yield) as a yellow oil.

Similarly, a quench with Et$_3$N, 4-methylmorpholine or NH$_4$HCO$_3$ afforded the respective salts of compound 5a, in the same way as described in Example 3-1.

Example 3-3: Deacetylation of Compound 5a to Give Compound 5b

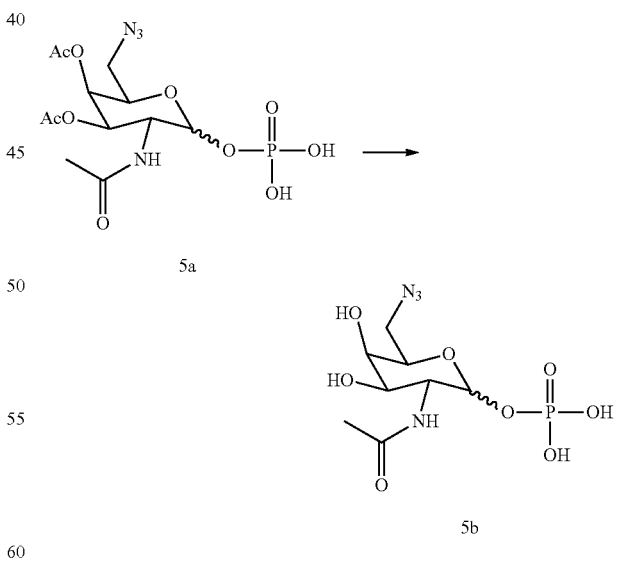

To a suspension of the acetylated sugar 5a (4.9 g, 11.9 mmol) in MeOH (15 mL), was added 25% aq. NH$_4$OH (60 mL). The reaction was allowed to stir at room temperature and the conversion monitored with LCMS. After 4 h, the mixture was concentrated under reduced pressure and stored at −20° C. for 2 d. The solid was then dissolved in 25% aq.

NH$_4$OH (75 mL), stirred at room temperature and after 3 h, MS showed complete conversion. Concentration of the solvent gave the crude product 5b (3.2 g, 9.9 mmol, 83%) as a yellow solid. $^1$H-NMR (400 MHz, D$_2$O): δ 5.28 (dd, J=7.2, 3.2 Hz, 1H), 4.12 (dd, J=6.8, 6.4 Hz, 1H), 4.06 (ddd, J=10.8, 3.2, 2.0 Hz, 1H), 3.92-3.81 (m, 2H), 3.47 (AB system, J=12.8, 7.2 Hz, 1H), 3.40 (AB system, J=12.8, 6.4 Hz, 1H), 1.88 (s, 3H).

Example 4-1: Exchange of UMP Disodium Salt to UMP Tributylammonium Salt (UMP.NBu$_3$)

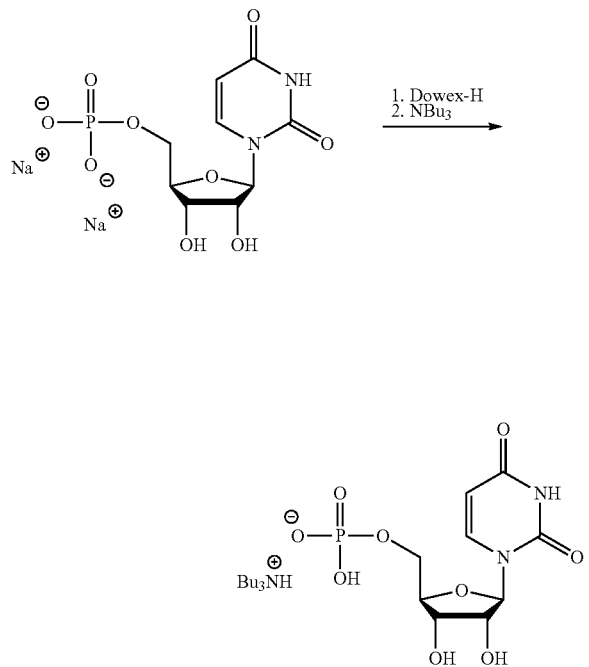

Dowex® 50WX8 50-100 mesh (250 g) was placed in a 500 mL glass filter and washed with demi water (3×, 500 mL). Then it was mixed with a solution of UMP disodium salt (40.0 g, 108 mmol) in water (250 ml) and the resulting suspension was stirred for 2 h at room temperature. Dowex® 50WX8 50-100 mesh was removed by filtration and rinsed with demi water (3×, 30 ml). To the resulting filtrate, tributylamine (25.9 ml, 108 mmol) was added and the mixture was vigorously stirred for 60 minutes. The clear solution was lyophilized overnight and then dried over P$_2$O$_5$ overnight. The resulting batch of UMP tributylammonium salt (25.9 g, 91% purity by $^1$H-qNMR, 80% yield) was obtained as a white solid. $^1$H NMR (400 MHz, D$_2$O) δ (ppm) 7.79 (d, 1H, J=8 Hz), 5.81 (d, 1H, J=4.4 Hz), 5.77 (d, 1H, J=8 Hz), 4.6-4.22 (m, 2H), 4.07-4.02 (m, 1H), 3.97-3.93 (m, 1H), 3.00-2.95 (m, 6H), 1.55-1.47 (m, 6H), 1.22 (sex, 6H, J=7.2 Hz), 0.77 (t, 9H, J=7.2 Hz).

Example 4-2: Synthesis of Mixture of UDP Derivatives 8 and 8' from 5a

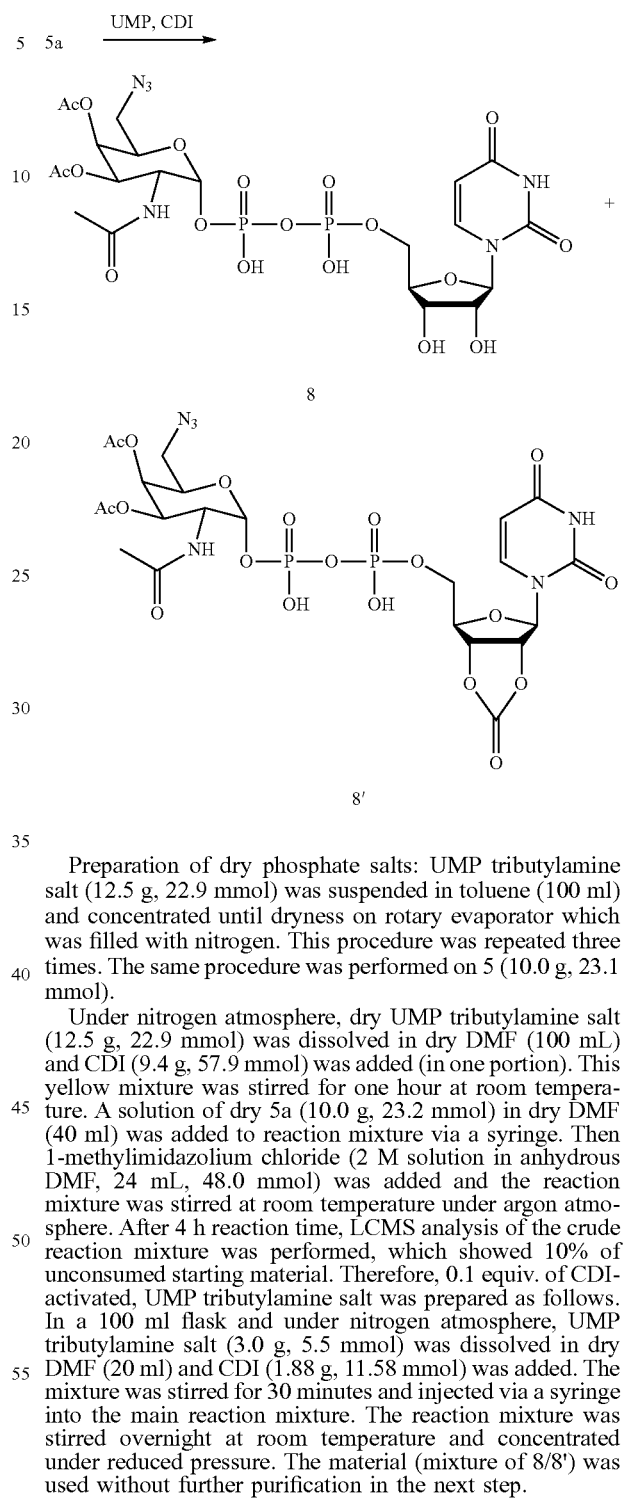

Preparation of dry phosphate salts: UMP tributylamine salt (12.5 g, 22.9 mmol) was suspended in toluene (100 ml) and concentrated until dryness on rotary evaporator which was filled with nitrogen. This procedure was repeated three times. The same procedure was performed on 5 (10.0 g, 23.1 mmol).

Under nitrogen atmosphere, dry UMP tributylamine salt (12.5 g, 22.9 mmol) was dissolved in dry DMF (100 mL) and CDI (9.4 g, 57.9 mmol) was added (in one portion). This yellow mixture was stirred for one hour at room temperature. A solution of dry 5a (10.0 g, 23.2 mmol) in dry DMF (40 ml) was added to reaction mixture via a syringe. Then 1-methylimidazolium chloride (2 M solution in anhydrous DMF, 24 mL, 48.0 mmol) was added and the reaction mixture was stirred at room temperature under argon atmosphere. After 4 h reaction time, LCMS analysis of the crude reaction mixture was performed, which showed 10% of unconsumed starting material. Therefore, 0.1 equiv. of CDI-activated, UMP tributylamine salt was prepared as follows. In a 100 ml flask and under nitrogen atmosphere, UMP tributylamine salt (3.0 g, 5.5 mmol) was dissolved in dry DMF (20 ml) and CDI (1.88 g, 11.58 mmol) was added. The mixture was stirred for 30 minutes and injected via a syringe into the main reaction mixture. The reaction mixture was stirred overnight at room temperature and concentrated under reduced pressure. The material (mixture of 8/8') was used without further purification in the next step.

Example 4-3: Silica Gel Separation of Mixture of 8 and 8' to Obtain Pure Sample of 8'

The crude reaction mixture was resuspended in a minimal amount of eluent (EtOAc:MeOH:water 8:2:1). To this a minimal amount of methanol was added to dissolve the product and the mixture was purified by flash column chromatography (EtOAc:MeOH:water 8:2:1→2:2:1), affording compound 8' (14.2 g, 15.5 mmol, 67% yield) as an off-white solid. $^{1}$H-NMR (400 MHz, D$_2$O): δ 7.63 (d, J=8 Hz, 1H), 5.91 (s, 1H), 5.76-5.74 (m, 1H), 5.55-5.50 (m, 2H), 5.38-0.5.34 (m, 2H), 5.12-5.09 (m, 1H), 4.38-4.35 (m, 2H), 4.16-4.09 (m, 3H), 3.43 (AB system, J=6.4, 6.4 Hz, 1H), 3.26 (AB system, J=6.4, 6.4 Hz, 1H), 2.10 (s, 3H), 1.88 (s, 3H), 1.87 (s, 3H).
Example 4-4: Selective Hydrolysis of Mixture 8 and 8' and Flash C18 Purification to Obtain 8, Followed by Deprotection to Obtain Pure 9a
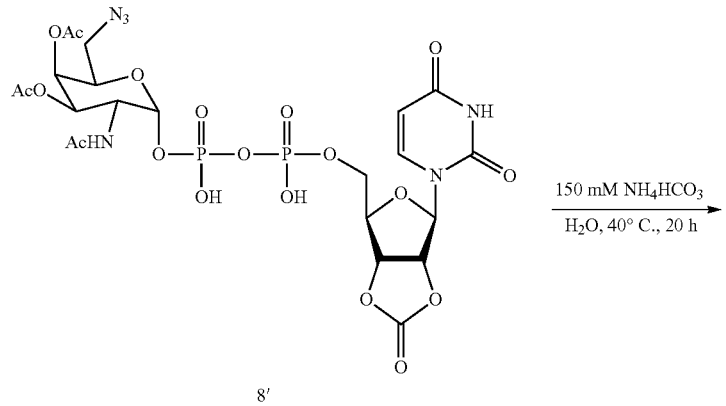
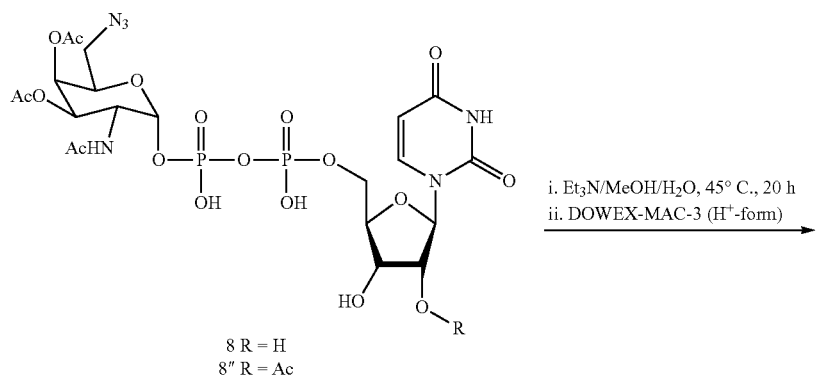
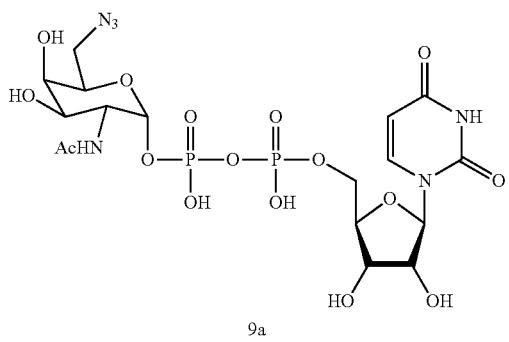

To a roundbottom flask containing crude 8' (808 µmol based on amount 5a used in the previous step) was added H₂O (37 mL), which is left for a few minutes to allow H₂O to react with any remaining CDI. To the resulting suspension was added NH₄HCO₃ (436 mg, 5.51 mmol, 6.8 equiv.), generating a 150 mM aq. solution of NH₄HCO₃. The reaction mixture was then heated to 40° C. for 20 h. The reaction progression was monitored by HPLC, which showed complete conversion after stirring overnight (20 h). Following complete conversion, the RM was conc. in vacuo to afford crude 8, which was then purified according to the flash C18 column chromatography protocol discussed below.

Crude 8 (0.834 mmol based on amount 5a during the UMP-coupling) was dissolved in 4 mL 5% MeCN in 200 mM aq. Et₃N·HOAc (190 mM effectively). The resulting solution was then conc. in vacuo and the residue was re-dissolved in 4 mL 5% MeCN in 200 mM aq. Et₃N·HOAc. This solution was purified by flash C18 column chromatography by using a 25 g C18 cartridge (5% MeCN in 190 mM aq. Et₃N·HOAc→30% MeCN in H₂O). The corresponding pure fractions were combined and conc. in vacuo, affording an orange oil. The material (a mixture of 8 and small amounts of 8" and 8'") were used without further purification in the next step.

To a roundbottom flask containing flash C18-purified 8 (2.87 g, 269 mg corrected (qNMR), 0.375 mmol) in H₂O (12 mL) was added MeOH (12 mL) and Et₃N (12 mL). The resulting solution was heated to 45° C. for 22 h and then conc. in vacuo, affording 2.748 g of a yellow oil. The residue was then subjected to a Dowex-treatment as described below.

To a roundbottom flask containing crude 9a (2.75 g, ~9% 9a and ~40% AcOH (¹H-NMR)) in H₂O (27.5 mL) was added Dowex MAC-3 hydrogen form (16.5 g). The resulting suspension was stirred at rt for 90 min. and the filtered over a P3 glassfilter. The residue was washed with H₂O (3×25 mL). The filtrate was concentrated in vacuo. The resulting residue (984 mg) was co-vaped with H₂O (1×20 mL), affording 9a (703 mg, 32.2% pure by qNMR) as a yellow oil. ¹H-NMR (400 MHz, D₂O): δ 7.82 (d, J=8.4 Hz, 1H), 5.85-5.78 (m, 2H), 5.40 (dd, J=3.6, 3.6 Hz, 1H), 4.25-4.18 (m, 3H), 4.16-4.02 (m, 5H), 3.89-3.86 (m, 1H), 3.86-3.80 (m, 1H), 3.45 (AB system, J=7.6, 5.2 Hz, 1H), 3.34 (AB system, J=7.2, 5.6 Hz, 1H), 1.94 (s, 3H).

Example 4-4: Synthesis of 9a (triethylammonium salt) by deacetylation of mixture of 8 and 8'

Method A: Crude product 8/8' was dissolved in water (0.15 M), methanol (0.15 M) and triethylamine (0.15 M) and stirred overnight. Next, the mixture was concentrated under reduced pressure and purified on Q agarose. First the mixture was diluted with water (0.02 M) and buffer A (NH₄HCO₃, 10 mM, 0.005 M) and subsequent loaded on Q agarose (100 mL resin/mmol starting material) with buffer A. Via a stepwise gradient (first to 10% B (250 mM NH₄HCO₃) in 20 minutes, then to 40% B in 120 minutes) the product was separated from the byproducts. Lyophilizing product fractions from yielded UDP-6-azidoGalNAc triethylammonium salt (9a). This intermediate was taken up in H₂O (0.2 M) and purified by C₁₈-HPLC using a Phenomenex Luna 10u C18 (2), 250×50 mm column (A: 50 mM Et₃N·HOAc, pH 6.8, B: MeCN). The collected fractions were combined and co-evaporated several times with H₂O and finally lyophilized to afford UDP-6-N₃-GalNAc (9a) as a brittle off-white solid (53%, starting from mixture of 8 and 8').

Method B: In a 1 L, one neck flask 8' (14.0 g, 15.3 mmol) was dissolved in Et₃N/MeOH/water (300 mL, 1:1:1) solution and stirred overnight at room temperature. The crude mixture was partially concentrated under reduced pressure up to 23 gram of 9 (37% purity by 1H-qNMR, 88% yield) and dissolved in 140 ml water. This solution of 9a was subjected to preparative LCMS (eluent 0-4% ACN in 50 mM Et₃N·HOAc in water, pH=6.8). The fractions containing product were combined to yield 9 (9 L solution in 50 mM Et₃N·HOAc buffer). The combined fractions (9 L) were divided in two portions and one portion (4.5 L) was loaded onto 1 L Q-Sepharose Fast Flow® ion exchange column (A: 25 mM ammonium bicarbonate, B: 250 mM ammonium bicarbonate) at 30 mL/min. Then the column was washed with 25 mM ammonium bicarbonate solution followed by a gradient to 100% B to elute the product. The product fractions were pooled and concentrated under reduced pressure to yield compound 9. This procedure was repeated to yield UDP-6"-N₃-6"-deoxy-GalNAc (9, ammonium-salt) (8.79 g, 92% purity by ¹H-qNMR, 12.8 mmol, 84% yield). ¹H-NMR (400 MHz, D₂O): δ 7.82 (d, J=8.4 Hz, 1H), 5.84-5.81 (m, 2H), 5.39 (dd, J=3.6, 3.6 Hz, 1H), 4.26-4.20 (m, 3H), 4.16-4.08 (m, 5H), 3.89-3.85 (m, 1H), 3.85-3.81 (m, 1H), 3.44 (AB system, J=7.6, 5.2 Hz, 1H), 3.33 (AB system, J=7.2, 5.6 Hz, 1H), 1.93 (s, 3H).

Example 4-4. Coupling of 5b with UMP Tributyl Ammonium Salt with CDI

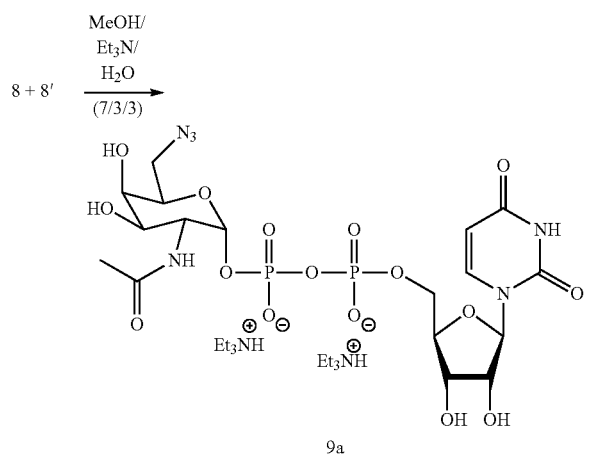

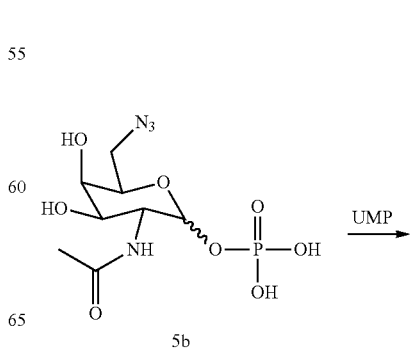

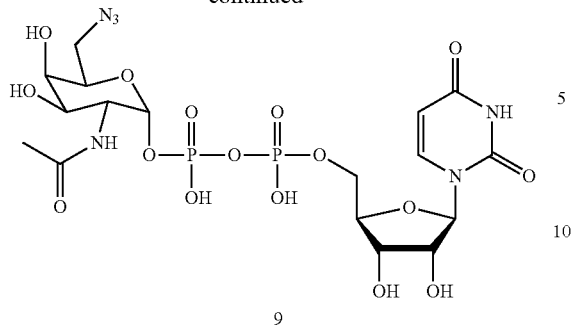

9

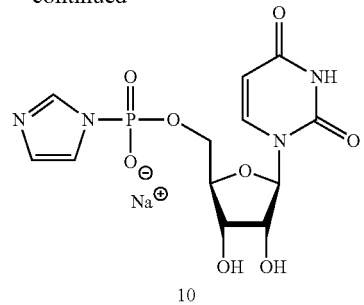

10

UMP-NBu$_3$ (2.22 g, 4.36 mmol) was dissolved in DMF (25 mL) and CDI (1.17 g, 7.2 mmol) was added and the reaction was stirred for 30 minutes. MeOH (177 µL, 4.36 mmol) was added and the reaction was stirred for 15 minutes. The reaction was placed under vacuum for 15 minutes Subsequent 6-azido-6-deoxy-GalNAc-1-monophosphate 5b (1.60 g, 4.9 mmol) in DMF (25 mL) was added followed by the addition of NMI·HCl (2.25 g, 14.4 mmol). After stirring overnight an extra amount of activated UMP-NBu$_4$ was added. Therefore, in a separate flask UMP-NBu$_3$ (700 mg, 1.4 mmol), was dissolved in DMF (10 mL) and CDI (371 mg, 2.3 mmol) was added. This mixture stirred for 5 minutes and added to the reaction. The reaction mixture was stirred overnight at room temperature and concentrated under reduced pressure. The crude mixture was dissolved in water and split in three portions. One portion was loaded onto 300 mL Q-Sepharose Fast Flow® ion exchange column (A: 25 mM ammonium bicarbonate, B: 250 mM ammonium bicarbonate) at 10 ml/min. Then the column was washed with 25 mM ammonium bicarbonate solution followed by a gradient to 40% B to elute the product. The product fractions were pooled and concentrated under reduced pressure to yield compound 9. This procedure was repeated twice to yield UDP-6"-N$_3$-6"-deoxy-GalNAc (9, ammonium-salt) (2.72 g, 47% purity by $^1$H-qNMR, 2.0 mmol, 41% yield). $^1$H-NMR (400 MHz, D$_2$O): δ 7.82 (d, J=8.4 Hz, 1H), 5.84-5.81 (m, 2H), 5.42 (dd, J=3.6, 3.6 Hz, 1H), 4.26-4.20 (m, 3H), 4.16-4.08 (m, 5H), 3.90-3.89 (m, 1H), 3.86-3.83 (m, 1H), 3.47 (AB system, J=7.6, 5.2 Hz, 1H), 3.36 (AB system, J=7.2, 5.6 Hz, 1H), 1.95 (s, 3H).

Example 4-5: Synthesis of UMP Imidazole Phosphate Ester 10 from UMP·NBu$_3$

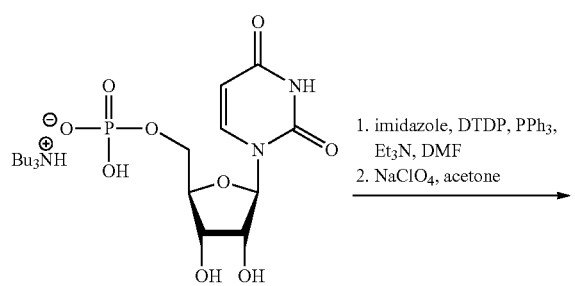

To a round-bottom containing UMP tributylammonium salt (UMP·NBu$_3$, 6.05 g, 91.4% by QNMR, 10.84 mmol, 1.00 equiv.) and imidazole (7.38 g, 108.4 mmol, 10.0 equiv.) was added dry DMF (55.0 mL), followed by 2,2-dithiopyridine (3.36 g, 15.25 mmol, 1.41 equiv.). To the resulting colourless solution was added Et$_3$N (6.05 mL, 43.4 mmol, 4 equiv.), followed by PPh$_3$ (8.53 g, 32.5 mmol, 3.00 equiv.), generating a yellow solution. The mixture was stirred under N$_2$ for 2 hours and then cooled in an ice bath to 0° C. To the cold reaction mixture was added 553 mL of a 0.106 M solution of NaClO$_4$ in acetone. The resulting yellow suspension was cooled in an ice bath to 0° C. and then filtered over a glassfilter and washed with cold dry acetone (3×). The residue was conc. in vacuo and dried over P$_2$O$_5$, affording 4.68 g of an off-white solid (88.7% pure by qNMR, 4.15 g corrected, 10.47 mmol, 96.7% yield). $^1$H NMR (400 MHz, D$_2$O) δ (ppm): 7.93 (s, 1H), 7.84 (d, J=8.2 Hz, 1H), 7.32 (q, J=1.4 Hz, 1H), 7.13-7.01 (m, 1H), 5.96 (d, J=5.3 Hz, 1H), 5.79 (d, J=8.1 Hz, 1H), 4.18 (t, J=5.0 Hz, 1H), 4.14-3.94 (m, 4H), 3.07-2.97 (m, 1H), 2.93-2.87 (m, 1H).

Example 4-6: Synthesis of 8 from 5a and 10

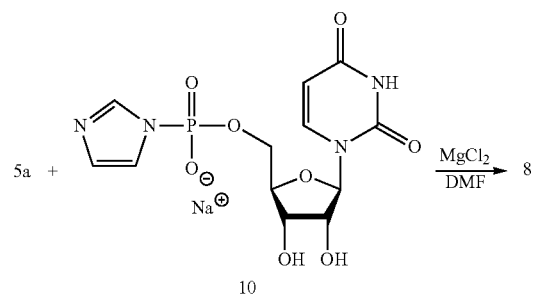

To a flame-dried roundbottom flask with a stirring bar was added 6-N$_3$-sugarmonophosphate 5a (2.346 g, 77.6% by qNMR, 4.437 mmol, 1.00 equiv.) and dry DMF (27.5 mL). The resulting solution was cooled in an ice-bath and MgCl$_2$ (486 mg, 5.105 mmol, 1.15 equiv.) was added. The resulting mixture was stirred for 13 minutes, generating a fine suspension. The ice-bath was removed, allowing the RM to slowly warm to rt. Next, 10 (2.282 g, 88.7% by qNMR, 1.15 equiv.) was added portion-wise over 30 seconds while stirring. The resulting light-yellow suspension was stirred at rt for 18 hours. The reaction mixture was then concentrated in vacuo, affording 9.20 g of a hazy yellow oil, which was used in the next step without further purification.

Example 4-7: Synthesis of UDP 6-azido-GalNAc (9) by Deprotection of 8

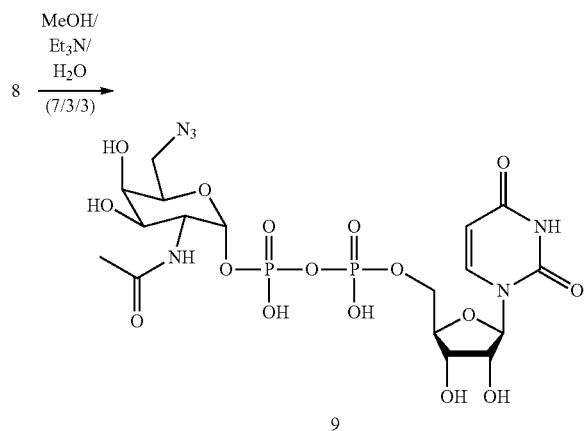

Crude 8 was dissolved in H₂O (32 mL) and MeOH (32 mL), followed by the addition of Et₃N (32 mL). The resulting hazy yellow suspension was stirred at rt for 22 hours and then conc. in vacuo, affording a hazy yellow oil. The residue was dissolved in H₂O (222 mL) and slowly pulled over a plug of DEAE Sephadex A-25. The DEAE plug was prepared as follows: a glass filter P3 (6 cm diameter) was loaded with DEAE SephadexA-25 (12.5 g) and suspended in H₂O, washed with 1 M NH₄HCO₃, followed by washings with H₂O. Consequently, a 3.5 cm high plug (circa 100 mL) DEAE Sephadex was obtained. The DEAE plug was then loaded with the solution of crude 9 (circa 355 µmol product/g resin) in H₂O (222 mL), using minimal vacuum suction, over the course of 15 minutes. The plug was washed with demiwater (60 mL, 3×), followed by washings with 20 mM NH₄HCO₃ (100 mL, 4×). Finally, the product was eluted with 1 M NH₄HCO₃ (100 mL, 3×). The eluted product was conc. in vacuo, co-evaporated once with H₂O and then lyophilized, affording 9 (3.986 g, 69.2% by qNMR, 4.36 mmol, 98.3% yield) as an off-white solid. $^1$H NMR (400 MHz, D₂O) δ (ppm): 7.88 (d, J=8.2 Hz, 1H), 5.94-5.84 (m, 2H), 5.46 (dd, J=7.2, 3.4 Hz, 1H), 4.33-4.24 (m, 2H), 4.24-4.06 (m, 5H), 3.97-3.84 (m, 2H), 3.51 (dd, J=12.8, 7.3 Hz, 1H), 3.41 (dd, J=12.8, 7.3 Hz, 1H), 2.00 (s, 3H).

Example 5-1: Synthesis of 6-azido-1-(di-2-cyano-ethyl)phosphate-GalNAc (12)

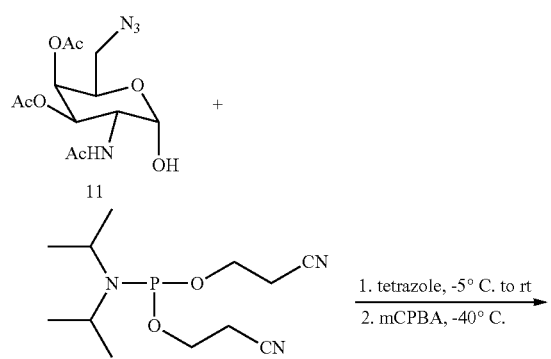

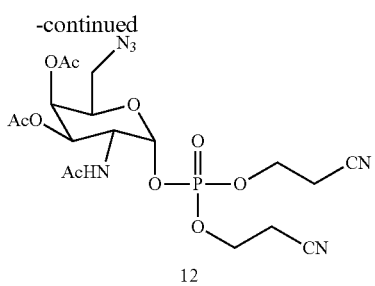

Method A: A round-bottomed flask containing hemi-acetal compound 11 (1.20 g, 3.63 mmol) and a 0.45 M solution of 1-H-tetrazole in acetonitrile (32 mL, 14.5 mmol, 4 eq) was concentrated and co-evaporated from dry toluene (3×20 mL). The residue was taken up in dry DCM (40 mL) before cooling (−5° C.) and treatment with a solution of 2-cyanoethyl-N,N'-diisopropyl-phosphorochloro-amidite (2.0 mL, 7.27 mmol, 2 eq) in dry DCM (4.0 mL), dropwise, over 15 min with stirring under Ar (g). The reaction was allowed to warm slowly to room temperature and stirring continued for a further 80 min, before cooling (−40° C.) and treatment with mCPBA (2.10 g, 9.08 mmol, 2.5 eq). The reaction was allowed to warm slowly to room temperature and stirring continued for a further 30 min before partitioning between DCM (100 mL) and 10% sodium thiosulfate solution (100 mL). The organic layer was washed, in-turn, with saturated NaHCO₃ solution and brine (100 mL each), dried (MgSO₄), filtered and concentrated. Flash-column chromatography (80 g SiO₂ cartridge; 70-100% EtOAc in petroleum ether 40-60, then 0-25% MeCN in EtOAc) of the residue afforded firstly oxazoline (F2) (100 mg, 0.32 mmol, 8.8% yield), then compound 12 (F1) as a white foam (1.10 g, 2.13 mmol, 59% yield).

Method B: A cooled (−5° C.) and stirred mixture of hemi-acetal compound 11 (547 mg, 1.65 mmol) and 4,5-dicyanoimidazole (781 mg, 6.62 mmol, 4 eq) in dry DCM (15 mL) under Ar (g) was added a solution of 2-cyanoethyl-N,N'-diisopropyl-phosphorochloroamidite (0.9 mL, 3.31 mmol, 2 eq) in dry DCM (2.0 mL), dropwise, over 15 min with stirring. The reaction was allowed to warm slowly to room temperature and stirring continued for a further 80 min, before cooling (−40° C.) and treatment with mCPBA (927 mg, 4.14 mmol, 2.5 eq). The reaction was allowed to warm slowly to room temperature and stirring continued for a further 30 min before addition of 10% sodium thiosulfate solution (10 mL). The organic layer washed with saturated NaHCO₃ solution (10 mL), dried (MgSO₄), filtered and concentrated. Flash-column chromatography (40 g SiO₂ cartridge; 70-100% EtOAc in petroleum ether 40-60, then 0-50% MeCN in EtOAc) of the residue afforded compound 3 as a white foam (540 mg, 1.05 mmol, 63% yield). NMR shows compound 12 is 98% pure; LCMS (ELSD) shows compound 12 is 95% pure.

Method C: A cooled (−5° C.) and stirred mixture of hemi-acetal compound 11 (547 mg, 1.65 mmol) and 4,5-dicyanoimidazole (781 mg, 6.62 mmol, 4 eq) in dry DCM (15 mL) under Ar (g) was added a solution of 2-cyanoethyl-N,N'-diisopropyl-phosphorochloroamidite (0.9 mL, 3.31 mmol, 2 eq) in dry DCM (2.0 mL), dropwise, over 15 min with stirring. The reaction was allowed to warm slowly to room temperature and stirring continued for a further 80 min, before cooling (−40° C.) and treatment with mCPBA (927 mg, 4.14 mmol, 2.5 eq). The reaction was allowed to warm slowly to room temperature and stirring continued for a further 30 min before addition of 10% sodium thiosulfate solution (10 mL). The organic layer washed with saturated NaHCO₃ solution (10 mL), dried (MgSO₄), filtered and concentrated. Flash-column chromatography (40 g SiO₂ cartridge; 70-100% EtOAc in petroleum ether 40-60, then 0-50% MeCN in EtOAc) of the residue afforded compound 3 as a white foam (540 mg, 1.05 mmol, 63% yield). NMR shows compound 12 is 98% pure; LCMS (ELSD) shows compound 12 is 95% pure.

Method D: A cooled (−5° C.) and stirred mixture of hemi-acetal compound 11 (547 mg, 1.65 mmol) and BnS-1-H-tetrazole (1.27 g, 6.62 mmol, 4 eq) in dry DCM (15 mL) under Ar (g) was added a solution of 2-cyanoethyl-N,N'-diisopropyl-phosphorochloroamidite (0.9 mL, 3.31 mmol, 2 eq) in dry DCM (2.0 mL), dropwise, over 15 min with stirring. The reaction was allowed to warm slowly to room temperature and stirring continued for a further 80 min, before cooling (−40° C.) and treatment with mCPBA (927 mg, 4.14 mmol, 2.5 eq). The reaction was allowed to warm slowly to room temperature and stirring continued for a further 30 min before addition of 10% sodium thiosulfate solution (10 mL). The organic layer washed with saturated NaHCO₃ solution (10 mL), dried (MgSO₄), filtered and concentrated. Flash-column chromatography (40 g SiO₂ cartridge; 70-100% EtOAc in petroleum ether 40-60, then 0-50% MeCN in EtOAc) of the residue afforded compound 12 as a white foam (362 mg, 0.70 mmol, 43% yield). Both NMR and LCMS (ELSD) show compound 12 is >90% pure.

Example 5-2: Synthesis of 6-azido-1-phosphate-GalNAc (5b)

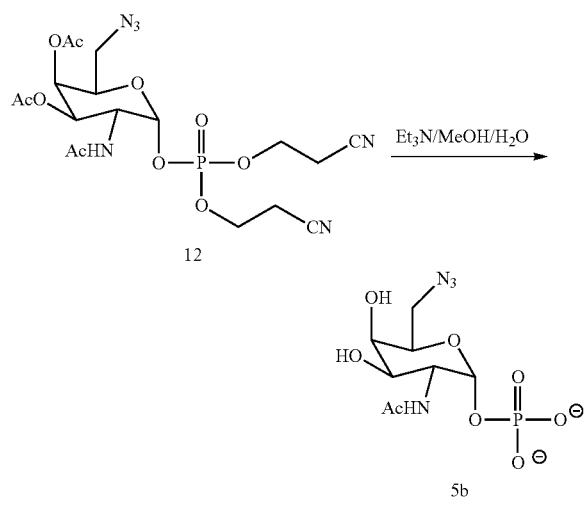

Compound 12 (1.60 g, 3.10 mmol) was treated with an 8:35:57 mixture of TEA/MeOH/Water (100 mL) at 35° C. until LCMS showed the reaction to be complete (3 d). The mixture was partially concentrated on a rotary evaporator to the aqueous fraction, then freeze-dried. Freeze-drying (twice) repeated until excess of triethylamine removed (determined by NMR). The residue was triturated with acetone (2×100 mL) that was removed by decanting, and the residue dried under high vacuum to give compound 5b (1.33 g, 2.53 mmol, 82% yield) as a clear foam.

Example 5-3: Coupling of 5b with UMP-morpholidate

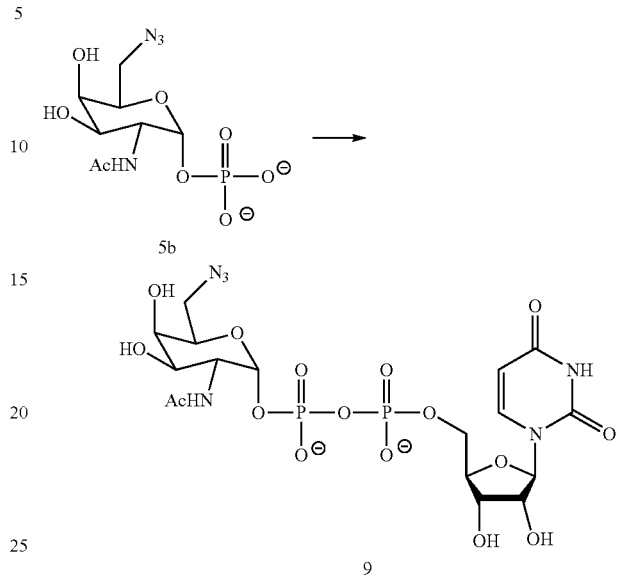

Method A: To a flame-dried round-bottomed flask equipped with a stirring bar under argon (g) was added compound 5b (81 mg, 0.15 mmol, 1.00 eq), dry DMF (2.0 mL), UMP-morpholidate (116 mg, 0.17 mmol, 1.1 eq) and 4,5-dicyanoimidazole (DCI, 56 mg, 0.48 mmol, 3.2 eq). The resulting solution was stirred at 35° C. for 20 h; LCMS of the crude mixture indicated that starting material 5b was not consumed. More starting material UMP-morpholidate (35 mg, 0.3 eq) was added and reaction stirred for a further 6 h: LCMS showed levels of 5b to be 2.5%. The mixture was treated with MeCN (10 mL), then centrifuged and liquids decanted (this process was repeated once more) to give a white solid, which was taken up in water and added to DEAE-sepharose media (2.4×13 cm), which was eluted, in turn, with 50 ml each of water and increasing concentrations of triethylammonium bicarbonate (TEAB) 100 mM, 200 mM, 300 mM and 400 mM. The main bulk of compound was eluted in the 300 mM TEAB fraction and freeze-dried to give 120 mg of compound 9, which by LCMS contained compound 5b (based on presence of mass ion of compound 5b in −ve mode). The residue was taken up in water and subjected to C18-chromatography (30 g cartridge; eluent=100% 10 mM TEAB). To give, firstly, a 2:1 mix of UMP and compound 5b (11 mg), and secondly, compound 9 (65 mg, 51%) that was pure by NMR and LCMS.

Method B: To a flame-dried round-bottomed flask equipped with a stirring bar under argon (g) was added compound 5b (53 mg, 0.10 mmol, 1.00 eq), dry DMF (1.5 mL), UMP-morpholidate (90 mg, 0.13 mmol, 1.3 eq) and DCI (42 mg, 0.36 mmol, 3.6 eq). The resulting solution was stirred at 35° C. for 20 h; LCMS of the crude mixture indicated that starting material UMP-morpholidate was consumed. The mixture was treated with acetone (10 mL), then centrifuged and liquids decanted (this process was repeated once more) to give a white solid, which was taken up in water and added to DEAE-sepharose media (2.4×13 CM), which was eluted, in turn, with 50 ml each of water and increasing concentrations of TEAB 100 mM, 200 mM, 300 mM and 400 mM. The main bulk of compound was eluted in the 300 mM TEAB fraction and freeze-dried to give 102 mg of compound 9, which by LCMS (ELSD) contained 15% of compound 5b, while NMR showed the amount of compound 5b is 46%.

Method C: To a flame-dried round-bottomed flask equipped with a stirring bar under argon (g) was added compound 5b (53 mg, 0.10 mmol, 1.00 eq), dry DMF (1.5 mL), UMP-morpholidate (90 mg, 0.13 mmol, 1.3 eq) and EtS-1-H-tetrazole (47 mg, 0.36 mmol, 3.6 eq). The resulting solution was stirred at 35° C. for 40 h; LCMS of the crude mixture indicated that starting material UMP-morpholidate still remained. The temperature was increased to 40° C. and stirring continued for 20 h. The mixture was treated with acetone (10 mL) and centrifuged (repeated once more) to give 9 as a white solid, which LCMS (ELSD) contained 8% of compound 5b, while NMR showed the amount of compound 5b is 40%.

Method D: To a flame-dried round-bottomed flask equipped with a stirring bar under argon (g) was added compound 5b (53 mg, 0.10 mmol, 1.00 eq), dry DMF (1.5 mL), UMP-morpholidate (90 mg, 0.13 mmol, 1.3 eq) and BnS-1-H-tetrazole (69 mg, 0.36 mmol, 3.6 eq). The resulting solution was stirred at 35° C. for 40 h; LCMS of the crude mixture indicated that starting material UMP-morpholidate still remained. The temperature was increased to 40° C. and stirring continued for 6 h. The mixture was treated with acetone (10 mL) and centrifuged (repeated once more) to give 9 as a white solid, which LCMS (ELSD) contained 13% of compound 5b, while NMR showed the amount of compound 5b is 39%.

The invention claimed is:

1. A method for preparing a 6-azido-6-deoxy-1-monophosphate monosaccharide compound having structure (Va) or (Vb) according to the scheme:

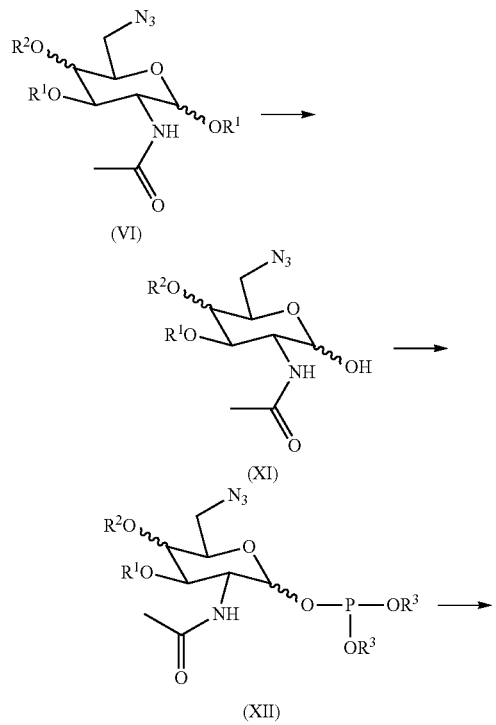

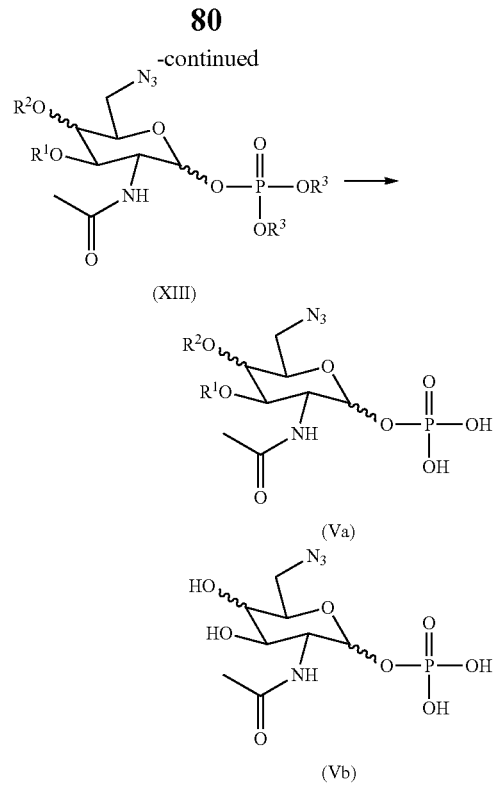

comprising:
(x1) deprotecting the anomeric position of a compound having structure (VI) to form 1-hydroxy-monosaccharide compound having structure (XI);
(x2) converting the 1-hydroxy-monosaccharide compound having structure (XI) into a 6-azido-6-deoxy-1-monophosphite diester having structure (XII);
(x3) oxidizing the monophosphite diester having structure (XII) in the presence of an oxidizing agent, to form a 1-monophosphate diester compound having structure (XIII);
(x4) deprotecting the phosphate diester having structure (XIII) to form the 1-monophosphate monosaccharide compound having structure (Va), or concomitantly deprotecting the phosphate diester and monosaccharide having structure (XIII) to form a 1-monophosphate monosaccharide compound having structure (Vb),
wherein $R^1$ and $R^2$ are independently selected from optionally substituted C(O)-alkyl, optionally substituted C(O)-aryl and optionally substituted C(O)-arylalkyl, and $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$ alkyl, fluorenylmethyl, 2-pyridylethyl, and phenyl-$C_{1-2}$-alkyl, wherein the phenyl group of phenyl-C1-2-alkyl or the phenyl group of 2-arylsulfonylethyl, when 2-arylsulfonylethyl is 2-phenylsulfonylethyl, is optionally substituted with one or more halides or a nitro or methoxy group.

2. The method according to claim 1, wherein the method is for preparing the monosaccharide compound having structure (Vb) and step (x4) involves concomitantly deprotecting the phosphate diester and monosaccharide having structure (XIII) to form the 1-monophosphate monosaccharide compound having structure (Vb).

3. The method according to claim 1, wherein the method is for preparing the monosaccharide compound having structure (Va) and step (x4) involves deprotecting the phosphate diester having structure (XIII) to form the 1-monophosphate monosaccharide compound having structure (Va).

4. The method according to claim 1, wherein the 6-azido-6-deoxy monosaccharide having structure (VI) is prepared from a 6-azido-6-deoxy monosaccharide compound having structure (I):

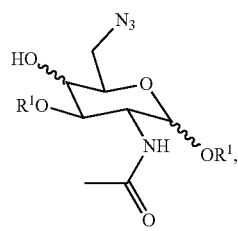

(I)

wherein R$^1$ is independently selected from optionally substituted C(O)-alkyl, optionally substituted C(O)-aryl and optionally substituted C(O)-arylalkyl.

5. The method according to claim 4, wherein the 6-azido-6-deoxy monosaccharide having structure (VI) is prepared by:
(e) protecting the 6-azido-6-deoxy monosaccharide having structure (I) to form 6-azido-6-deoxy monosaccharide compound having structure (VI).

6. The method according to claim 4, wherein the 6-azido-6-deoxy monosaccharide compound having structure (I) is prepared according to the scheme:

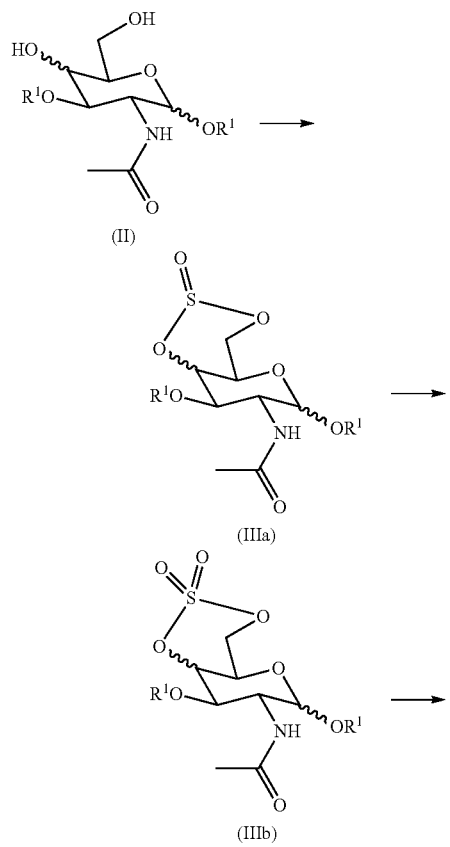

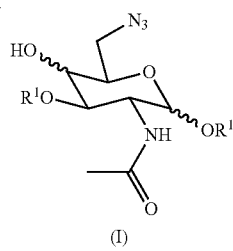

(I)

comprising:
(b) reacting a diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form the 6-azido-6-deoxy monosaccharide having structure (I),
wherein R$^1$ is independently selected from C(O)-alkyl, C(O)-aryl and C(O)-arylalkyl.

7. The method according to claim 1, wherein the 6-azido-6-deoxy-1-monophosphate monosaccharide is 6-azido-6-deoxy-1-monophosphate N-acetyl-D-glucosamine.

8. The method according to claim 1, wherein the 6-azido-6-deoxy-1-monophosphate monosaccharide is 6-azido-6-deoxy-1-monophosphate N-acetyl-D-galactosamine.

9. The method according to claim 1, wherein the 6-azido-6-deoxy-1-monophosphate monosaccharide compound having structure (Va) or (Vb) is further converted into a nucleoside diphosphate having structure (IX), or a salt thereof:

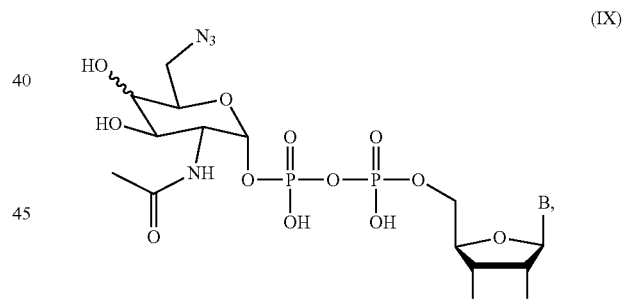

wherein B is a nucleobase.

10. The method according to claim 9, wherein 1-monophosphate monosaccharide compound having structure (Va) is converted into nucleoside diphosphate having structure (IX), or salt thereof, according to the scheme:

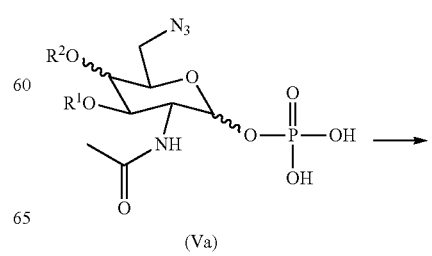

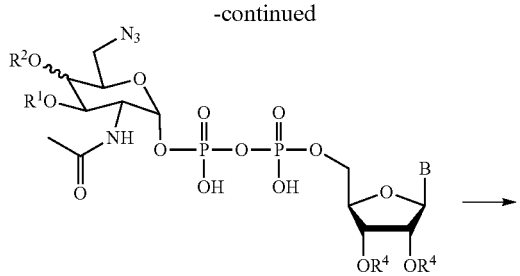

(VIII)

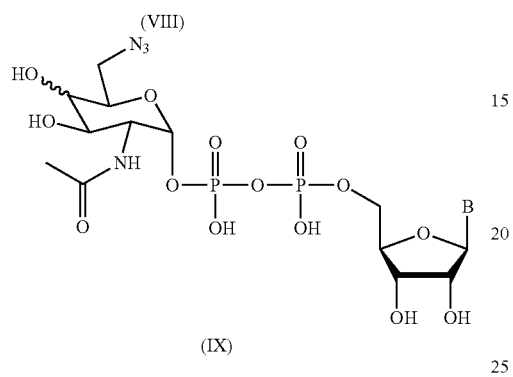

(IX)

comprising:
(i) reacting the compound having structure (Va) with a nucleoside monophosphate to provide an acylated nucleoside diphosphate having structure (VIII); and
(j) deprotecting the acylated nucleoside diphosphate having structure (VIII) to obtain nucleoside diphosphate having structure (IX) or salt thereof,
wherein $R^4$ are both hydrogen or both occurrences of $R^4$ are joined together via a carbonyl moiety,
or according to the scheme:

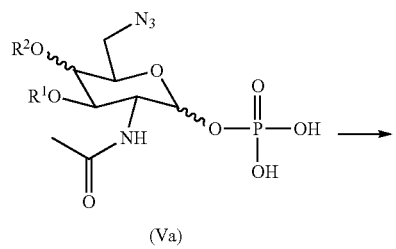

(Vb)

(IX)

comprising:
(j1) deprotecting the compound having structure (Va) to obtain a 1-monophosphate monosaccharide compound having structure (Vb),
(i1) reacting the compound having structure (Vb) with a nucleoside monophosphate to provide a nucleoside diphosphate having structure (IX).

11. The method according to claim 10, wherein step (j1) is part of step (x4) that affords the compound having structure (Vb) in one step from the phosphate diester having structure (XIII).

12. The method according to claim 1, wherein each occurrence of $R^1$ and $R^2$ is C(O) Me, C(O) tBu, C(O) Ph, or C(O) $CH_2$Ph.

13. The method according to claim 1, which is for preparing a nucleoside diphosphate having structure (IX) or salt thereof according to the scheme:

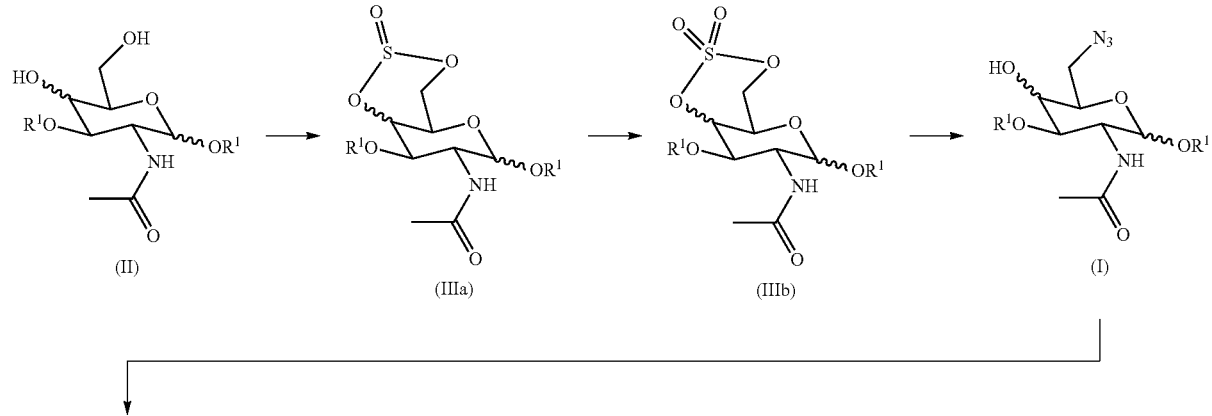

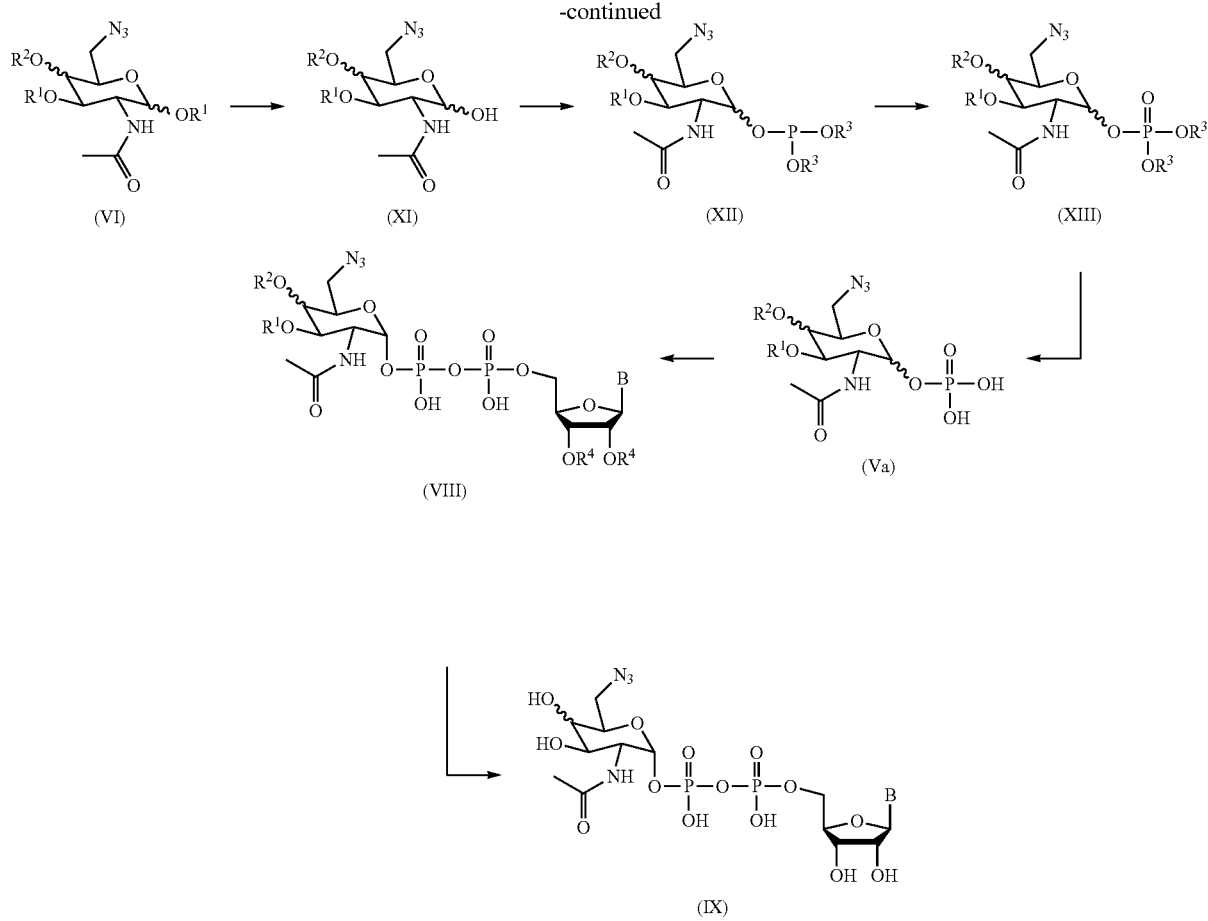

(VI) (XI) (XII) (XIII) (Va) (VIII) (IX)

wherein:
R¹ is independently selected from optionally substituted C(O)-alkyl, optionally substituted C(O)-aryl and optionally substituted C(O)-arylalkyl;
R² is selected from optionally substituted C(O)-alkyl, optionally substituted C(O)-aryl and optionally substituted C(O)-arylalkyl;
R³ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$ alkyl, fluorenylmethyl, 2-pyridylethyl, and phenyl-$C_{1-2}$-alkyl, wherein the phenyl group of phenyl-$C_{1-2}$-alkyl or the phenyl group of 2-arylsulfonylethyl, when 2-arylsulfonylethyl is 2-phenylsulfonylethyl, is optionally substituted with one or more halides or a nitro or methoxy group;
R⁴ are both hydrogen or both occurrences of R⁴ are joined together via a carbonyl moiety;
B is a nucleobase,
wherein the process comprises:
(a) converting N-acetylglucosamine or N-acetylgalactosamine into a 1,3-di-acylated compound having structure (II);
(b) reacting the diol having structure (II) with a sulfitylating agent to form a cyclic sulfite having structure (IIIa);
(c) reacting the cyclic sulfite having structure (IIIa) with an oxidizing agent to form a cyclic sulfate having structure (IIIb);
(d) reacting the cyclic sulfate having structure (IIIb) with an inorganic azide to form a 6-azido-6-deoxy monosaccharide having structure (I);
(e) protecting the 6-azido-6-deoxy monosaccharide having structure (I) to form 6-azido-6-deoxy monosaccharide compound having structure (VI);
(x1) deprotecting the anomeric position of compound having structure (VI) to form 1-hydroxy-monosaccharide compound having structure (XI);
(x2) converting the 1-hydroxy-monosaccharide compound having structure (XI) into the 6-azido-6-deoxy-1-monophosphite diester having structure (XII);
(x3) oxidizing the monophosphite diester having structure (XII) in the presence of an oxidizing agent, to form the 1-monophosphate diester compound having structure (XIII);
(x4) deprotecting the phosphate diester having structure (XIII) to form the 1-monophosphate monosaccharide compound having structure (Va), or salt thereof;
(i) reacting the compound having structure (Va) with a nucleoside monophosphate into an acylated nucleoside diphosphate having structure (VIII); and
(j) deprotecting the acylated nucleoside diphosphate having structure (VIII) to obtain nucleoside diphosphate having structure (IX), or salt thereof.

14. The method according to claim 1, which is for preparing a nucleoside diphosphate having structure (IX) or salt thereof according to the scheme:

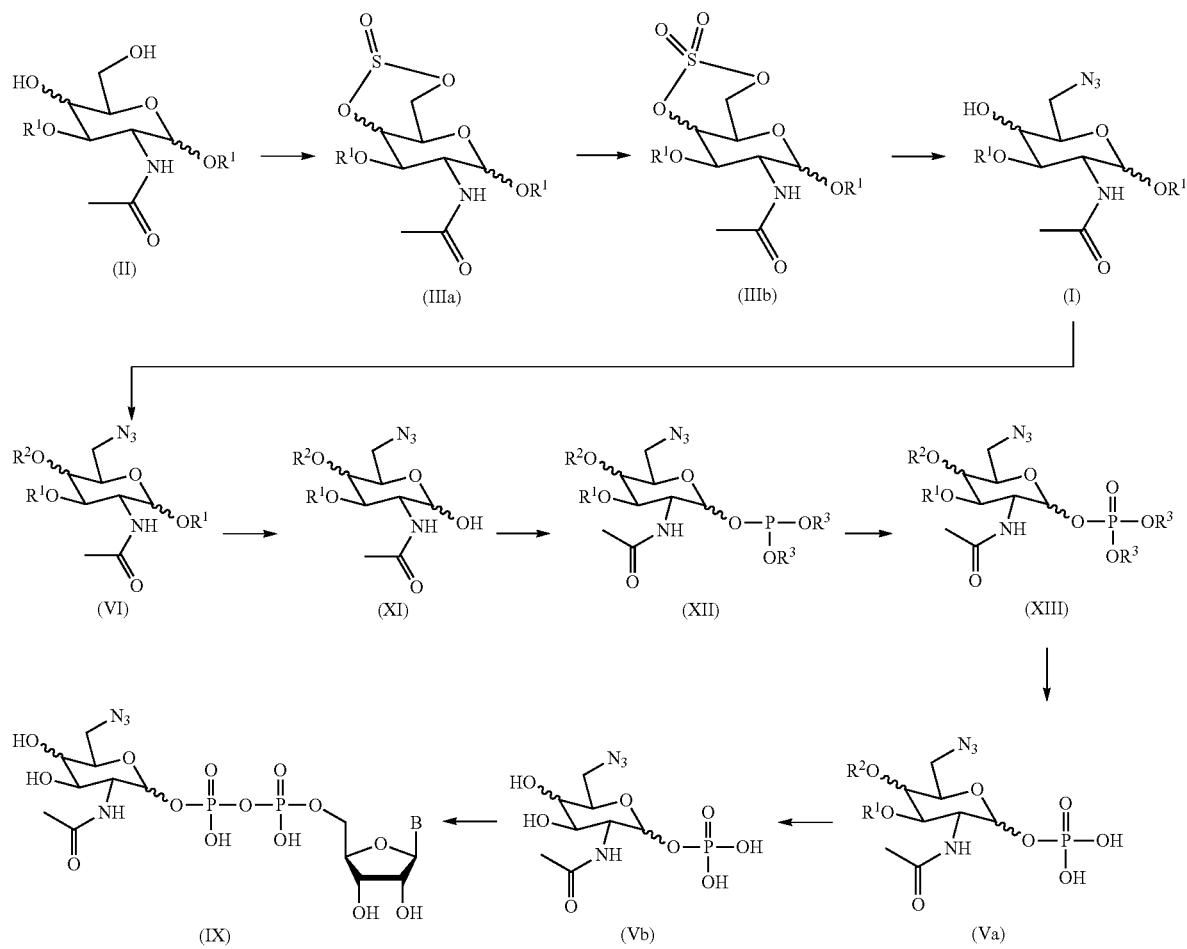

wherein:
- $R^1$ is independently selected from optionally substituted C(O)-alkyl, optionally substituted C(O)-aryl and optionally substituted C(O)-arylalkyl;
- $R^2$ is selected from optionally substituted C(O)-alkyl, optionally substituted C(O)-aryl and optionally substituted C(O)-arylalkyl;
- $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$ alkyl, fluorenylmethyl, 2-pyridylethyl, and phenyl-$C_{1-2}$-alkyl, wherein the phenyl group of phenyl-$C_{1-2}$-alkyl or the phenyl group of 2-arylsulfonylethyl, when 2-arylsulfonylethyl is 2-phenylsulfonylethyl, is optionally substituted with one or more halides or a nitro or methoxy group;
- B is a nucleobase, wherein the process comprises:
- (a) converting N-acetylglucosamine or N-acetylgalactosamine into a 1,3-di-acylated compound having structure (II);
- (b) reacting the diol having structure (II) with a sulfitylating agent to form a cyclic sulfite having structure (IIIa);
- (c) reacting the cyclic sulfite having structure (IIIa) with an oxidizing agent to form a cyclic sulfate having structure (IIIb);
- (d) reacting the cyclic sulfate having structure (IIIb) with an inorganic azide to form a 6-azido-6-deoxy monosaccharide having structure (I);
- (e) protecting the 6-azido-6-deoxy monosaccharide having structure (I) to form 6-azido-6-deoxy monosaccharide compound having structure (VI);
- (x1) deprotecting the anomeric position of compound having structure (VI) to form 1-hydroxy-monosaccharide compound having structure (XI);
- (x2) converting the 1-hydroxy-monosaccharide compound having structure (XI) into the 6-azido-6-deoxy-1-monophosphite diester having structure (XII);
- (x3) oxidizing the monophosphite diester having structure (XII) in the presence of an oxidizing agent, to form the 1-monophosphate diester compound having structure (XIII);
- (x4) deprotecting the phosphate diester having structure (XIII) to form the 1-monophosphate monosaccharide compound having structure (Va), or salt thereof;
- (j1) deprotecting the compound having structure (Va) to obtain a 1-monophosphate monosaccharide compound having structure (Vb), or salt thereof;
- (i1) reacting the compound having structure (Vb) with a nucleoside monophosphate into a nucleoside diphosphate having structure (IX).

15. The method according to claim 14, wherein steps (x4) and (j1) are performed in a single deprotection step that affords the compound having structure (Vb).

16. A method for preparing a 6-azido-6-deoxy-1-monophosphate monosaccharide compound having structure (Va) according to the scheme:

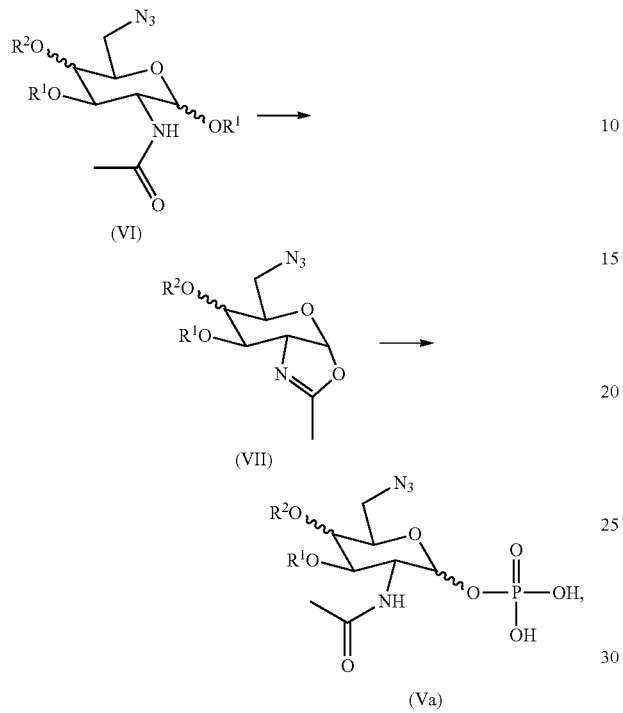

comprising:
(f) converting a 6-azido-6-deoxy monosaccharide having structure (VI) in the presence of one or more Lewis acids to form an oxazoline compound having structure (VII);
(g) reacting the oxazoline compound having structure (VII) with phosphoric acid to form the 6-azido-6-deoxy-1-monophosphate monosaccharide compound having structure (Va) or a salt thereof,
wherein $R^1$ and $R^2$ are independently selected from optionally substituted C(O)-alkyl, optionally substituted C(O)-aryl and optionally substituted C(O)-arylalkyl.

17. A compound selected from the group consisting of:
(i) a 6-azido-6-deoxy monosaccharide compound having structure (I):

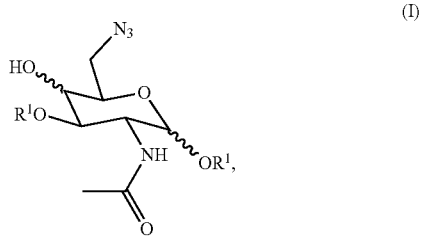

wherein $R^1$ is independently selected from optionally substituted C(O)-alkyl, optionally substituted C(O)-aryl and optionally substituted C(O)-arylalkyl;
(ii) a cyclic sulfate monosaccharide compound having structure (III):

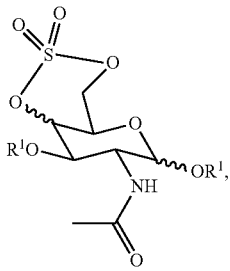

wherein $R^1$ is independently selected from optionally substituted C(O)-alkyl, optionally substituted C(O)-aryl and optionally substituted C(O)-arylalkyl;
(iii) a nucleoside diphosphate having structure (VIII):

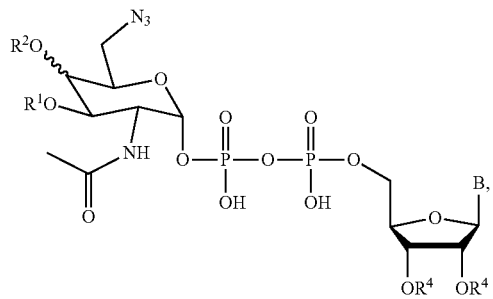

wherein:
B is a nucleobase;
$R^1$ is independently selected from optionally substituted C(O)-alkyl, optionally substituted C(O)-aryl and optionally substituted C(O)-arylalkyl;
$R^2$ is selected from optionally substituted C(O)-alkyl, optionally substituted C(O)-aryl and optionally substituted C(O)-arylalkyl;
$R^4$ are both hydrogen or both occurrences of $R^4$ are joined together via a carbonyl moiety;
(iv) a 1-hydroxy-monosaccharide compound having structure (XI):

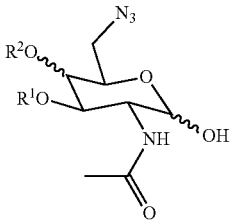

wherein:
$R^1$ is selected from optionally substituted C(O)-alkyl, optionally substituted C(O)-aryl and optionally substituted C(O)-arylalkyl;
$R^2$ is selected from optionally substituted C(O)-alkyl, optionally substituted C(O)-aryl and optionally substituted C(O)-arylalkyl;

(v) a phosphite having structure (XII):

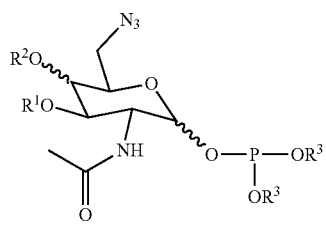

wherein:

- $R^1$ is selected from optionally substituted C(O)-alkyl, optionally substituted C(O)-aryl and optionally substituted C(O)-arylalkyl;
- $R^2$ is selected from optionally substituted C(O)-alkyl, optionally substituted C(O)-aryl and optionally substituted C(O)-arylalkyl;
- $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$ alkyl, fluorenylmethyl, 2-pyridylethyl, and phenyl-$C_{1-2}$-alkyl, wherein the phenyl group of phenyl-$C_{1-2}$-alkyl or the phenyl group of 2-arylsulfonylethyl, when 2-arylsulfonylethyl is 2-phenylsulfonylethyl, is optionally substituted with one or more halides or a nitro or methoxy group;

(vi) a phosphate diester having structure (XIII):

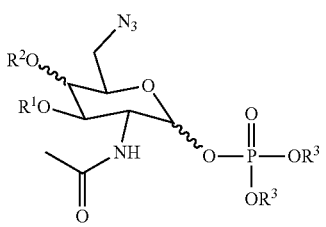

wherein:

- $R^1$ is selected from optionally substituted C(O)-alkyl, optionally substituted C(O)-aryl and optionally substituted C(O)-arylalkyl;
- $R^2$ is selected from optionally substituted C(O)-alkyl, optionally substituted C(O)-aryl and optionally substituted C(O)-arylalkyl;
- $R^3$ is selected from $C_{1-6}$ alkyl, allyl, 2-cyanoethyl, 2-alkylsulfonylethyl, 2-arylsulfonylethyl, 2,2,2-trichloroethyl, $CH_2OC(O)$ alkyl, fluorenylmethyl, 2-pyridylethyl, and phenyl-$C_{1-2}$-alkyl, wherein the phenyl group of phenyl-$C_{1-2}$-alkyl or the phenyl group of 2-arylsulfonylethyl, when 2-arylsulfonylethyl is 2-phenylsulfonylethyl, is optionally substituted with one or more halides or a nitro or methoxy group;

(vii) an oxazoline compound having structure (VII):

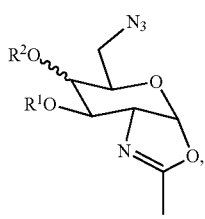

wherein $R^1$ and $R^2$ is independently selected from H, optionally substituted C(O)-alkyl, optionally substituted C(O)-aryl and optionally substituted C(O)-arylalkyl; and (viii) a mixture comprising the α-anomeric form and the β-anomeric form of the 6-azido-6-deoxy-1-monophosphate monosaccharide compound having structure (Va):

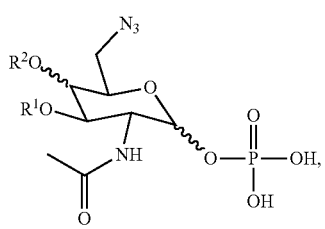

wherein the molar ratio between the α- and β-anomeric form is in the range of 3/1 to 10/1, wherein both anomeric forms of compound (Va) may be in salt form, wherein $R^1$ and $R^2$ are independently selected from optionally substituted C(O)-alkyl, optionally substituted C(O)-aryl and optionally substituted C(O)-arylalkyl.

18. The compound according to claim 17, wherein $R^1$ and $R^2$ are selected from C(O) Me, C(O) tBu, C(O) Ph, or C(O) $CH_2Ph$.

19. The compound according to claim 17, wherein the monosaccharide moiety of the 6-azido-6-deoxy monosaccharide compound having structure (I), the cyclic sulfate monosaccharide compound having structure (III), the nucleoside diphosphate having structure (VIII), the 1-hydroxy-monosaccharide compound having structure (XI), the phosphite having structure (XII), the phosphate diester having structure (XIII), the oxazoline compound having structure (VII) or the 6-azido-6-deoxy-1-monophosphate monosaccharide compound having structure (Va) is N-acetyl-D-glucosamine.

20. The compound according to claim 17, wherein the monosaccharide moiety of the 6-azido-6-deoxy monosaccharide compound having structure (I), the cyclic sulfate monosaccharide compound having structure (III), the nucleoside diphosphate having structure (VIII), the 1-hydroxy-monosaccharide compound having structure (XI), the phosphite having structure (XII), the phosphate diester having structure (XIII), the oxazoline compound having structure (VII) or the 6-azido-6-deoxy-1-monophosphate monosaccharide compound having structure (Va) is N-acetyl-D-galactosamine.

* * * * *